(12) United States Patent
Hamilton et al.

(10) Patent No.: US 11,090,026 B2
(45) Date of Patent: Aug. 17, 2021

(54) SYSTEMS AND METHODS FOR DETERMINING CLINICAL INDICATIONS

(71) Applicant: NovaSignal Corp., Los Angeles, CA (US)

(72) Inventors: Robert Hamilton, Los Angeles, CA (US); Michael O'Brien, Los Angeles, CA (US); Leo Petrossian, Los Angeles, CA (US); Shankar Radhakrishnan, Los Angeles, CA (US); Corey Thibeault, Los Angeles, CA (US); Seth Wilk, Los Angeles, CA (US); Jan Zwierstra, Los Angeles, CA (US)

(73) Assignee: NovaSignal Corp., Los Angeles, CA (US)

(*) Notice: Subject to any disclaimer, the term of this patent is extended or adjusted under 35 U.S.C. 154(b) by 623 days.

(21) Appl. No.: 15/399,710

(22) Filed: Jan. 5, 2017

(65) Prior Publication Data

US 2017/0188993 A1 Jul. 6, 2017

Related U.S. Application Data

(60) Provisional application No. 62/275,192, filed on Jan. 5, 2016.

(51) Int. Cl.
*A61B 5/08* (2006.01)
*A61B 8/00* (2006.01)
(Continued)

(52) U.S. Cl.
CPC ............ *A61B 8/4218* (2013.01); *A61B 5/024* (2013.01); *A61B 5/4064* (2013.01); *A61B 8/06* (2013.01);
(Continued)

(58) Field of Classification Search
CPC .............................. A61N 1/3676; A61N 1/368
See application file for complete search history.

(56) References Cited

U.S. PATENT DOCUMENTS

| 3,841,308 A | 10/1974 | Tate |
| 3,872,858 A | 3/1975 | Hudson et al. |

(Continued)

FOREIGN PATENT DOCUMENTS

| CN | 104605889 A | 5/2015 |
| EP | 0 403 807 A2 | 12/1990 |

(Continued)

OTHER PUBLICATIONS

Aaslid, R., et al., "Noninvasive transcranial Doppler ultrasound recording of flow velocity in basal cerebral arteries", Journal of Neurosurgery, 1982, 57(6): p. 769-774.

(Continued)

*Primary Examiner* — Michael J D Abreu
(74) *Attorney, Agent, or Firm* — Foley & Lardner LLP

(57) ABSTRACT

According to various embodiments, there is provided a method for determining a neurological condition of a subject using a robotic system. The robotic system includes a transducer. The method includes determining, by a computing system, a first location with respect to a vessel of the subject, the robotic system configured to position the transducer at the first location. The method further includes receiving, by the computing system, a first signal from the vessel in response to the transducer transmitting acoustic energy towards the vessel. The method further includes analyzing, by the computing system, the received first signal to determine a first parameter of blood flow in the vessel. The method further includes determining, by the computing system, the neurological condition of the subject based on the first parameter of the blood flow in the vessel.

29 Claims, 41 Drawing Sheets

(51) Int. Cl.
  *A61B 8/06* (2006.01)
  *A61B 5/00* (2006.01)
  *A61B 8/08* (2006.01)
  *A61B 5/024* (2006.01)
  *A61B 34/30* (2016.01)

(52) U.S. Cl.
  CPC .......... *A61B 8/0808* (2013.01); *A61B 8/4444* (2013.01); *A61B 8/488* (2013.01); *A61B 8/5223* (2013.01); *A61B 8/429* (2013.01); *A61B 8/4227* (2013.01); *A61B 8/4483* (2013.01); *A61B 8/5207* (2013.01); *A61B 34/30* (2016.02)

(56) References Cited

U.S. PATENT DOCUMENTS

| | | |
|---|---|---|
| 4,204,547 A | 5/1980 | Allocca |
| 4,205,687 A | 6/1980 | White et al. |
| 4,413,629 A | 11/1983 | Durley, III |
| 4,483,344 A | 11/1984 | Atkov et al. |
| 4,559,952 A | 12/1985 | Angelsen et al. |
| 4,759,374 A | 7/1988 | Kierney et al. |
| 4,815,705 A | 3/1989 | Kasugai et al. |
| 4,819,648 A | 4/1989 | Ko |
| 4,841,986 A | 6/1989 | Marchbanks |
| 4,930,513 A | 6/1990 | Mayo et al. |
| 4,951,653 A | 8/1990 | Fry et al. |
| 4,984,567 A | 1/1991 | Kageyama et al. |
| 5,040,540 A | 8/1991 | Sackner |
| 5,074,310 A | 12/1991 | Mick |
| 5,094,243 A | 3/1992 | Puy et al. |
| 5,156,152 A | 10/1992 | Yamazaki et al. |
| 5,197,019 A | 3/1993 | Delon-Martin et al. |
| 5,348,015 A | 9/1994 | Moehring et al. |
| 5,379,770 A | 1/1995 | Van Veen |
| 5,388,583 A | 2/1995 | Ragauskas et al. |
| 5,409,005 A | 4/1995 | Bissonnette et al. |
| 5,409,010 A | 4/1995 | Beach et al. |
| 5,411,028 A | 5/1995 | Bonnefous |
| 5,421,565 A | 6/1995 | Harkrader et al. |
| 5,514,146 A | 5/1996 | Lam et al. |
| 5,522,392 A | 6/1996 | Suorsa et al. |
| 5,526,299 A | 6/1996 | Coifman et al. |
| 5,617,873 A | 4/1997 | Yost et al. |
| 5,840,018 A | 11/1998 | Michaeli |
| 5,860,929 A | 1/1999 | Rubin et al. |
| 5,871,445 A | 2/1999 | Bucholz |
| 5,899,864 A | 5/1999 | Arenson et al. |
| 5,919,144 A | 7/1999 | Bridger et al. |
| 5,951,477 A | 9/1999 | Ragauskas et al. |
| 5,993,398 A | 11/1999 | Alperin |
| 6,027,454 A | 2/2000 | Low |
| 6,117,089 A | 9/2000 | Sinha |
| 6,120,446 A | 9/2000 | Ji et al. |
| 6,129,682 A | 10/2000 | Borchert et al. |
| 6,135,957 A | 10/2000 | Cohen-Bacrie et al. |
| 6,139,499 A | 10/2000 | Wilk |
| 6,200,267 B1 | 3/2001 | Burke |
| 6,231,509 B1 | 5/2001 | Johnson et al. |
| 6,261,231 B1 | 7/2001 | Damphousse et al. |
| 6,309,354 B1 | 10/2001 | Madsen et al. |
| 6,358,239 B1 | 3/2002 | Rake et al. |
| 6,364,869 B1 | 4/2002 | Bonaldo |
| 6,387,051 B1 | 5/2002 | Ragauskas et al. |
| 6,403,056 B1 | 6/2002 | Unger |
| 6,413,227 B1 | 7/2002 | Yost et al. |
| 6,423,003 B1 | 7/2002 | Ustuner et al. |
| 6,425,865 B1 | 7/2002 | Salcudean et al. |
| 6,454,715 B2 | 9/2002 | Teo |
| 6,488,717 B1 | 12/2002 | McColl et al. |
| 6,491,647 B1 | 12/2002 | Bridger et al. |
| 6,503,202 B1 | 1/2003 | Hossack et al. |
| 6,547,731 B1 | 4/2003 | Coleman et al. |
| 6,547,734 B2 | 4/2003 | Madsen et al. |
| 6,547,737 B2 | 4/2003 | Njemanze |
| 6,589,189 B2 | 7/2003 | Meyerson et al. |
| 6,618,493 B1 | 9/2003 | Torp et al. |
| 6,627,421 B1 | 9/2003 | Unger et al. |
| 6,653,825 B2 | 11/2003 | Munniksma |
| 6,656,125 B2 | 12/2003 | Misczynski et al. |
| 6,682,488 B2 | 1/2004 | Abend |
| 6,702,743 B2 | 3/2004 | Michaeli |
| 6,716,412 B2 | 4/2004 | Unger |
| 6,740,048 B2 | 5/2004 | Yost et al. |
| 6,746,422 B1 | 6/2004 | Noriega et al. |
| 6,875,176 B2 | 4/2005 | Mourad et al. |
| 6,887,199 B2 | 5/2005 | Bridger et al. |
| 6,955,648 B2 | 10/2005 | Mozayeni et al. |
| 7,122,007 B2 | 10/2006 | Querfurth |
| 7,128,713 B2 | 10/2006 | Moehring et al. |
| 7,147,605 B2 | 12/2006 | Ragauskas |
| 7,302,064 B2 | 11/2007 | Causevic et al. |
| 7,338,450 B2 | 3/2008 | Kristoffersen et al. |
| 7,403,805 B2 | 7/2008 | Abreu |
| 7,452,551 B1 | 11/2008 | Unger et al. |
| 7,534,209 B2 | 5/2009 | Abend et al. |
| 7,537,568 B2 | 5/2009 | Moehring |
| D594,127 S | 6/2009 | Causevic et al. |
| 7,547,283 B2 | 6/2009 | Mourad et al. |
| D603,051 S | 10/2009 | Causevic et al. |
| 7,674,229 B2 | 3/2010 | Hynynen et al. |
| 7,720,530 B2 | 5/2010 | Causevic |
| 7,771,358 B2 | 8/2010 | Moehring et al. |
| 7,815,574 B2 | 10/2010 | Mourad et al. |
| 7,854,701 B2 | 12/2010 | Stergiopoulos et al. |
| 7,857,763 B2 | 12/2010 | Tai |
| 7,904,144 B2 | 3/2011 | Causevic et al. |
| 7,912,269 B2 | 3/2011 | Ikeda et al. |
| 7,938,780 B2 | 5/2011 | Ragauskas et al. |
| 7,942,820 B2 | 5/2011 | Njemanze |
| D641,886 S | 7/2011 | Causevic et al. |
| 7,998,075 B2 | 8/2011 | Ragauskas et al. |
| RE42,803 E | 10/2011 | Lipson et al. |
| 8,036,856 B2 | 10/2011 | Pan et al. |
| 8,041,136 B2 | 10/2011 | Causevic |
| 8,062,224 B2 | 11/2011 | Ragauskas et al. |
| 8,075,488 B2 | 12/2011 | Burton |
| 8,109,880 B1 | 2/2012 | Pranevicius et al. |
| 8,162,837 B2 | 4/2012 | Moehring et al. |
| 8,206,303 B2 | 6/2012 | Ragauskas et al. |
| 8,211,023 B2 | 7/2012 | Swan et al. |
| 8,235,907 B2 | 8/2012 | Wilk et al. |
| 8,254,654 B2 | 8/2012 | Yen et al. |
| 8,265,291 B2 | 9/2012 | Bridger et al. |
| 8,353,853 B1 | 1/2013 | Kyle et al. |
| 8,364,254 B2 | 1/2013 | Jacquin et al. |
| 8,364,255 B2 | 1/2013 | Isenhart et al. |
| 8,366,627 B2 | 2/2013 | Kashif et al. |
| 8,391,948 B2 | 3/2013 | Causevic et al. |
| 8,394,024 B2 | 3/2013 | Miyama et al. |
| 8,394,025 B2 | 3/2013 | Ragauskas et al. |
| 8,414,539 B1 | 4/2013 | Kuracina et al. |
| 8,453,509 B2 | 6/2013 | Oberdorfer et al. |
| 8,473,024 B2 | 6/2013 | Causevic et al. |
| 8,603,014 B2 | 12/2013 | Alleman et al. |
| 8,613,714 B2 | 12/2013 | Alleman et al. |
| 8,622,912 B2 | 1/2014 | Chin et al. |
| 8,647,278 B2 | 2/2014 | Ji et al. |
| 8,706,205 B2 | 4/2014 | Shahaf et al. |
| 8,834,376 B2 | 9/2014 | Stergiopoulos et al. |
| 8,905,932 B2 | 12/2014 | Lovoi et al. |
| 8,926,515 B2 | 1/2015 | Ragauskas et al. |
| 8,998,818 B2 | 4/2015 | Pranevicius et al. |
| 9,005,126 B2 | 4/2015 | Beach et al. |
| 9,028,416 B2 | 5/2015 | De Viterbo |
| 9,042,201 B2 | 5/2015 | Tyler et al. |
| 9,066,679 B2 | 6/2015 | Beach et al. |
| 9,125,616 B2 | 9/2015 | Bredno et al. |
| 9,138,154 B2 | 9/2015 | Weinberg et al. |
| 9,192,359 B2 | 11/2015 | Flynn et al. |
| 9,196,037 B2 | 11/2015 | Jung |
| 9,630,028 B2 | 4/2017 | Browning et al. |
| RE46,614 E | 11/2017 | Lipson et al. |

(56) References Cited

U.S. PATENT DOCUMENTS

| | | |
|---|---|---|
| 2001/0053879 A1 | 12/2001 | Mills et al. |
| 2002/0103436 A1 | 8/2002 | Njemanze |
| 2003/0050607 A1 | 3/2003 | Gagnieux et al. |
| 2004/0267127 A1 | 12/2004 | Abend et al. |
| 2005/0004457 A1 | 1/2005 | Moilanen et al. |
| 2005/0004468 A1 | 1/2005 | Abend et al. |
| 2005/0015009 A1* | 1/2005 | Mourad et al. |
| 2005/0049515 A1 | 3/2005 | Misczynski et al. |
| 2005/0119573 A1 | 6/2005 | Vilenkin et al. |
| 2005/0124901 A1 | 6/2005 | Misczynski et al. |
| 2005/0147297 A1 | 7/2005 | McLaughlin et al. |
| 2005/0148895 A1 | 7/2005 | Misczynski et al. |
| 2006/0025801 A1 | 2/2006 | Lulo et al. |
| 2006/0030777 A1 | 2/2006 | Liang et al. |
| 2006/0049721 A1 | 3/2006 | Kuehnicke |
| 2006/0173307 A1 | 8/2006 | Amara et al. |
| 2006/0173337 A1 | 8/2006 | Chen et al. |
| 2006/0184070 A1 | 8/2006 | Hansmann et al. |
| 2006/0206037 A1 | 9/2006 | Braxton |
| 2006/0241462 A1 | 10/2006 | Chou et al. |
| 2007/0016046 A1 | 1/2007 | Mozayeni et al. |
| 2007/0016050 A1 | 1/2007 | Moehring et al. |
| 2007/0078345 A1 | 4/2007 | Mo et al. |
| 2007/0161891 A1 | 7/2007 | Moore et al. |
| 2007/0232918 A1 | 10/2007 | Taylor |
| 2007/0239019 A1 | 10/2007 | Richard et al. |
| 2007/0244398 A1 | 10/2007 | Lo et al. |
| 2008/0015478 A1 | 1/2008 | Bose |
| 2008/0058861 A1 | 3/2008 | Cooper et al. |
| 2008/0065099 A1 | 3/2008 | Cooper et al. |
| 2008/0132790 A1 | 6/2008 | Burton |
| 2008/0208060 A1 | 8/2008 | Murkin |
| 2008/0262350 A1 | 10/2008 | Unger |
| 2009/0062813 A1 | 3/2009 | Prisco et al. |
| 2009/0074151 A1 | 3/2009 | Henderson et al. |
| 2009/0198137 A1 | 8/2009 | Ragauskas et al. |
| 2009/0264786 A1 | 10/2009 | Jacquin |
| 2009/0275836 A1 | 11/2009 | Fujii et al. |
| 2009/0287084 A1 | 11/2009 | Ragauskas et al. |
| 2009/0306515 A1 | 12/2009 | Matsumura et al. |
| 2009/0326379 A1 | 12/2009 | Daigle et al. |
| 2010/0016707 A1 | 1/2010 | Amara et al. |
| 2010/0069757 A1 | 3/2010 | Yoshikawa et al. |
| 2010/0081893 A1 | 4/2010 | Jarvik et al. |
| 2010/0087728 A1 | 4/2010 | Jarvik et al. |
| 2010/0121192 A1 | 5/2010 | Nogata et al. |
| 2010/0125206 A1 | 5/2010 | Syme |
| 2010/0130866 A1 | 5/2010 | Main et al. |
| 2010/0274303 A1 | 10/2010 | Bukhman |
| 2010/0298821 A1 | 11/2010 | Garbagnati |
| 2011/0112426 A1 | 5/2011 | Causevic |
| 2011/0137182 A1 | 6/2011 | Bellezza et al. |
| 2011/0144518 A1 | 6/2011 | Causevic |
| 2011/0251489 A1 | 10/2011 | Zhang et al. |
| 2011/0275936 A1 | 11/2011 | Cho et al. |
| 2011/0301461 A1 | 12/2011 | Anite |
| 2012/0108967 A1 | 5/2012 | Weng et al. |
| 2012/0108972 A1 | 5/2012 | Miyama et al. |
| 2012/0123272 A1 | 5/2012 | Lam et al. |
| 2012/0123590 A1 | 5/2012 | Halsmer |
| 2012/0153580 A1 | 6/2012 | Soma |
| 2012/0157840 A1 | 6/2012 | Syme |
| 2012/0165675 A1 | 6/2012 | Syme |
| 2012/0165676 A1 | 6/2012 | Njemanze |
| 2012/0226163 A1 | 9/2012 | Moehring et al. |
| 2012/0238875 A1 | 9/2012 | Savitsky et al. |
| 2013/0006106 A1 | 1/2013 | O'Reilly et al. |
| 2013/0018277 A1 | 1/2013 | Liu |
| 2013/0047452 A1 | 2/2013 | McMurtry et al. |
| 2013/0080127 A1 | 3/2013 | Shahaf et al. |
| 2013/0197401 A1 | 8/2013 | Sato et al. |
| 2013/0239687 A1 | 9/2013 | Nakabayashi |
| 2013/0274607 A1 | 10/2013 | Anand et al. |
| 2014/0031690 A1 | 1/2014 | Toji et al. |
| 2014/0031693 A1 | 1/2014 | Solek |
| 2014/0081142 A1 | 3/2014 | Toma et al. |
| 2014/0081144 A1 | 3/2014 | Moehring et al. |
| 2014/0094701 A1 | 4/2014 | Kwartowitz et al. |
| 2014/0163328 A1 | 6/2014 | Geva et al. |
| 2014/0163379 A1 | 6/2014 | Bukhman |
| 2014/0171820 A1 | 6/2014 | Causevic |
| 2014/0194740 A1 | 7/2014 | Stein et al. |
| 2014/0276059 A1 | 9/2014 | Sheehan |
| 2014/0316269 A1 | 10/2014 | Zhang et al. |
| 2014/0323857 A1 | 10/2014 | Mourad et al. |
| 2014/0343431 A1 | 11/2014 | Vajinepalli et al. |
| 2015/0051489 A1 | 2/2015 | Caluser et al. |
| 2015/0065871 A1 | 3/2015 | Konofagou et al. |
| 2015/0065916 A1 | 3/2015 | Maguire et al. |
| 2015/0094582 A1 | 4/2015 | Tanaka et al. |
| 2015/0151142 A1 | 6/2015 | Tyler et al. |
| 2015/0157266 A1 | 6/2015 | Machon et al. |
| 2015/0190111 A1 | 7/2015 | Fry |
| 2015/0216500 A1 | 8/2015 | Mano et al. |
| 2015/0245771 A1 | 9/2015 | Wang et al. |
| 2015/0245776 A1 | 9/2015 | Hirohata et al. |
| 2015/0245820 A1 | 9/2015 | Tamada |
| 2015/0250446 A1 | 9/2015 | Kanayama |
| 2015/0250448 A1 | 9/2015 | Tamada |
| 2015/0297176 A1 | 10/2015 | Rincker et al. |
| 2015/0297177 A1 | 10/2015 | Boctor et al. |
| 2015/0302584 A1 | 10/2015 | Brauner et al. |
| 2015/0351718 A1 | 12/2015 | Vollmer et al. |
| 2015/0356734 A1 | 12/2015 | Ooga et al. |
| 2015/0359448 A1 | 12/2015 | Beach |
| 2016/0000367 A1 | 1/2016 | Lyon |
| 2016/0000411 A1 | 1/2016 | Raju et al. |
| 2016/0000516 A1 | 1/2016 | Cheng et al. |
| 2016/0030001 A1 | 2/2016 | Stein et al. |
| 2016/0094115 A1 | 3/2016 | Okawa et al. |
| 2016/0151618 A1 | 6/2016 | Powers et al. |
| 2016/0256130 A1 | 9/2016 | Hamilton et al. |
| 2016/0278736 A1 | 9/2016 | Hamilton et al. |
| 2016/0310006 A1 | 10/2016 | Aguero Villarreal et al. |
| 2016/0310023 A1 | 10/2016 | Chachisvilis et al. |
| 2016/0317129 A1 | 11/2016 | Seip et al. |
| 2016/0324585 A1 | 11/2016 | Noonan et al. |
| 2016/0367217 A1 | 12/2016 | Flores et al. |
| 2017/0119347 A1 | 5/2017 | Flores et al. |
| 2017/0188992 A1 | 7/2017 | O'Brien et al. |
| 2017/0188993 A1 | 7/2017 | Hamilton et al. |
| 2017/0188994 A1 | 7/2017 | Flores et al. |
| 2017/0196465 A1 | 7/2017 | Browning et al. |
| 2017/0307420 A1 | 10/2017 | Flores et al. |
| 2018/0021021 A1 | 1/2018 | Zwierstra et al. |
| 2018/0093077 A1 | 4/2018 | Harding et al. |
| 2018/0103927 A1 | 4/2018 | Chung et al. |
| 2018/0103928 A1 | 4/2018 | Costa et al. |
| 2018/0177487 A1 | 6/2018 | Deffieux et al. |
| 2018/0214124 A1 | 8/2018 | O'Brien et al. |
| 2018/0220991 A1 | 8/2018 | O'Brien et al. |
| 2019/0150895 A1 | 5/2019 | Tian et al. |

FOREIGN PATENT DOCUMENTS

| | | | |
|---|---|---|---|
| EP | 1750804 B1 * | 7/2008 | ......... A61B 18/1492 |
| EP | 2 034 901 | 3/2009 | |
| EP | 2 111 787 | 10/2009 | |
| EP | 2 858 619 | 4/2015 | |
| FR | 2606625 A1 | 5/1988 | |
| JP | S52-126979 A | 10/1977 | |
| JP | H02-114008 | 4/1990 | |
| JP | H05-143161 | 6/1993 | |
| JP | H571763 U | 9/1993 | |
| JP | 07-299066 A | 11/1995 | |
| JP | 10-328189 A | 12/1998 | |
| JP | 2003-225239 A | 8/2003 | |
| JP | 2003-230558 A | 8/2003 | |
| JP | 2003-245280 A | 9/2003 | |
| JP | 2004-237082 A | 8/2004 | |
| JP | 2006-025904 A | 2/2006 | |
| JP | 2007-143704 A | 6/2007 | |
| JP | 2010-500084 A | 1/2010 | |
| JP | 2010-200844 A | 9/2010 | |

(56) References Cited

FOREIGN PATENT DOCUMENTS

| | | |
|---|---|---|
| JP | 2013-503681 A | 2/2013 |
| JP | 2015-533299 A | 11/2015 |
| WO | WO-95/02361 | 1/1995 |
| WO | WO-99/56625 | 11/1999 |
| WO | WO-2009/138882 A2 | 11/2009 |
| WO | WO-2010/042146 | 4/2010 |
| WO | WO-2013/155537 | 10/2013 |
| WO | WO-2014/070993 A1 | 5/2014 |
| WO | WO-2015/073903 A1 | 5/2015 |
| WO | WO-2015/092604 | 6/2015 |
| WO | WO-2016/001548 | 1/2016 |

OTHER PUBLICATIONS

Baldwin, K., et al., "Subpeak Regional Analysis of Intracranial Pressure Waveform Morphology based on Cerebrospinal Fluid Hydrodynamics in the Cerebral Aqueduct and Prepontine Cistern", 34th Annual International Conference of the IEEE EMBS, 2012, p. 3935-3938.

Bashford, G., et al.,"Monitoring Cerebral Hemodynamics with Transcranial Doppler Ultrasound during Cognitive and Exercise Testing in Adults following Unilateral Stroke", 34th Annual International Conference of the IEEE EMBS, 2012, p. 2310-2313.

Chen, W., et al., "Intracranial Pressure Level Prediction in Traumatic Brain Injury by Extracting Features from Multiple Sources and Using Machine Learning Methods", 2010 IEEE International Conference on Bioinformatics and Biomedicine, 2010, p. 510-515.

Cheng, Y. & Zhao, R., "Self-training classifier via local learning regularization", Proceedings of the Eighth International Conference on Machine Learning and Cybernetics, 2009, p. 454-459.

Ekroth, R., et al., "Transcranial Doppler-estimated versus thermodilution estimated cerebral blood flow during cardiac operations. Influence of temperature and arterial carbon dioxide tension." Journal Thoracic Cardiovascular Surgery, 1991, 102(1): p. 95-102.

Extended European Search Report dated Jan. 4, 2019, from application No. 16812644.9.

Final Office Action dated Jan. 28, 2019, from U.S. Appl. No. 15/942,368.

Gomez, C., et al., Transcranial Doppler Ultrasonographic Assessment of Intermittent Light Stimulation at Different Frequencies, Stroke, 1990, 21, p. 1746-1748.

Harrison, M. & Markus, H., "Estimation of cerebrovascular reactivity using transcranial Doppler, including the use of breath-holding as the vasodilatory stimulus", Stroke, 1992, 23(5) p. 668-73.

International Preliminary Report on Patentability dated Nov. 8, 2018, from application No. PCT/US2017/029483.

Jaffres, P., et al., "Transcranial Doppler to detection admission patients at risk for neurological deterioration following mild and moderate brain trauma", Intensive Care Med, 2005, 31 (6): p. 785-790.

Japanese Decision of Rejection dated Dec. 18, 2018, from application No. 2016-554529.

Japanese Office Action dated Aug. 28, 2018, from application No. 2016-554529.

Len, T.K., et al., "Cerebrovascular reactivity impairment after sport-induced concussion", Med Sci Sports Exerc, 2011, 43(12): p. 2241-2248.

Non-Final Office Action dated Sep. 17, 2018, from U.S. Appl. No. 15/156,175.

Uguz, H., "A hybrid system based on information gain and principal component analysis for the classification of transcranial Doppler signals", Computer Methods and Programs in Biomedicine, 2010, 107(2012) p. 598-609.

Zhu, X., "Semi-supervised Learning Literature Survey", Computer Sciences TR 1530, University of Wisconsin—Madison, 2008.

International Search Report and Written Opinion dated May 4, 2017, from application No. PCT/US2017/012395.

M.H. Raibert et al., "Hybrid Position/Force Control of Manipulators", Journal of Dynamic Systems, Measurement, and Control, vol. 102, Jun. 1981, pp. 126-133, abstract.

Final Office Action dated Aug. 2, 2019, from U.S. Appl. No. 15/399,648.

Final Office Action dated Aug. 28, 2019, from U.S. Appl. No. 15/399,440.

Non-Final Office Action dated Aug. 14, 2019, from U.S. Appl. No. 15/497,039.

International Search Report and Written Opinion dated Oct. 13, 2016, from related international application No. PCT/US2016/038433.

International Search Report and Written Opinion dated Jun. 1, 2017, from application No. PCT/IB2017/050349.

International Search Report and Written Opinion dated Jun. 8, 2017, from application No. PCT/US2017/012402.

Tatasurya, Samuel Radiant, "Multimodal Graphical User Interface for Ultrasound Machine Control via da Vinci Surgeon Console: Design, Development, and Initial Evaluation," The University of British Columbia, Vancouver, Aug. 2015, p. 33, paragraph 1.

International Search Report and Written Opinion dated Aug. 14, 2017, from international application No. PCT/US2017/029483.

Non-Final Office Action dated Apr. 2, 2019, from U.S. Appl. No. 15/399,440.

Non-Final Office Action dated Mar. 19, 2019, from U.S. Appl. No. 15/399,648.

Non-Final Office Action dated Oct. 1, 2019, from U.S. Appl. No. 15/399,735.

Chatelain et al. "Confidence-Driven Control of an Ultrasound Probe: Target-Specific Acoustic Window Optimization." IEEE ICRA May 16-21, 2016, pp. 3441-3446.

Chatelain et al. "Optimization of ultrasound image quality via visual servoing." IEEE INCRA May 26-30, 2015, pp. 5997-6002.

International Preliminary Report on Patentability dated Dec. 28, 2017, from international application No. PCT/US2016/038433.

International Preliminary Report on Patentability dated Jul. 19, 2018, from application No. PCT/IB2017/050349.

International Preliminary Report on Patentability dated Jul. 19, 2018, from application No. PCT/US2017/012365.

International Preliminary Report on Patentability dated Jul. 19, 2018, from application No. PCT/US2017/012395.

International Preliminary Report on Patentability dated Jul. 19, 2018, from application No. PCT/US2017/012402.

Japanese Office Action dated Apr. 24, 2018, from application No. 2016-554529.

Mackinnon et al. "Long-Term Ambulatory Monitoring for Cerebral Emboli Using Transcranial Doppler Ultrasound." Stroke(35), 2004; pp. 73-78.

Nadeau et al. "Intensity-Based Ultrasound Visual Servoing: Modeling and Validation with 2-D and 3-D Probes." IEEE Trans on Robotics (29:4), Aug. 2013, pp. 1003-1015.

Non-Final Office Action dated Jun. 27, 2018, from U.S. Appl. No. 15/942,368.

Qiu et al, "A Robotic Holder of Transcranial Doppler Probe for CBFV Auto-Searching." Proc of IEEE ICIA, Aug. 2013, pp. 1284-1289.

Souza-Daw et al. "Towards Ultrasonic Detection of Acoustic Windows for Transcranial Doppler Ultrasound and related Procedures." IEEE Proc INDS'11 & ISTET'11. Jul. 25-27, 2011. 6 pages.

Extended European Search Report dated Jul. 16, 2019, from application No. 17736353.8.

Extended European Search Report dated Jul. 19, 2019, from application No. 17736375.1.

Extended European Search Report dated Jul. 24, 2019, from application No. 17735919.7.

Ni, et al., "Serial Transcranial Doppler Sonography in Ischemic Strokes in Middle Cerebral Artery Territory", Journal of Neruoimaging, Oct. 1, 1994, pp. 232-236.

Final Office Action dated Jun. 9, 2020, from U.S. Appl. No. 15/399,648.

Extended European Search Report dated Nov. 12, 2019, from application No. 17736371.0.

(56) References Cited

OTHER PUBLICATIONS

Extended European Search Report dated Nov. 21, 2019, from application No. 17790294.7.
Japanese Office Action dated Jan. 27, 2020, from application No. 2018-534127.
Qiu, et al., "A Robotic Holder of Transcranial Doppler Probe for CBFV Auto-Searching", 2013 IEEE International Conference on Information and Automation (ICIA), IEEE, Aug. 26, 2013, pp. 1284-1289.
Final Office Action dated Jan. 30, 2020, from U.S. Appl. No. 15/497,039.
Non-Final Office Action dated Nov. 19, 2019, from U.S. Appl. No. 15/399,648.
Notice of Allowance dated Dec. 9, 2019, from U.S. Appl. No. 15/399,440.
Chinese Office Action dated Mar. 24, 2020, application serial No. 201680034144.6.
Notice of Allowance dated Mar. 4, 2020, from U.S. Appl. No. 15/942,368.
Chinese Office Action dated Sep. 23, 2020, from application No. 201780005865.9.
Japanese Office Action dated Dec. 10, 2020, from application No. 2018-534916.
Japanese Office Action dated Nov. 5, 2020, from application No. 2018-534904.
Japanese Office Action dated Oct. 22, 2020, from application No. 2018-534131.
Final Office Action dated Jun. 15, 2020, from U.S. Appl. No. 15/399,735.
Chinese Office Action dated Aug. 27, 2020, from application No. 201780005528.X.
Chinese Office Action dated Aug. 18, 2020, from application No. 201780005508.2.
Chinese Office Action dated Jun. 30, 2020, from application No. 201780005447.X.
Non-Final Office Action dated Oct. 28, 2020, from U.S. Appl. No. 15/187,397.
Non-Final Office Action dated Jul. 16, 2020, from U.S. Appl. No. 15/497,039.
Japanese Office Action dated Mar. 11, 2021, from application No. 2018-555541.
Final Office Action dated Apr. 23, 2021, from U.S. Appl. No. 15/187,397.

* cited by examiner

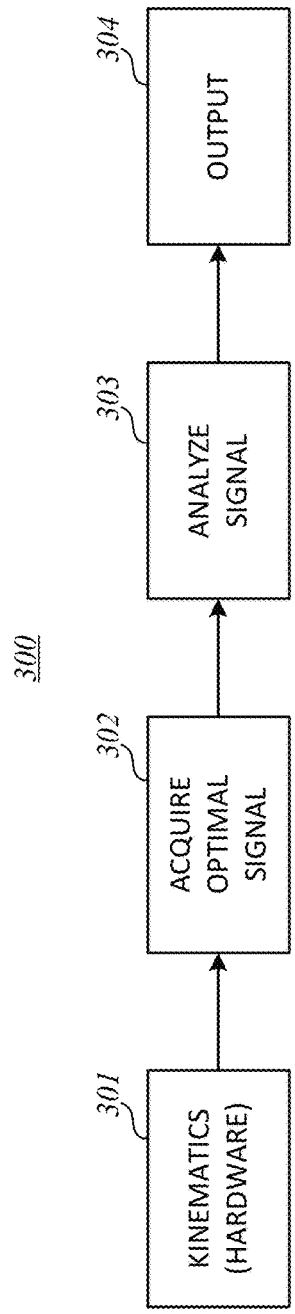
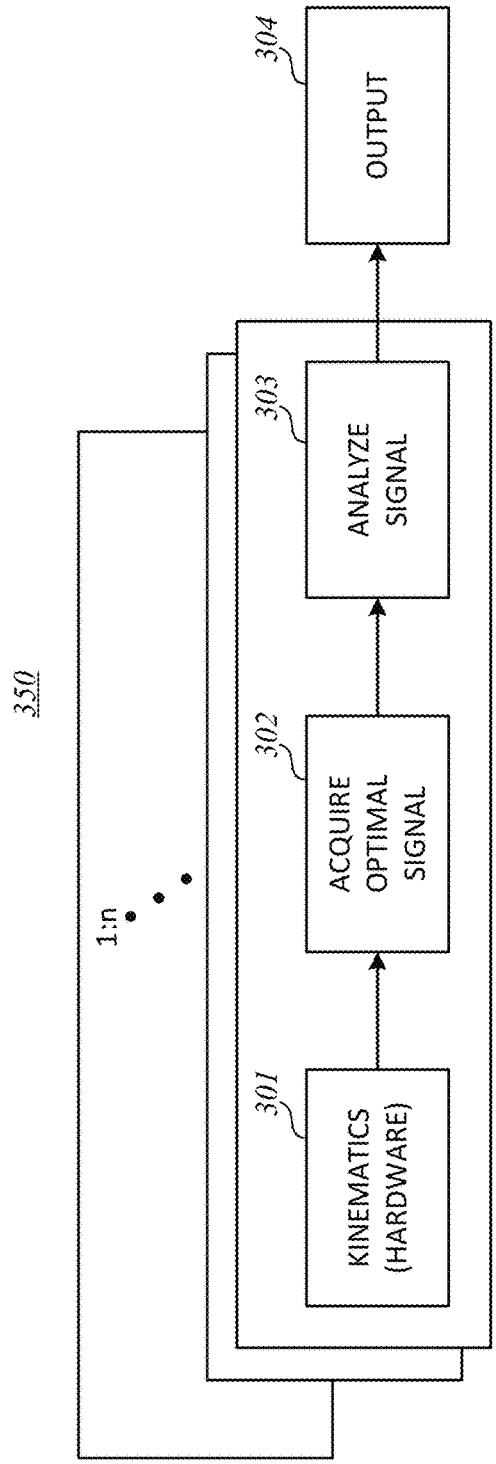
Fig. 3A
Fig. 3B

SYSTEMS AND METHODS FOR DETERMINING CLINICAL INDICATIONS

CROSS-REFERENCE TO RELATED APPLICATIONS

This application claims the benefit of and priority to U.S. Provisional Application No. 62/275,192, filed Jan. 5, 2016, the contents of which are incorporated herein by reference in their entireties.

BACKGROUND

1. Field

Subject matter described herein relates generally to systems and method for determining clinical indications.

2. Background

Neurological conditions such as traumatic brain injury (TBI), stroke, dementia/Alzheimer's Disease, Parkinson's disease, depression, and others affect millions of patients each year worldwide. However, acquiring cerebral blood flow velocity (CBFV) signals using ultrasound requires placement of a transducer within a specific region of the skull thin enough for the waves to penetrate, locating a signal of the artery of interest, and maintaining a steady position for sufficient measurements, which can be very difficult to perform by technicians. Additionally, reading and interpreting the scans once complete is difficult because subtle features and changes in the CBFV waveform that indicate neurological disorders are not easily discernable using traditional analysis or visual inspection.

BRIEF DESCRIPTION OF FIGURES

FIG. 3A illustrates a high-level flow diagram of operation of a system for determining neurological conditions according to some embodiments.

FIG. 3B illustrates a high-level flow diagram of operation of a system for determining neurological conditions according to some embodiments.

DETAILED DESCRIPTION

Figure 1A:
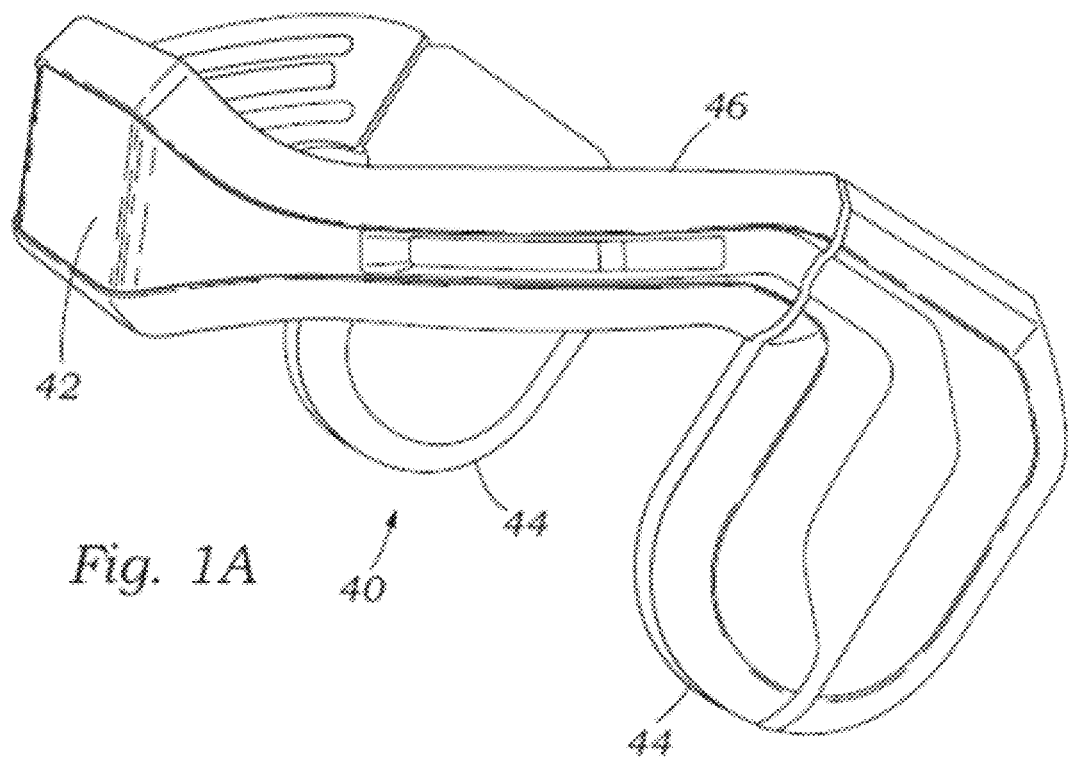
FIG. 1A, FIG. 1B, and FIG. 1C illustrate an automated headset for determining neurological conditions according to some embodiments.

Neurological conditions such as traumatic brain injury (TBI), stroke, dementia/Alzheimer's Disease, Parkinson's disease, depression, and others affect millions of patients each year worldwide. Transcranial Doppler (TCD) ultrasound is currently used in major hospitals for the assessment of cerebral hemodynamics within the Circle of Willis arteries and other major conducting arteries or veins (carotid artery, middle cerebral artery, ophthalmic artery, jugular vein, and others). However, acquiring the cerebral blood flow velocity (CBFV) signals using TCD requires placement of a transducer within a specific region of the skull thin enough for the ultrasound waves to penetrate, locating a signal of the artery of interest, and maintaining a steady position for sufficient measurements. The location of these narrow windows varies significantly from person to person. Additionally, reading and interpreting the scans once complete is difficult because subtle features and changes in the CBFV waveform that indicate neurological disorders are not easily discernable using traditional TCD analysis or visual inspection. These requirements make insonating (i.e., exposing to ultrasound) the desired blood vessel difficult, thereby restricting TCD use to major hospitals with expensive, on staff expert human sonographers to operate the device as well as reducing the overall utility of the device through utilization of only simple analysis.

As such, there is a need for developing a system for accurately and precisely interpreting and analyzing waveforms acquired from scanning vessels within the brain (e.g., using TCD), and determining a neurological condition based on the analyzed waveforms. In particular, there is a need for an automated TCD ultrasound system that can implement fine positioning and steady placement of a signal transducer and that can measure and interpret the resulting blood flow waveforms and subtle changes within them. Additionally, a real-time or semi-real time map or visualization of the major conducting arteries or veins of the brain will provide valuable information to clinicians for further analysis. According to various embodiments, the deployment of an automated system for the quantification of cerebral hemodynamics would have a dramatic impact on several neurological indications or conditions including but not limited to, stroke, mild (concussion) and severe TBI, dementia, and others. For example, in some embodiments, detection of a large vessel occlusion (LVO), a type of serious stroke, by observing cerebral blood flow (CBF) information (e.g., CBFV) may be possible by an automated system. Similarly, in some embodiments, patients with a TBI or dementia may exhibit small variations in CBF that traditional TCD analysis is unable to recognize, but can be detected and analyzed by an automated device such that objective physiological information (e.g., CBF) can be used for a diagnosis or management of said condition.

Accordingly, in various embodiments, an automated system can be paired with a decision support and analysis framework capable of extending TCD to the aforementioned neurological conditions through the analysis of the CBFV waveform. As such, various embodiments described herein provide, in diagnosing one or more neurological conditions, systems and methods including automation (e.g., robotics) configured to optimally position a device within a narrow window adjacent the brain for optimal signal reception, interpretation of the received CBFV/cerebral hemodynamic data signals through waveform analysis, and visualization or mapping of some, or all the vasculature of the brain. Various embodiments described herein further provide an automated solution that can quantify subtle changes in the cerebral vasculature, and address the technical limitations by automatically acquiring the signal of interest and interpreting the measured information so there is an actionable output.

Figure 1B:
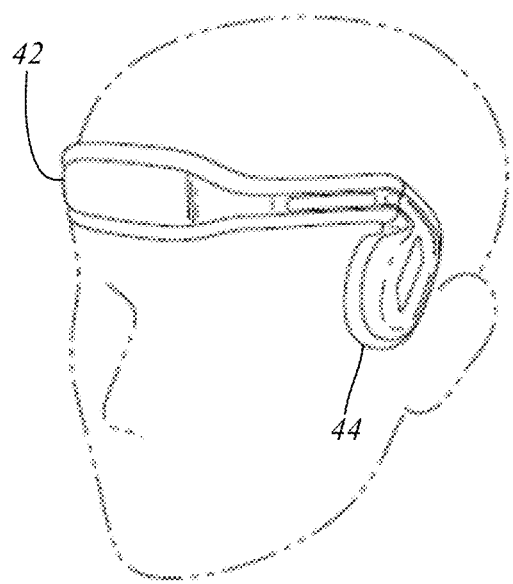
Figure 1C:
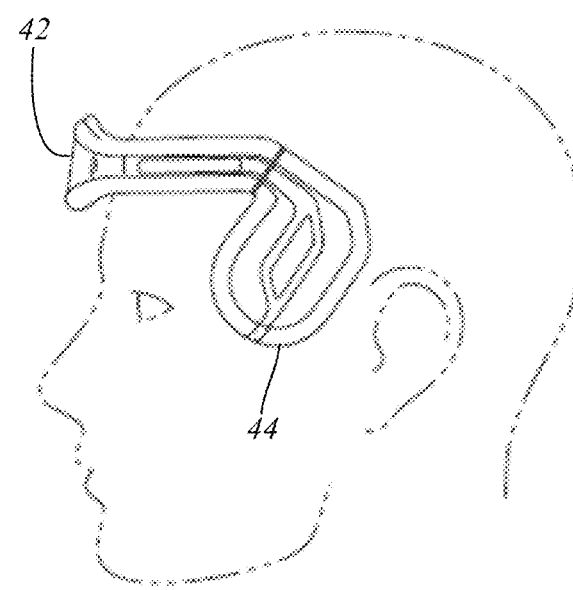

FIGS. 1A-1C show an automated TCD headset 40 having a display screen 42 on the front thereof. More particularly, the headset 40 includes dual ultrasound probes 44 on the sides and a headband 46 that extends around the front so as to connect the two probes. As seen in FIGS. 1A-1C the TCD headset 40 fits over the cranium of a patient with the probes 44 located at either temple. The probes 44 include TCD scanners therein that can auto locate the middle cerebral artery (MCA). Desirably, the headband 46 is elastic in nature and enables the headset 40 to fit snugly over the front of the head of a variety of different head sizes so that the inner face of the probes 44 makes good contact with the temples. A lubricating gel is preferably used to improve acoustic transmission.

Figure 2:
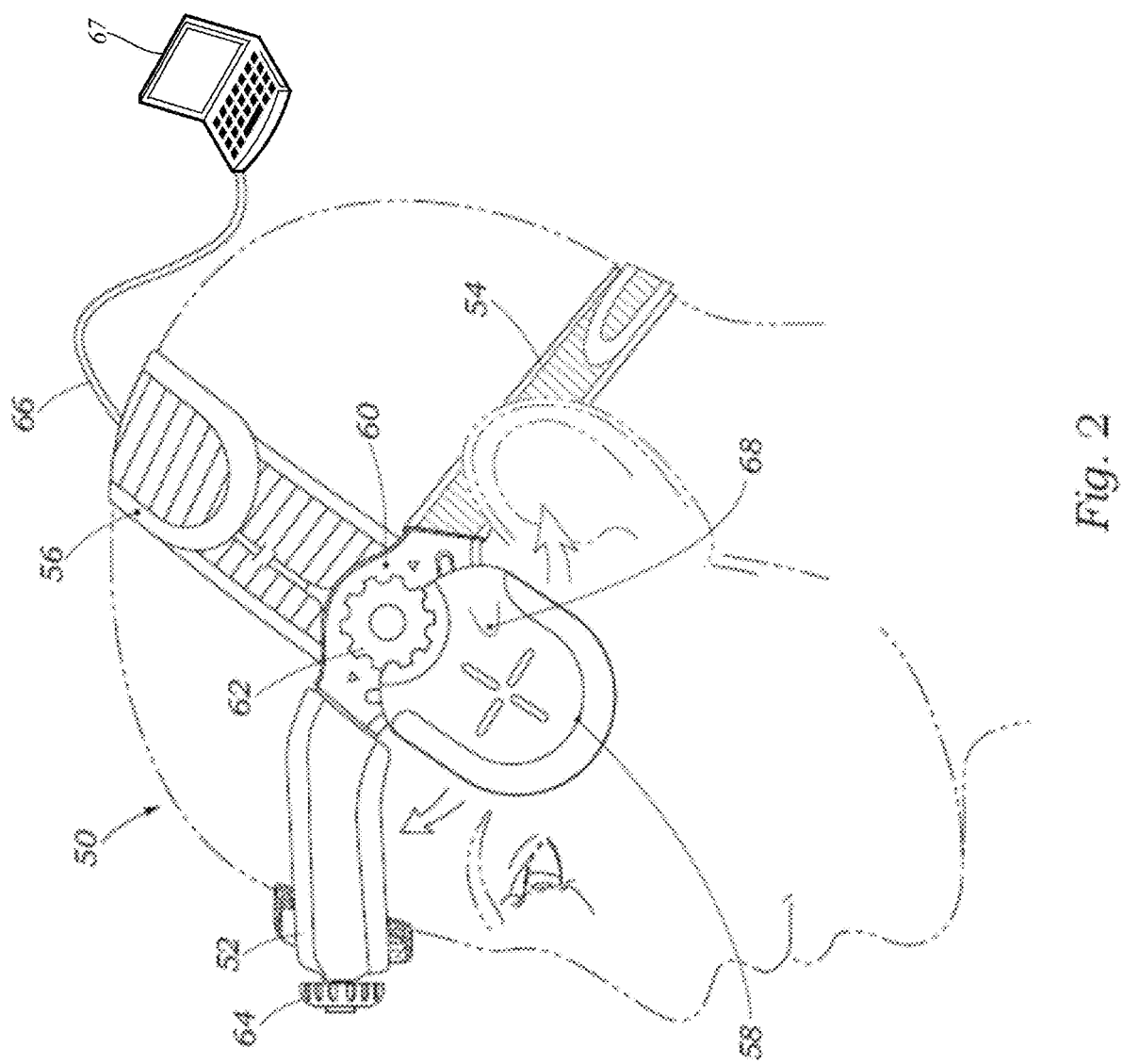
FIG. 2 illustrates a side view of an automated headset for determining neurological conditions according to some embodiments.

FIG. 2 is a side view of another exemplary TCD headset 50 worn by a patient and having a forehead strap 52, a rear strap 54, and a cranial strap 56. The straps 52, 54, 56 help secure the headset 50 on the head, and in particular ensure good contact of a pair of reciprocating TCD scanners 58 with either temple. The TCD scanners 58 mount for reciprocal forward and backward rotation, as indicated by the movement arrows, to a junction member 60 at the intersection of the three straps 52, 54, 56. In one embodiment, the TCD scanners 58 rotate about 60° in each direction about a Z-axis perpendicular to the XY scan plane. Although not shown, a small motor within the junction member 60 enables movement of the scanners 58.

The system of the three straps 52, 54, 56 is effective in holding the headset 50 in place. The cranial strap 56 includes a Velcro break for adjustability, the rear strap 54 is desirably elastic, and a pair of tightening knobs 62 on each junction member 60 and a tightening knob 64 at the middle of the forehead strap 52 enable fine adjustment of the position of the scanners 58 for X-Y calibration. The cranial strap 56 helps limit migration of the headset 50 once secured due to movement of the jaw and associated muscles.

In some embodiments, a cable 66 may be attached to the junction members 60 for connection to a control unit such as computer 67, a tablet computer (not shown for clarity), or any other type of computing device, or the system may communicate wirelessly with a computing device. The computer 67, or other connected computing device provides processing to receive and process data returned from ultrasound probes 44.

Each scanner 58 desirably includes an injection port 68, preferably formed by an indent leading to a channel, for introduction of a lubricating gel to the inside contact surfaces. This injection port 68 helps reduce a messy application of the gel. In a preferred embodiment, the TCD sensor on the inside of each scanner 58 may be displaced in the Z-direction, or toward and away from the temple, to optimize acoustic contact.

One approach to investigate the underlying physiology of mild TBI is to provide a stimulus to exacerbate changes in the cerebrovasculature and use the described framework to more accurately quantify the changes. Stimulus can be provided in a variety of different ways including changes in arterial blood pressure (exercise, leg cuff, pharmaceuticals, etc.), changes in concentrations of carbon dioxide (CO2) in the arterial blood supply, or local by altering metabolism in specific area of the brain (i.e. flashing lights stimulates the occipital lobe).

In one technique, the cerebrovascular bed is extremely sensitive to changes in arterial blood concentrations of $CO_2$ ($PaCO_2$). Increased arterial $CO_2$ levels (such as from holding one's breath) cause arteriolar vasodilatation resulting in increased velocity in the upstream large cerebral arteries due to increased cerebral blood flow. Conversely, a decreased $CO_2$ (via hyperventilation) results in decreased CBFV due to arteriolar vasoconstriction causing a reduction in CBF.

Cerebrovascular reactivity (CVR) describes the changes in CBFV due to changes in the $PaCO_2$. The goal of CVR testing is to assess the vasodilatory or vasoconstrictory capacity of the resistance arterioles of the brain and has been shown to be impaired after a severe TBI, migraine, long-term spaceflight, stroke, and carotid artery stenosis. More recently, CVR has shown potential as marker of physiologic dysfunction in mild TBI. Both concussion and control subjects were studied using breath holding and hyperventilation to investigate CVR. Similarly to exercise being shown as a physiological stress to elucidate changes in concussion patients, alterations in mean CBFV dynamics from repeated breath holding and hyperventilation have also been shown. However, CBFV data is sampled at 1 Hz, removing all morphological information from the analysis. In some embodiments, the CVR testing is expanded to look at the effect on not just the mean velocity, but the entire shape of the CBFV waveform. The patient may be asked to hold his or her breath to raise $CO_2$ levels and the CBFV may be monitored. Conversely, the patient may be asked to hyperventilate to lower $CO_2$ levels and the CBFV may be monitored. Looking at CVR using only mean velocity may provide an incomplete picture.

FIG. 3A illustrates a high-level flow diagram 300 of operation of a system for diagnosing/managing neurological conditions according to some embodiments. FIG. 3B illustrates a high-level flow diagram 350 of operation of a system for determining neurological conditions according to some embodiments.

In some embodiments, there is provided a robotic system that is automated, thereby enabling accurate and rapid diagnoses and management of several neurological indications. For example, the robotic system may be fully automated such that limited or no human operation of the system is relied on to perform the diagnoses and management of neurological indications. In other embodiments, the robotic system is less than fully automated such that some human interaction is relied on (e.g., setup of the system with respect to a patient, minor operating controls such as inputting information needed for operation of the system, and so on). In some embodiments, the system includes a transducer (such as, but not limited to, an ultrasound transducer, TCD, transcranial color-coded sonography (TCCS), or acoustic ultrasound transducer array such as sequential arrays or phased arrays) that emits acoustic energy capable of penetrating windows in the skull/head or neck. In particular embodiments, the system provides a robotic system for automatically performing TCD scans. In some embodiments, the robotic system may include a multiple degree of freedom (DOF) TCD transducer positioning system with motion planning driven by prior knowledge of the human anatomy and cerebral hemodynamics. In some embodiments, the system is capable of two, three, four, five, or six DOF. The positioning system can translate in X and Y axes (e.g., along a surface of a head) to locate the window in translational axes, and in Z axis with both force and position feedback control to both position, and maintain the appropriate force against the skull/skin to maximize signal quality by maintaining appropriate contact force (e.g., as performed in block 301). Two angular degrees of freedom (e.g., pan and tilt) may be used to maximize normal insonation of blood vessels to maximize velocity signals. Further disclosure regarding the robotic system and components thereof is described herein.

Referring to FIG. 3A, at block 301, a kinematic mechanism (e.g., the robotic system) positions a transducer at an acoustic window adjacent a patient's head. After positioning the transducer (e.g., at an optimal location for signal acquisition), at block 302, the system acquires the optimal signal for analysis (e.g., using ultrasound), the signal may be indicative of CBFV. In some embodiments, at block 303, the system performs analysis on the acquired signal. At block 304, the system determines an output (e.g., a clinically actionable decision) based on the analyzed signal, such as, but not limited to, a diagnosis or measured metric/feature.

Referring to FIG. 3B, in some embodiments, to determine the output at block 304, robotic kinematic movement at block 301 is used to position and re-position the transducer, the system optimizes the signals acquired by the transducer positioned at various locations at block 302, and the system performs an analysis on the acquired signals at block 303. Blocks 301, 302, and 303 may be performed multiple times at different locations or at varying angle adjustments before an output decision at block 304 is determined. In some embodiments, blocks 301, 302, and 303 are performed as many times as necessary (e.g., n times) for the system to acquire enough information and data to determine the output at block 304.

In some embodiments, the multiple iterations of blocks 301, 302, and 303 are utilized for vascular mapping of a brain, which is described in further detail below, where information from multiple points along one or more vessels is combined to reach the output at block 304. For example, in the case of stroke, multiple locations along a vasculature may be measured to determine where an occlusion is located. For instance, to determine flow velocity of a vessel, during a first iteration, the system moves along a vessel (at block 301), optimizes the acquired signal (at block 302), and analyzes the signal (at block 303). Subsequently, during a second iteration following the first iteration, the system moves slightly down the vessel (at block 301), optimizes the new signal (at block 302), and analyzes the new signal (at block 303), and so on. During the various iterations of blocks 301, 302, 303, the system may measure and compare velocities of blood flow in the vessel, where a change in velocity or other feature of the CBFV waveform can indicate an occlusion of the vessel and can indicate susceptibility to stroke (e.g., as the output at block 304). The vascular map is also useful in other neurological indications including TBI, dementia, and others for localization of the pathology or better understanding of cerebral hemodynamic asymmetries.

Figure 4:
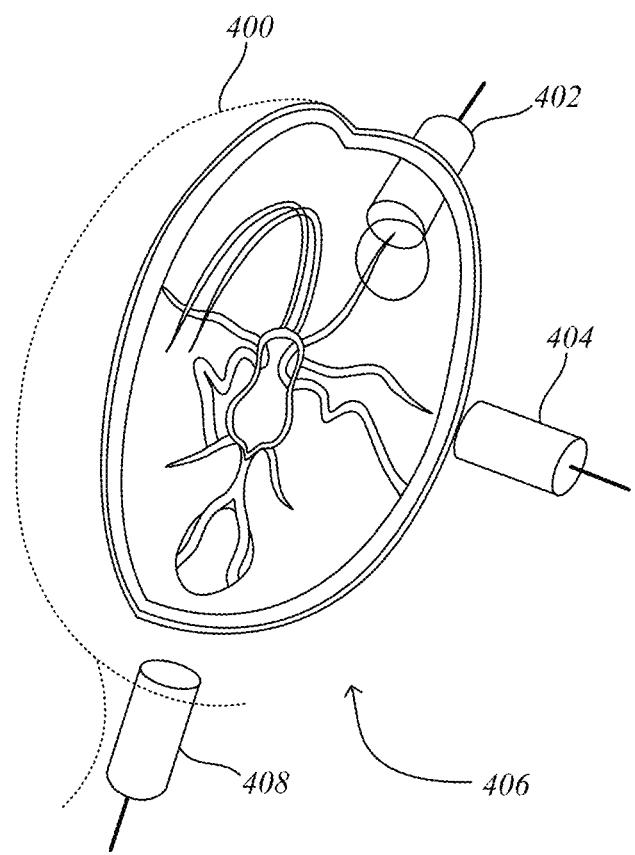
FIG. 4 illustrates a cranium and multiple acoustic windows adjacent the cranium according to some embodiments.

FIG. 4 illustrates a cranium 200 and multiple acoustic windows 402, 404, 406, 408 adjacent the cranium 400 according to some embodiments.

Referring to FIG. 4, the diagram illustrates a plurality of acoustic windows for insonation including the transorbital window 402, the transtemporal window 404, the submandibular window 406, and the transforaminal (e.g., occipital) window 408. According to various embodiments, a system for implementing blocks 301-304 is a robotically automated medical device (e.g., a head-mounted or arm-mounted medical device) that automatically searches, locates, and acquires a stable CBFV waveform from any human's temporal window 404 or other acoustic window (e.g., transorbital window 402, submandibular window 406, and transforaminal window 408) independent of the human's age, size, shape or demography. In some embodiments, the system employs the use of force and torque sensors to maintain appropriate contact force (e.g., at the acoustic windows 402-408) for maximizing signal quality (e.g., at block 301).

Figure 5:
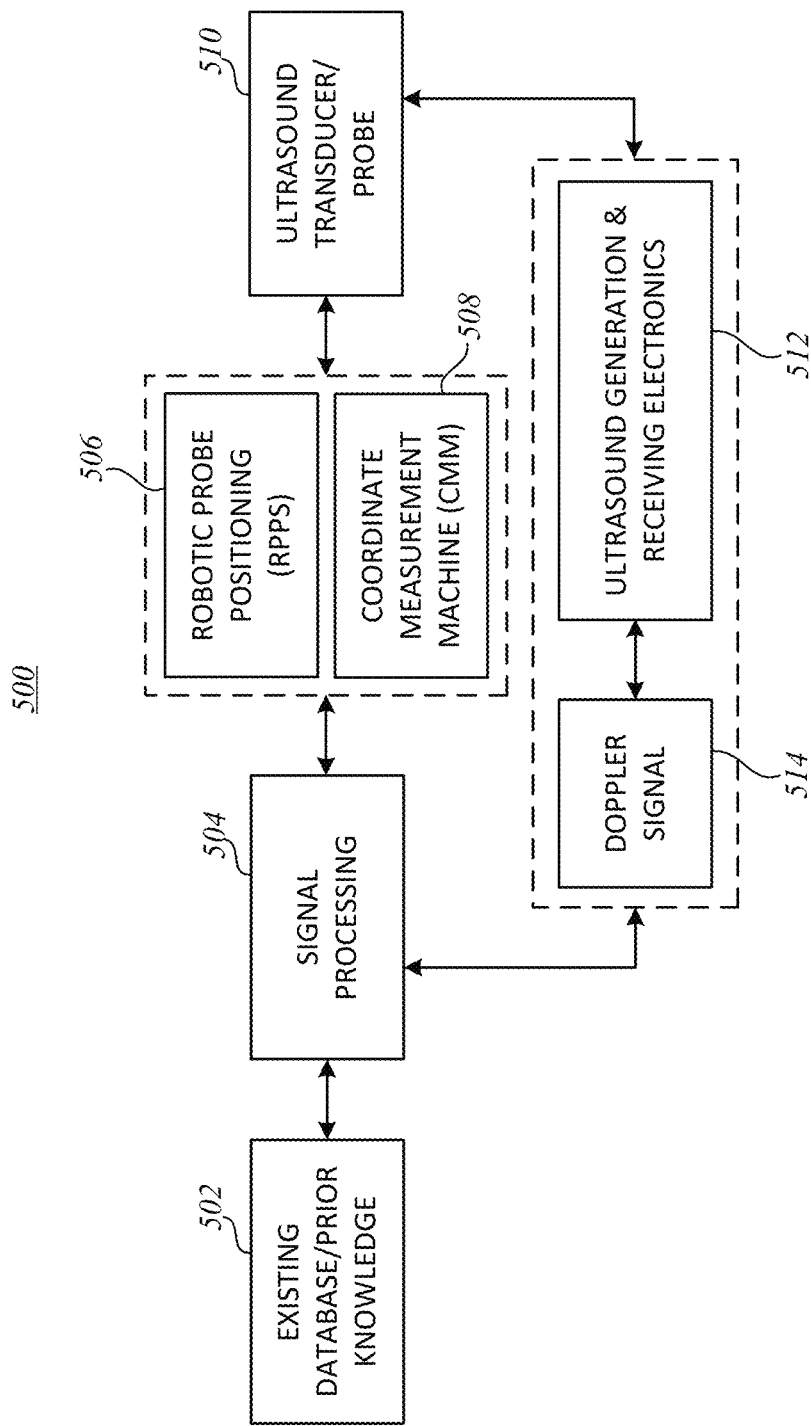
FIG. 5 illustrates a flow diagram for vascular mapping in a system for determining neurological conditions according to some embodiments.

FIG. 5 illustrates a flow diagram 500 for vascular mapping in a system for determining neurological conditions according to some embodiments. At block 502, the system includes an existing database or prior knowledge for accelerating positioning of a transducer for finding an artery or veins of interest. For example, the existing database may include particular information about a patient, such as, but not limited to, cranial structure, vessel locations within the head (e.g., a mapping of vessel structures), age, height, and the like. In addition, the existing database may include general information about the human anatomy for initially direction positioning of the transducer. At block 504, the system includes signal processing for interpreting received signals. At block 506 and block 508, the system includes robotic transducer positioning and a coordinate measurement machine, respectively, for physically adjusting positioning of the transducer based on the signal processing at block 504. At block 510, the system includes the ultrasound transducer that will be adjusted by the robotics at blocks 506 and 508. At block 512, the system includes ultrasound generation and receiving electronics to supply the ultrasound for insonation and to receive the returned signal from an insonated artery/vein (e.g., via the transducer at block 510). At block 514, the system acquires Doppler signals that are transmitted to block 504 for signal processing. Accordingly, because a feedback loop system is provided, the cycle of acquiring a signal and adjusting positioning of the transducer can be repeated indefinitely.

In some embodiments, once a transducer is positioned for insonation of one or more brain or neck vessels as described above (at block 301), an optimal CBF or CBFV signal is acquired (at block 302). In some embodiments, at block 302, the system insonates additional locations along the same vessel or along other intracranial vessels for improved diagnostic and monitoring accuracy. The insonation of additional vessels allows for physiological information from different areas or regions of the brain to be included in signals, which may be significant data for particular neurological conditions. For example, TBI can affect any region of the brain and assessment of blood supply to a specific region may provide useful information for diagnoses and/or management where other regions may be unaffected. As another example, specific types of strokes may impact specific vessels of the brain, and assessment of those specific impacted vessels, and those close in proximity to the impacted vessels, provide significant data.

In some embodiments, at block 302, systems provide a mapping of one or more vessels within the cranial vault. In comparable systems, TCD ultrasound is used for the assessment of CBF or CBFV at discrete points (e.g., at discrete depths) around the Circle of Willis and other large conducting arteries and veins, with limited additional information. According to various embodiments, systems and methods can combine two or more discrete points into a "map" of the cerebral vasculature using the automated mechanism (e.g., at block 301). In some embodiments, the vascular mapping allows for specialized assessment of neurovasculature including the dynamics and position of the vasculature, which can provide healthcare professionals a better diagnosis, triage, and monitoring of a number of neurologic conditions including, but not limited to, stroke (e.g., hemorrhagic or ischemic), TBI (e.g., concussion), intracerebral hemorrhage, migraine, dementia, and others. In some embodiments, systems combine ultrasound signals with their positions in space to capture a representation of local vasculature based on flow and flow velocity. In some embodiments, systems combine ultrasound imaging to additionally capture image data to assist with location and mapping.

Referring to FIG. 5, the diagram 500 illustrates blocks 502, 504, 506, 508, 510, 512, and 514. Four of the blocks 502, 504, 506, and 508 automatically perform advanced transducer placement based on feedback from Doppler signals at block 504.

In some embodiments, a system for positioning the transducer (e.g., a robotic system) is provided for an accurate and repeatable method for positioning of the transducer in a plurality of degrees of freedom (e.g., x-axis, y-axis, z-axis, pan, and/or tilt). In addition, in some embodiments, the system includes components for measuring current coordinates or positioning of the transducer of the system for continuously obtaining exact position information of the transducer, thereby mimicking the TCD sonographer's ability to place and be aware of the transducer's placement (e.g., on a human's head). An advantage of this automated system is a more precise and repeatable implementation of the TCD sonographer's operation. For example, in some embodiments, precision can be obtained to within 1 millimeter (mm) in translation, 0.5 degrees in orientation, and 0.001 N in force. Further disclosure regarding the robotic system and its components are described herein.

At the signal processing block 504, systems mimic a sonographer's function of further adjusting the transducer position based on the signal obtained from the Doppler ultrasound electronics. For example, during an initial signal search, the automated system performs a systematic search to discover an insonation window and find the artery of interest, as further described herein. During signal acquisition, the automated system adjusts the translational (x-axis, y-axis, and z-axis) and orientation (pan and tilt) positions of the transducer slightly, at blocks 506 and 508, to keep the signal quality from degrading.

In some embodiments, at block 502, the system utilizes prior database and prior knowledge to help achieve various functions in an accelerated and more accurate manner. For example, the system may include prior knowledge of highly probable translation and orientation points that likely yield the fastest route to discovering an insonation window and finding a vessel of interest. In some embodiments, block 502 includes an atlas from other imaging modalities (Magnetic Resonance Angiography—MRA, Magnetic Resonance Venography—MRV, MRI Time of Flight, Diffusion Tensor Imaging—DTI, CT angiography—CTA, etc.) to guide transducer positioning. In some embodiments, block 502 contains previous TCD scans of individuals with similar characteristics can provide positional information (x-axis, y-axis, z-axis, pan, and tilt) as well as cerebral hemodynamic information (blood flow characteristics). Finally, in other embodiments, block 502 can combine positional (traditional medical imaging) with dynamic information to aid in the accuracy and speed of the blood flow assessment.

In some embodiments, the database includes a magnetic resonance imaging (MM, MRA, CT, CTA, angiography, time of flight MM, phase contrast MRI, or other medical imaging) atlas. In some embodiments, there is built and maintained a database of anatomical MRI templates used to model anatomy for co-registered TCD waveforms. In some embodiments, the database includes, but is not limited to, at least one of the following: 1) Magnetic Resonance Angiography (MRA) scans of the full head volume, including complete images of brain vasculature, as well as skull and identifiable scalp fiducials (or other imaging types listed above); and 2) Multiple scans across different demographics (e.g., age, gender, history of pathology, etc.), from which age and gender matched averaged templates can be constructed.

In some embodiments, there is provided a co-registration atlas of TCD with anatomical Mill or other structural imaging. With scalp fiducial coordinates recorded for each scan in the TCD database, and identifiable on the demographic-matched templates, a set of translations and rotations which best aligns the two coordinate systems can be derived. From the individual Mill and TCD atlases, a probabilistic map of vessel locations for informing vessel searches in new subjects or patients can be constructed.

In some embodiments, the database includes a computerized topography (CT) or computerized topography angiography (CTA) atlas. In some embodiments, there is built and maintained a database of anatomical CT or CTA templates used to model anatomy for co-registered TCD waveforms. In some embodiments, the database includes, but is not limited to, at least one of the following: 1) computerized topography angiography (CTA) scans of the full head volume, including complete images of brain vasculature, as well as skull and identifiable scalp fiducials; and 2) Multiple scans across different demographics (e.g., age, gender, history of pathology, etc.), from which age and gender matched averaged templates can be constructed.

Accordingly, in various embodiments, systems can mimic an expert TCD sonographer in acquiring a signal. However, due to superior placement accuracy and repeatability of the automated system, more advanced functions not possible by a human expert sonographer may be implemented. One such advanced function is vascular mapping, which is the process of generating the velocity and/or geometric map of a cerebral vasculature.

Figure 6A:
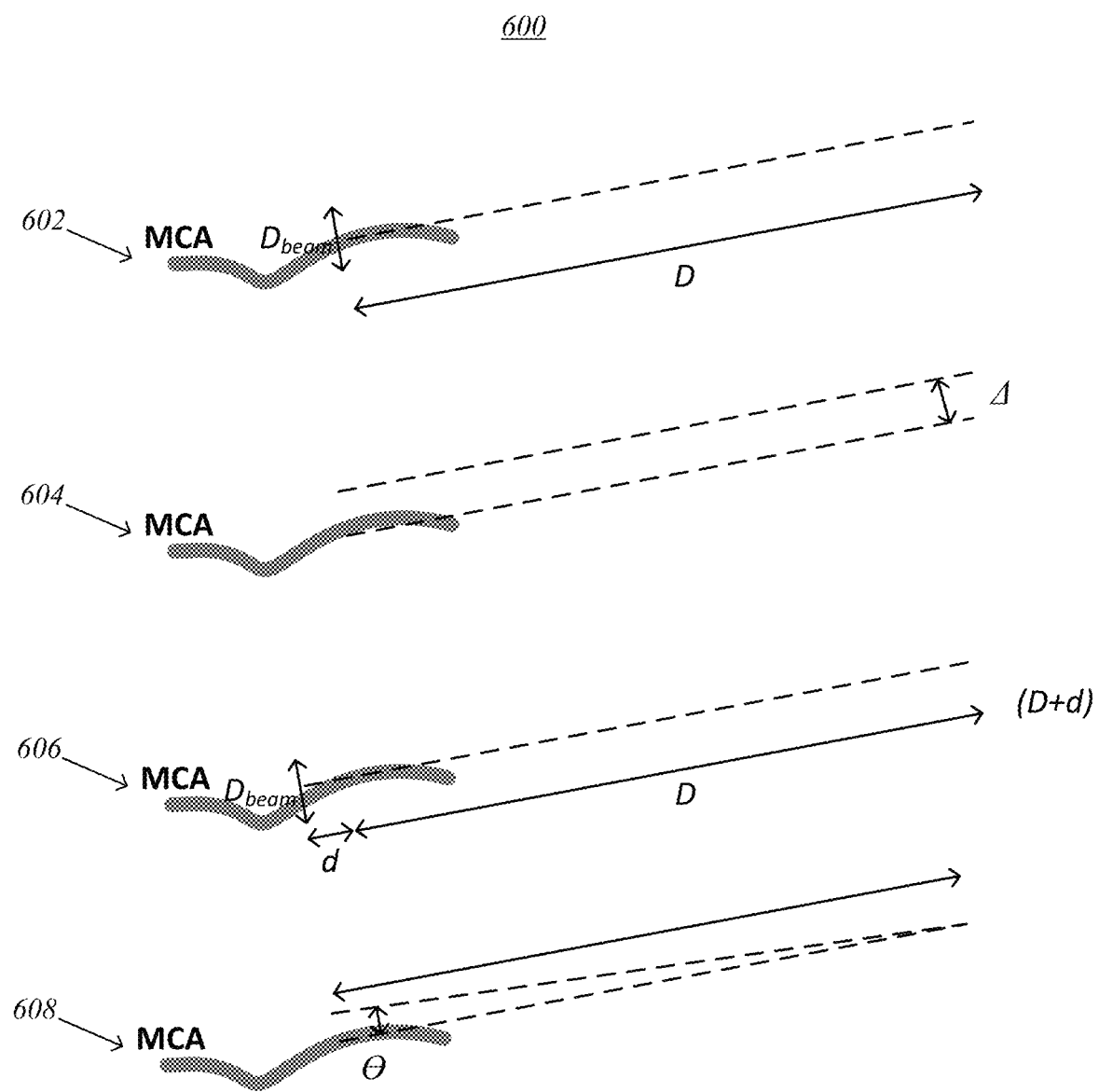
FIG. 6A illustrates a diagram showing adjustments to positioning of a transducer for insonation of vasculature in a system for determining neurological conditions according to some embodiments.

FIG. 6A illustrates a diagram 600 showing adjustments to positioning of a transducer for insonation of vasculature in a system for determining neurological conditions according to some embodiments. In some embodiments, process 600 illustrates a method for reconstructing a map of the cerebral vasculature. Stage 602 illustrates an initial position stage of a beam of a transducer (e.g., an ultrasound beam). Stage 604 illustrates a stepping in transition stage of the transducer beam. Stage 606 illustrates a stepping in depth stage of the transducer beam. Stage 608 illustrates a stepping in orientation stage of the transducer beam. The MCA represents the Middle Cerebral Artery, a major conducting artery of the brain. This method can be extended to other large arteries or veins of the head and neck.

In some embodiments, at stage 602, a transducer is at an initial position, for example, a position at which a stable signal has been acquired from a vessel of interest. Accordingly, once the position for acquiring a stable signal is located, the robotic system is commanded to incrementally adjust the position of the transducer (at block 506 and block 508). In some embodiments, the commanded position follows a predetermined path (stored at block 502). In other embodiments, the adjustment of positioning of the transducer can be updated based on Doppler signals obtained at each new position (at block 514 and block 504). In some embodiments, incremental adjustment in position of the transducer includes changes in the following components: lateral translation (stage 604), depth increment (stage 606), or angular increment (stage 608). Although FIG. 6 illustrates one direction of lateral or angular change, the same can occur in other dimensions (e.g., y-axis and pan).

At each new position of the transducer after an incremental change, a new sample volume is insonated, providing a different Doppler signature. In some embodiments, the combined information from all of the new sample volumes can be aggregated and "stitched" together to form a map of that insonated segment of the vasculature. In some embodiments, this process is repeated over a predetermined volume of a search of interest (e.g. determined to encompass the entire Circle of Willis and other large conducting arteries or volumes thereof) to obtain the map of the cerebral vasculature. For example, this process may be applicable regardless of the size of the desired map to be obtained (e.g., a size ranging from a segment of a vessel to all of the intracranial arteries and veins). According to various embodiments, various suitable algorithms can be used to increase the speed and accuracy of search and map generation of the transducer, based both on prior knowledge of anatomy as well as in-experiment feedback from signals.

In various embodiments, there are various types of maps that can be generated using the systems and method illustrated in FIGS. 5 and 6. The type of map generated depends on the system implementation and time restrictions dictated by the end-use cases.

In some embodiments, a spatial map of intracranial vasculature can be obtained. Using mainly Power Motion Mode Doppler (PMD), also known as M-Mode, the location of the vessels can be obtained following the systematic search described in the previous section. According to some embodiments, approximate calculations for such a map is shown below in Table 1.

TABLE 1

| Parameter | Value | Unit | Comment |
|---|---|---|---|
| Maximum depth of interest | 100 | mm | Highest depth to image/map |
| Min resolution needed - linear | 1 | mm | Step would be coarsest at the highest depth |
| Overlap factor | 2 | # | Effective number of overlaps |

TABLE 1-continued

| Parameter | Value | Unit | Comment |
|---|---|---|---|
| Min resolution needed - angle | 0.29 | degree | |
| Max. sweep angle desired | 30 | degree | e.g. total sweep in each dimension - Roll and Pitch - would be 2X this value |
| Number of sweep steps | 419 | | Multiply 2 steps for Plus/Minus and two dimensions |
| Time for each snapshot | 1 | second | We have shown time steps as short as 10 ms |
| Safety factor | 2 | | |
| Total time for map | 14 | minute | |

In some embodiments, a velocity or flow map can be obtained. In order to obtain a velocity map using the same approach as described above with respect to the spatial map, a spectrogram (e.g., for displaying power spectral density of the reflected Doppler waveform) is used to obtain velocity components at each insonated location. Such an approach includes "sweeping" of the volume in the depth dimension (comparable implementations of TCD hardware generally output spectrograms at only one depth setting). According to some embodiments, approximate calculations for such a map is shown below in Table 2. In further embodiments, coarser searches, refined location and automated speed all reduce the total time calculated in Table 2 and it is anticipated that most commercial applications will be completed in significantly less time.

TABLE 2

| Parameter | Value | Unit | |
|---|---|---|---|
| Upper limit to map depth range | 85 | mm | |
| Lower limit to map depth range | 35 | mm | |
| Min resolution needed - Linear | 1 | mm | |
| Overlap factor in angle | 2 | # | |
| Overlap factor in depth | 2 | # | |
| Min resolution needed - angle | 0.34 | degree | At the maximum depth |
| Worst resolution needed - angle | 0.82 | degree | |
| Max. sweep angle desired | 30 | degree | i.e. total sweep in each dimension - Roll and Pitch - would be 2X this value |
| Avg. # steps at each depth | 208 | | |
| Finest possible resolution in depth | 1.00 | mm | Assuming no hardware change |
| # depth steps | 50 | # | |
| Time for each snapshot | 1 | second | |
| Safety factor | 2 | | |
| Total time | 6 | hour | |

In some embodiments, blood flow in the brain can be modeled as a piecewise continuous vector-valued function, v(x), which gives the velocity of blood flow at some position. The locations of vessels are given by the subsets of this space which are nonzero. By walking the vessel, a discrete set of points sampled at semi-regular intervals along the subspace of our coordinate system contained within a particular vessel is obtained. To approximate v(x), "connecting the dots" of the discrete points is implemented, and the velocity is obtained by interpolating between successive velocity values in a sample.

However, since vessels are not one-dimensional lines through space, some additional approximations can be added to a model. In some embodiments, a cylindrical pipe is used for a reasonable approximation for a vessel. The pipe can be constructed using circular disks of some given radius, determined by a vessel ID (e.g., for identifying which vessel) and information from existing databases, centered on each position in our sample $x_i$ and oriented such that the plane of the disk is perpendicular to the velocity vector at that point. Blood is then assumed to flow in the direction parallel to the axis of the pipe. Examples can include a constant velocity equal to the measured velocity or a parabolic velocity curve, with average velocity equal to the measured velocity. In some embodiments, blood flow velocity everywhere outside of vessels is assumed to be zero.

In some embodiments, a database of acquired TCD parameters for each subject or patient scanned is maintained. The database includes, but is not limited to, at least one of the following measurements and information: 1) measurements of the distance between fiducial points on the head (e.g., tragus, eye corner, eye at brow, top of ear); 2) position and orientation of the transducer, and depth of the sample volume at each vessel lock relative to the coordinate system defined by the fiducials; 3) TCD waveform characteristics (e.g., mean velocity, pulsatility, sub-peaks, etc.); 4) demographic information (e.g., age, gender, history of pathology, etc.).

In some embodiments, a method for mapping a vascular structure within a sub-volume of the human head using TCD ultrasound M-mode data is provided. The vessel mapping protocol can be executed either in conjunction with a vessel search, or independently (before or after) an optimal vessel signal has been identified, as well as with single (e.g., unilateral) or bilateral transducer configurations. Because M-mode reveals information across a large range of depths simultaneously, this potentially reduces the space of required search points by multiple orders of magnitude, resulting in faster anatomical reconstruction.

In some embodiments, this vascular anatomical mapping procedure includes co-registration of subject head coordinates with anatomical medical imaging (MRI, MRA, CT, CTA, etc.) (e.g., subject specific or using age and/or gender-matched template) via identifiable fiducial points (e.g., tragus, eye corner, eye at brow, top of ear). The method further includes transtemporal search volume parcellation and mapping to space of position and orientation grid search coordinates for coverage of the search volume, including multiple orientations for each voxel. The method further includes M-mode smoothing, thresholding, and summation across orientations for each voxel, resulting in "strength of flow" indices, either towards the window (e.g., positive values), or away from the window (e.g., negative values). The method further includes reconstruction of space curve corresponding to vessel anatomy via three dimensional interpolation of strength-of-flow indices, wherein voxels displaying weak positive/negative or zero flow are connected across paths inferred from local curvature as well as priors derived from the structural imaging atlas. In some embodiments, the method further includes manifold learning of the resultant vessel coordinates to represent vessel anatomy in two dimensions to simplify visualization of vessel structure, and facilitate analyses of pathology.

Accordingly, in some embodiments, the system includes two types of maps including different types of information. The TCD maps (listed above) provide dynamic information (e.g., information about blood flow). The medical imaging provides anatomical information about the locations of the vessels. As such, in some embodiments, the system utilizes a combination of these two types of information. For example, the system (e.g., the robotics) may provide positional information which can be combined with the blood flow information acquired via the ultrasound. In some embodiments, this information can be supplemented with anatomical information from an atlas (e.g., a specific vessel should be in a specific anatomical location) and approximate dynamics information from a database of TCD information.

Figure 6B:
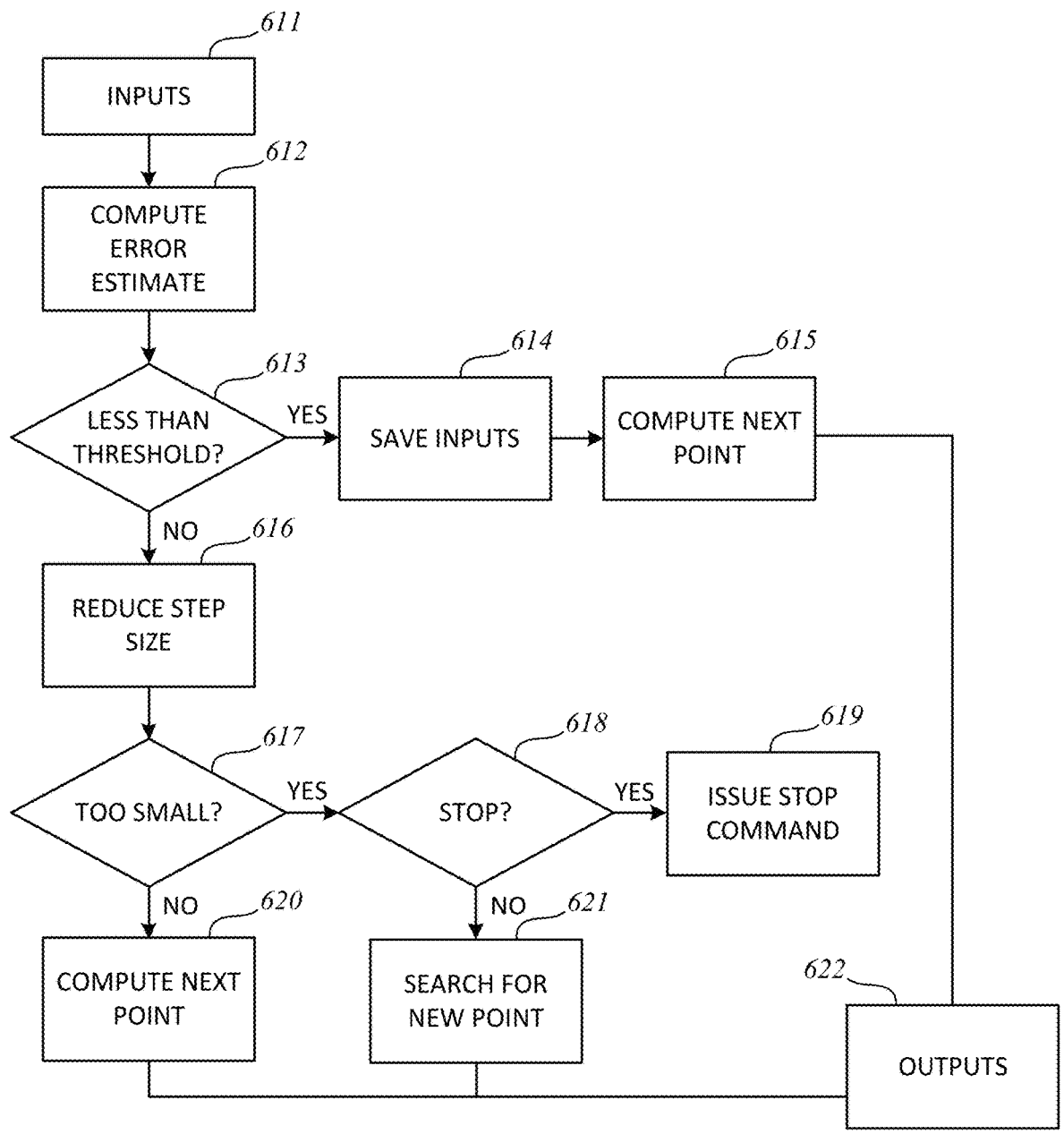
FIG. 6B illustrates a method of vessel walking in a system for determining neurological conditions according to some embodiments.

FIG. 6B illustrates a method 610 of vessel walking in a system for determining neurological conditions according to some embodiments. In some embodiments, at block 611, input of the vessel walking method 610 include current position vector $x_i$, current velocity vector $v_i$, and current vessel identification probability, $P_{ID}$, given as a vector of probabilities for each potential vessel. At block 612, the method 610 includes computing an error estimate. The error is an estimate of the confidence level that the given inputs are reasonable given the history of previous points along with any prior knowledge we have from, e.g., any existing information databases. An example for how this is computed is to use the dot product of the current velocity, $v_i$, with the previous velocity, $v_{i-1}$, normalized by the magnitude of the previous velocity. This provides a measure of similarity between the two vectors. The result of this product should be close to 1 for similar vectors. The motivation behind this is that blood flow velocity vector, v(x), should be a continuous function inside the vessel. So, for sufficiently small changes in x, v should not change very much. In some embodiments, an example error function is defined by the following function, which captures both drastic changes in flow orientation and magnitude:

$$\text{Error} = 1 - \frac{V_{i-1} \cdot V_i}{\|V_{i-1}\|},$$

In some embodiments, at block 613, the method 610 includes determining whether the error estimate is below a predetermined threshold level. The predetermined threshold determines what level of error is acceptable and what level of error indicates that something has gone wrong that should be addressed. This threshold can be decided in advance and may be found empirically. It can also be adjusted based on a priori information from existing information databases. For example, if a branch is expected to be encountered, then the error thresholds can be relaxed by an amount appropriate to the degree to which it is expected this physical feature will modify the expected velocity.

In some embodiments, at block 614, the method 610 includes saving inputs. If the error is acceptable (block 613: YES), then the inputs are reasonable and the method 610 can proceed normally. These inputs may be appended to the vector containing the history of inputs to the vessel walking algorithm.

In some embodiments, at block 615, the method 610 includes computing a next point. The next point to search for a signal for the current vessel can be computed using the following equation, where $\hat{v}_i$ denotes a unit vector pointing in the direction of $v_i$, and $\Delta$ is the step size, and the choice of sign depends on whether walking "up" or "down" the vessel.

$$x_{i+1} = x_i \pm \hat{v}_i \cdot \Delta$$

In some embodiments, at block 616, the method 610 includes reducing a step size. If the error estimate is too large (block 613: NO), then there is an indication that something may be wrong. Accordingly, the step size may be decreased. There tends to be a tradeoff between speed and accuracy when it comes to selecting an appropriate step size. An error may simply be an indication that a structure more complex than a straight vessel has been encountered, and the system should temporarily take a smaller step to capture the smaller features of the more complex vessel.

In some embodiments, at block 617, the method 610 includes determining whether the step size is too small. Given that the resolution of TCD is limited by the beam size, there is a lower bound that exists beyond which taking a smaller step no longer makes sense. Once the step size has been decreased, a check is performed to make sure the step size is not smaller than some reasonable lower bound based on the TCD's spatial resolution.

In some embodiments, at block 618, the method 610 includes determining whether the method 610 should stop. If the step size becomes too small (block 617: YES), then the error should be dealt with another way. At some point, it is known that the vessel walking algorithm should stop because vessels are finite. The stopping criteria can be based on prior information from existing databases. The vessel walked so far can be compared to existing information to determine whether a sufficient amount of it has likely been mapped.

In some embodiments, at block 619, the method 610 includes issuing a stop command. If the vessel has been sufficiently mapped (block 618: YES), a stop command is issued to indicate that the system should move to a new location or vessel.

In some embodiments, at block 620, the method 610 includes computing a next point. If the reduced step size is still a reasonable size (block 617: NO), then the next point to optimize around can be computed using the same equation as that used above in connection with block 615.

In some embodiments, at block 621, the method 610 includes searching for a new point. If this block is reached, then the step size is too small, but the vessel has not been sufficiently mapped to justify stopping (block 618: NO). This could occur, for example, if the system has reached a section of the vessel which is simply not accessible to TCD due to location or orientation. Additionally, this may indicate a problem with the vessel such as a stroke. The system may thus have a way of trying to pick the vessel back up in another location. A new point will be found using some search algorithm. Possibilities include a local spiral or grid search around the point, but excluding positions which have been visited previously. Information from existing databases can also be used to inform the search of positions which are likely to contain the vessel being searched for.

In some embodiments, at block 622, the method 610 includes providing outputs. The primary output is a prediction, $x_{i+1}$, of the next point for the robot to optimize around in the vessel. Additionally, vectors including the entire history of positions, velocities, vessel identification probabilities, and error estimates are saved.

Figure 7A:
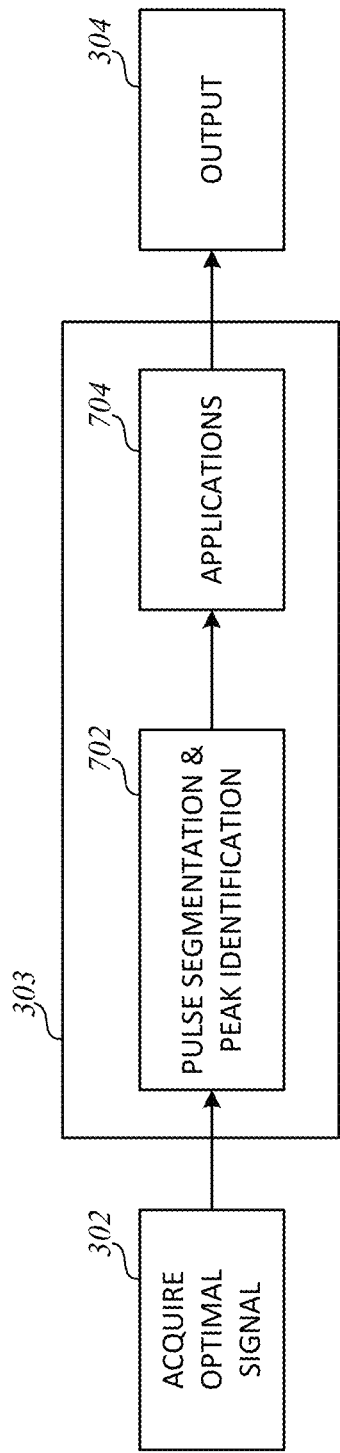
FIG. 7A illustrates a flow diagram for signal analysis in a system for determining neurological conditions according to some embodiments.

FIG. 7A illustrates a flow diagram 700 for signal analysis in a system for determining neurological conditions according to some embodiments. At block 702, the system includes a pulse segmentation and feature identification stage. At block 704, the system includes an applications stage of the results from block 702.

In some embodiments, once an optimal signal is obtained from a vessel, at block 302, using the automated mechanism, analysis of the acquired and optimized CBFV data is performed, at block 303. In some embodiments, pulse segmentation and feature identification at block 702 is utilized for signal analysis of the CBFV signal, which solves the technical problem of extracting important physiological data from the CBFV signal that has previously been ignored. Following the analysis of the data at block 702, there are a number of specific clinical indications that the advanced analysis of the CBFV signal can be applied to, at block 704.

In some embodiments, the optimal CBFV or CBF signal from block 302 is analyzed for the characterization of the physiologically relevant information that has previously been ignored. In some embodiments, block 702 is an example of a beats processing platform for the extraction of beats and features, as generated by heart pulses in the CBFV waveform and is a part of the signal analysis at block 303. For this description, a beat is defined as the segment of time between subsequent heart beats and the resultant CBFV waveform (diastolic point to diastolic point). In some embodiments, signal analysis (e.g., block 303) utilizes a TCD or ultrasound scan, extracts out relevant segments (e.g. defined by an experimental protocol) and extracts the beats. The system then analyzes the beats for specific rejection criteria that focus on the quality of beats and detects peaks and valleys within the CBFV waveform. Healthy TCD of subjects include three peaks, but neurological disorders may change the healthy waveform shape of the beats. Examples of such peaks of waveforms are shown in FIG. 7C and described below (e.g., peaks 712a,712b,712c, 722a, 722b, 722c, 732a, 732b, and 732c).

In some embodiments, the pulse segmentation and feature identification of the signal analysis platform (e.g., block 303) has a number of functional criteria. The first relates to beat processing, as the signal analysis platform (e.g., block 303) will take in a CBFV time series and return an ordered list of tuples of the form bi=(starti, endi) corresponding to the beginning and ending indices of the beat at the ith beat, in the TCD signal. Second, the beats may not overlap, as defined by endi<=startj whenever i<j. The third criterion relates to feature finding, in that for each beat that is returned, a list of three traditional peaks are returned and a list of the three corresponding valleys. The fourth criterion relates to beat rejection, as the beats should conform to a number of signal quality assurance (SQA) criteria. The beats that do not adhere to the SQA criteria will be rejected with the rejection reason specified. In some embodiments, the SQA is a set of criteria, as determined by an experimental process.

Figure 7B:
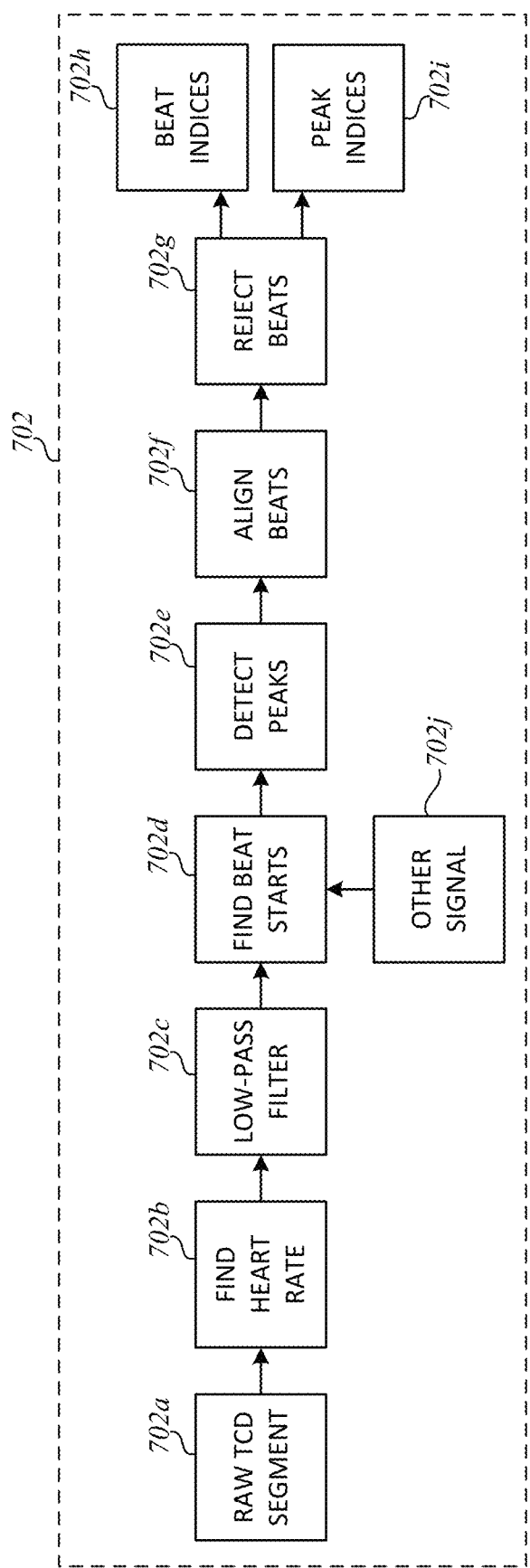
FIG. 7B illustrates a flow diagram for signal analysis including peak segmentation and peak identification in a system for determining neurological conditions according to some embodiments.
Figure 7C:
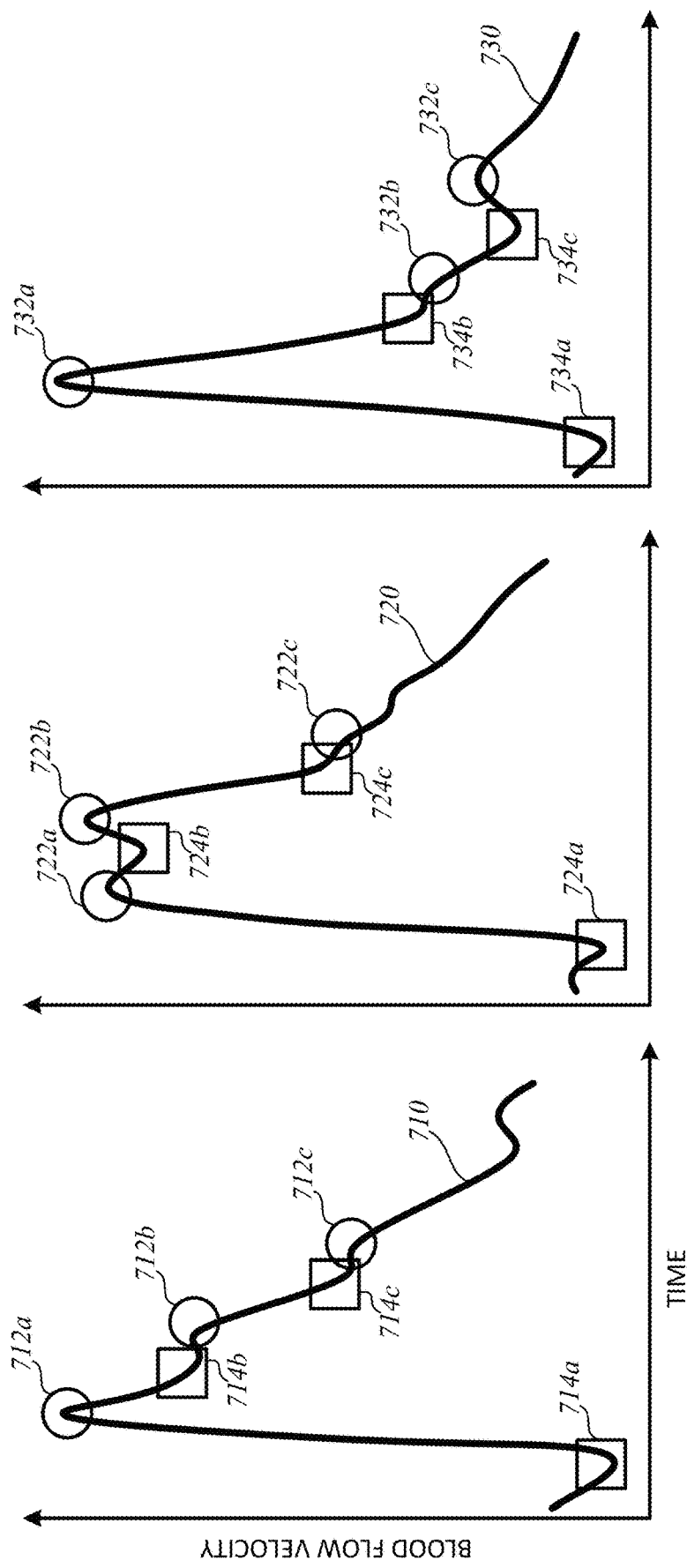
FIG. 7C illustrates a plurality of CBFV waveforms for signal analysis in a system for determining neurological conditions according to some embodiments.

FIG. 7B illustrates a flow diagram for signal analysis including peak segmentation and peak identification block 702 in a system for determining neurological conditions according to some embodiments.

In some embodiments, the beats processing architecture at block 702 is designed as an experimental platform for analyzing the results of different methodologies. Each component or block 702a-702j is defined using a configuration file as well as a library of interchangeable methods for the component or block.

In some embodiments, to estimate the heart rate at block 702b, the raw TCD signal (from block 702a) is first partitioned into same length intervals and then the power spectrum density (PSD), $\hat{p}(\omega)$ for each interval is calculated. In order to ensure that the fundamental frequency of the heart beat is estimated (and not the harmonics) a harmonic PSD technique is employed that combines n spectral components according to the following equation:

$$h(\omega) = \sum_{k=1}^{n} \min(\alpha * \hat{p}(\omega), \hat{p}(k\omega))$$

In some embodiments, this approach accounts for variations in the power distribution among harmonic frequencies. The frequency where the maximum of the h( ) occurs is then selected as the heart rate frequency in that interval. The estimated heart rate is then returned as the mean of the fundamental frequencies across all intervals. The estimated heart rate is then used to define the following parameters: 1) cutoff frequency of low-pass filtering, 2) window to search for beat starts, 3) window to search for peaks in a beat, and 4) reference point for beat alignment.

In some embodiments, at block 702c, a low-pass filter is applied to the TCD signal after the heart rate is estimated. The cutoff frequency for low pass filtering varies according to the estimated heart rate. Examples of low-pass filters are fast Fourier transform (FFT), finite impulse response (FIR), and forward backward filter filtfilt from scipy.signal. The purpose of the filtering is to remove high frequency noise from the signal allowing for a better determination of the location of beats and peaks. High frequency noise creates a large number of local minima and maxima, affecting the processing quality. The advantage of FFT and filtfilt is that no phase-shift is introduced. However, these methods may not be used in real-time with streaming data as they require future knowledge of the signal. Accordingly, in some embodiments, the system using signal analysis (e.g., block 303) has access to the entire signal ahead of time, or introduces a reporting lag for real-time systems.

In some embodiments, at block 702d, initial estimations for where the beats start is generated by finding all local minima that are closely followed by a local maxima that is at least some threshold (e.g., as defined in the configuration file) higher than the minima. The start is assumed to be the onset of the beat (e.g., the diastolic valley from the previous beat), and the first peak is assumed to be the systolic peak. Next, the successive beat starts are compared against each other. In some embodiments, if two successive beat starts are too close to each other (as defined by a maximum heart-rate) one of the starts is removed from consideration based on the following ordered procedure (assume start1 is close to, but precedes, start2; define peak1 and peak2 to be the corresponding systolic peaks): 1) If the systolic peaks are the same, remove start1 since start2 is the true diastolic valley since it is a closer local minimum, in relation to the systolic peak; 2) If the rise from start1 to peak1 is greater than or equal to the rise from start2 to peak2, then remove start2 as it is likely actually the valley between the first and second peaks; 3) Otherwise, remove start1 as it is likely a local minimum, followed by a sharp spike due to noise, in the previous beat's diastolic trough.

In some embodiments, at block 702e, the system detects peaks. A problem in detecting TCD peaks is that they are not always realized as true mathematical maxima of the time series. This problem frequently happens to peak two as it is often not prominent enough to distinguish itself from the systolic peak (peak one). To deal with this problem, the system allows for almost-maximum values to be classified as peaks. First, the system mathematically defines what it means to be a maximum. For a time series y=y(t), the maximum value is attained when both y'=0 and y is concave down, which in turn implies that y"<0, or that y' has negative slope at the point where y'=0. To find true peaks, it is sufficient to find points where y'=0 and y"<0. However, the system is configured to find almost-maxima as well. These almost-maxima will be defined as points where the slope of y is negative, but almost becomes positive.

To find both true maxima, and almost-maxima for y, the system first finds the local maxima for y'. For each local maximum coordinate pair $(t_p, y_p')$ of y', the following analysis is performed: (1) If $y_p' \geq 0$, then the smallest value t* such that $t_p \leq t^*$ and y'(t*)=0 gives the y maximum of (t*,y(t*)); and (2) If $-\varepsilon < y_p' < 0$ for some small $\varepsilon$, then $(t_p, y_p')$ is an almost-maximum and it is kept as a beat peak.

In some embodiments, possible peaks that are overwhelmed by peak two are searched. If peak two grows higher than the peak one, peak one is still listed as the systolic peak. To deal with this, the system analyzes curvature changes leading up to the first detected peak. The assumption is that from the diastolic valley (valley one) to the systolic peak (peak one), there should be one inflection point. In some embodiments, the system analyzes the number of concavity changes in this range. If the number of concave-down sections is greater than one, then it is likely that peak two was picked up as the first peak. To infer a position for the true systolic peak, the point of maximum curvature is computed. The point of maximum curvature is computed as the following equation:

$$t_s = \mathrm{argmax}\left\{\kappa(t) = \frac{|y''|}{(1+y'^2)^{\frac{3}{2}}}\right\}.$$

In some embodiments, the peaks are then moved down. Peak three is assigned the point previously held as peak two, peak two is assigned the point previously held as the systolic peak, and the systolic peak is then set to the point (ts, y(ts)). In some embodiments, this step is removed by looking for this case in the "almost-maxima" steps. As the almost-maximum computation involves an $\varepsilon$ tolerance for peaks of y', the system can similarly define a tolerance for $0 < y' < \varepsilon$, where it almost crosses zero (to form a true maximum). The heuristic is that the slope of y is positive, but it almost goes negative, which indicates an almost-maximum.

Accordingly, there is a strong distinction between systems according to various embodiments and comparable systems. Comparable systems label the beat maxima as the systolic peak whereas systems according to various embodiments find the true systolic peak even when it is not realized as the beat maximum. Similarly, systems according to various embodiments also identify the true diastolic point rather than simply labeling the beat minimum as diastolic. The imprecision in systolic and diastolic analysis in comparable systems render it very difficult to identify differentiation between sub-peaks. However, in some embodiments of this system, the signal analysis platform (e.g., block 303) extracts the three sub-peaks and valleys and can correctly assign the systolic peak to the first peak providing a proper characterization of the diastolic-to-systolic beat differentiation missed in comparable systems.

In some embodiments, at block 702f, the system performs beat alignment. The beat alignment lines up all the beats with a single point of reference. To align the beats, the user specifies an alignment type from the options: 1) Valley: align at the diastolic valley; 2) peak: align at the systolic peak; 3) mid-rise: align at the midpoint between the diastolic valley and systolic peak; and 4) inflection: align at the concavity inflection point between diastolic valley and the systolic peak. The second specification for alignment is the point in the temporal domain to align the previous selection to. As an example, a typical alignment would be to align beats by systolic peak, aligned to the beat time point of 0.1 s.

In some embodiments, at block 702g, the system rejects beats. For each beat, a collection of preceding beats called pre, and subsequent beats called post, are collected. The pair {pre, post} is called the context of beat. The size of the context is prescribed in the configuration file. The SQA rejection criteria are defined as a set $REJ = \{rej_c\}_{c \in crit}$, where each $rej_c$ is a function, as shown by the following:

$rej_c$:{beat,context}→{true,false}

In some embodiments, the above function returns the rejection determination for criteria c. If any of the $rej_c \in REJ$ is true, then the beat is rejected and criteria c is recorded. The available rejection criteria are described below.

In some embodiments, the rejection criteria includes correlation distance to mean beat. The mean of the normalized pre and post beats is computed as $m_{pre}$ and $m_{post}$. The correlation distances are computed between $m_{pre}$, $m_{post}$ and the normalized beat, yielding $d_{pre}$ and $d_{post}$, respectively. If both $d_{pre}$ and $d_{post}$ are above a defined threshold, then the beat is rejected.

In some embodiments, the rejection criteria includes correlation distance. The correlation distance is computed between each of the normalized pre beats and the normalized beat. The median of the computed distances is calculated as $med_{pre}$. Similarly, $med_{post}$ is computed. If both $med_{pre}$ and $med_{post}$ exceeds a prescribed threshold, then the beat is rejected.

In some embodiments, median is used over mean to prevent a single bad beat in either the pre or post sets of beats from corrupting the computation. However, in other embodiments, the mean from the pre set and the median from the post set is used since the pre set is already processed with beat rejection, leaving only "good" beats in the pool. Additionally, a standard set of "accepted beats" can be used for comparison with either the pre or post set. In some embodiments, the established library of beats is inspected manually to ensure accuracy.

In some embodiments, the rejection criteria includes Euclidean distance to mean beat. The mean of the pre and post beats is computed as $m_{pre}$ and $m_{post}$. The Euclidean distances are computed between $m_{pre}$, $m_{post}$ and the beat, yielding $d_{pre}$ and $d_{post}$, respectively. If both $d_{pre}$ and $d_{post}$ are above a defined threshold, then the beat is rejected.

In some embodiments, the rejection criteria includes Euclidian distance. The Euclidean distance is computed between each of the pre beats and the normalized beat. The median of the computed distances is calculated as $med_{pre}$. Similarly, $med_{post}$ is computed. If both $med_{pre}$ and $med_{post}$ exceed a prescribed threshold, then the beat is rejected. In some embodiments, median is used to prevent a single bad beat in either the pre or post sets of beats from corrupting the computation. However, in other embodiments, the mean from the pre set and the median from the post set is used since the pre set is already processed with beat rejection, leaving only "good" beats in the pool.

In some embodiments, the rejection criteria includes Mahalanobis distance. The Mahalanobis distance is computed between each of the pre beats (e.g., normalized pre beats) and the beat (e.g., normalized beat). The median of the computed distances is calculated as med$_{pre}$. Similarly, medpost is computed. If both med$_{pre}$ and med$_{post}$ exceed a prescribed threshold, then the beat is rejected. In some embodiments, median is used to prevent a single bad beat in either the pre or post sets of beats from corrupting the computation. However, in other embodiments the mean from the pre set and the median from the post set is used since the pre set is already processed with beat rejection, leaving only "good" beats in the pool.

In some embodiments, the rejection criteria includes peak distance. The height difference is computed between each of the sub-peaks of the pre beats and the normalized beat. The mean of the computed distances is calculated as m$_{pre}$. Similarly, m$_{post}$ is computed. If both m$_{pre}$ and m$_{post}$ exceed a prescribed threshold, then the beat is rejected. This rejection criteria is included since some noise patterns are extreme jumps at the systolic peak value; however, in other embodiments, these noise patterns might be easily detected using jerk rate criteria.

In some embodiments, the rejection criteria includes jerk rate. The terminology jerk comes from y''', which is the third derivative of the blood position since the TCD wave is a velocity (first derivative). The maximum value of y''' of a beat is computed and compared to a prescribed threshold. If it is larger than the threshold, the beat is rejected. The reasoning behind this is that the acceleration of a fluid should change smoothly. This criteria may be useful with many scans that have random blips in the waveform.

In some embodiments, the rejection criteria includes low mean. The mean value of beat is computed, across all of its temporal domain, and compared to a prescribed threshold. If it is too low, the beat is rejected. In some embodiments, this rejection criteria includes computing the threshold for the signal dynamically (e.g., by the mean of the entire TCD signal 0.8× mean(TCD)). In some embodiments, low mean threshold is set to the 1 percentile of the data distribution. As such, a problem with rejecting beats with low velocity may be fixed.

In some embodiments, the rejection criteria includes low onset. The onset value (e.g., the diastolic valley of the preceding beat) of beat is compared to a prescribed threshold. If it is too low, beat is rejected. According, this criteria allows rejection of truly bad signals, when the signal drops during a scan. In some embodiments, the threshold for the signal is computed dynamically (e.g., a histogram of the entire TCD signal with a threshold set to some cutoff of the bins that clearly is out of normal range). In some embodiments, low onset threshold is set to the 1 percentile of the onset points distribution. Accordingly, a problem with rejecting beats with low velocity may be fixed.

In some embodiments, the rejection criteria includes a small peak. The maximum of the beat is compared to a threshold scalar multiplier of beat's mean. If it is too low, beat is rejected. Accordingly, this criteria rejects beats where the maximum peak is not significant, indicating that beat is likely malformed or not a correctly segmented beat.

In some embodiments, for each beat that is rejected, the corresponding peak list is also rejected. The peaks could be determined after beat rejection, except that the first peak is used in beat alignment, which occurs before rejection since it puts the beats on the same temporal footing. In some embodiments, signal analysis (e.g., block 303) runs through the beat rejection component block 702g twice.

In some embodiments, 702d is supplemented by 702j to aid in the detection of the beats. This can include but is not limited to electrocardiogram (ECG), pulse oximetry, or other signals that are related to the cardiac cycle.

FIG. 7C illustrates a plurality of CBFV waveforms 710, 720, 730 for signal analysis in a system for determining neurological conditions according to some embodiments.

In some embodiments, at blocks 702h and 702i, following the beat rejection at block 702g, the peaks and valleys of CBFV signals, along with the beats, are output for analysis. For example, FIG. 7C illustrates a plurality of CBFV waveforms or velocity envelopes 710, 720, 730, which may be the signals analyzed at block 303. The x-axis of the waveforms 710, 720, 730 corresponds to time and the y-axis corresponds to blood flow velocity. At block 702 the system has identified peaks and valleys of the CBFV waveforms 710, 720, 730, for example, respective peaks 712 (i.e., first peak 712a, second peak 712b, third peak 712c), 722 (i.e., first peak 722a, second peak 722b, third peak 722c), 732 (i.e., first peak 732a, second peak 732b, third peak 732c) and respective valleys 714 (i.e., first valley 714a, second valley 714b, third valley 714c), 724 (i.e., first valley 724a, second valley 724b, third valley 724c), 734 (i.e., first valley 734a, second valley 734b, third valley 734c). The relationships between the three peaks and three valleys can be different based on the underlying physiology so it is essential that these features are correctly identified.

Figure 7D:
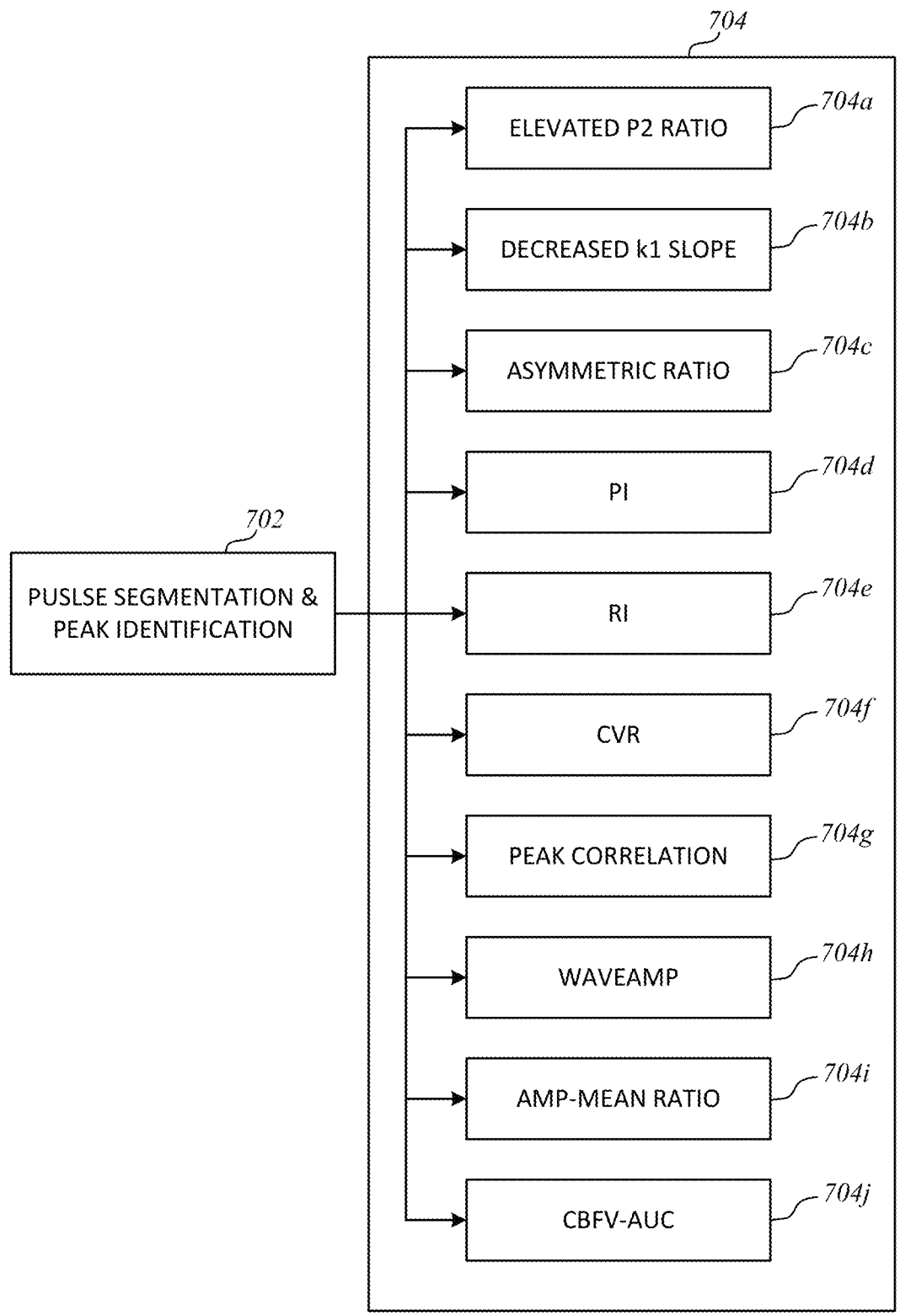
FIG. 7D illustrates a flow diagram for signal analysis including applications in a system for determining neurological conditions according to some embodiments.

FIG. 7D illustrates a flow diagram for signal analysis including applications 704 in a system for determining neurological conditions according to some embodiments.

In some embodiments, the signal analysis platform (e.g., block 303) is used to perform the analysis of the CBF or CBFV signals. The locations of the peaks and valleys described above solve the technical limitations of traditional TCD by robustly providing characterizations of these features for analysis. The following section define specific applications made available by these analyzed peaks (e.g., as analyzed in FIG. 7C). In other words, FIG. 7D illustrates examples of actionable output variables from the robust characterization of the peaks and valleys within the signal. Characterization can include but is not limited to mathematical features and manipulations such as instantaneous values, mean, derivatives, integrals, or other transforms.

Figure 7E:
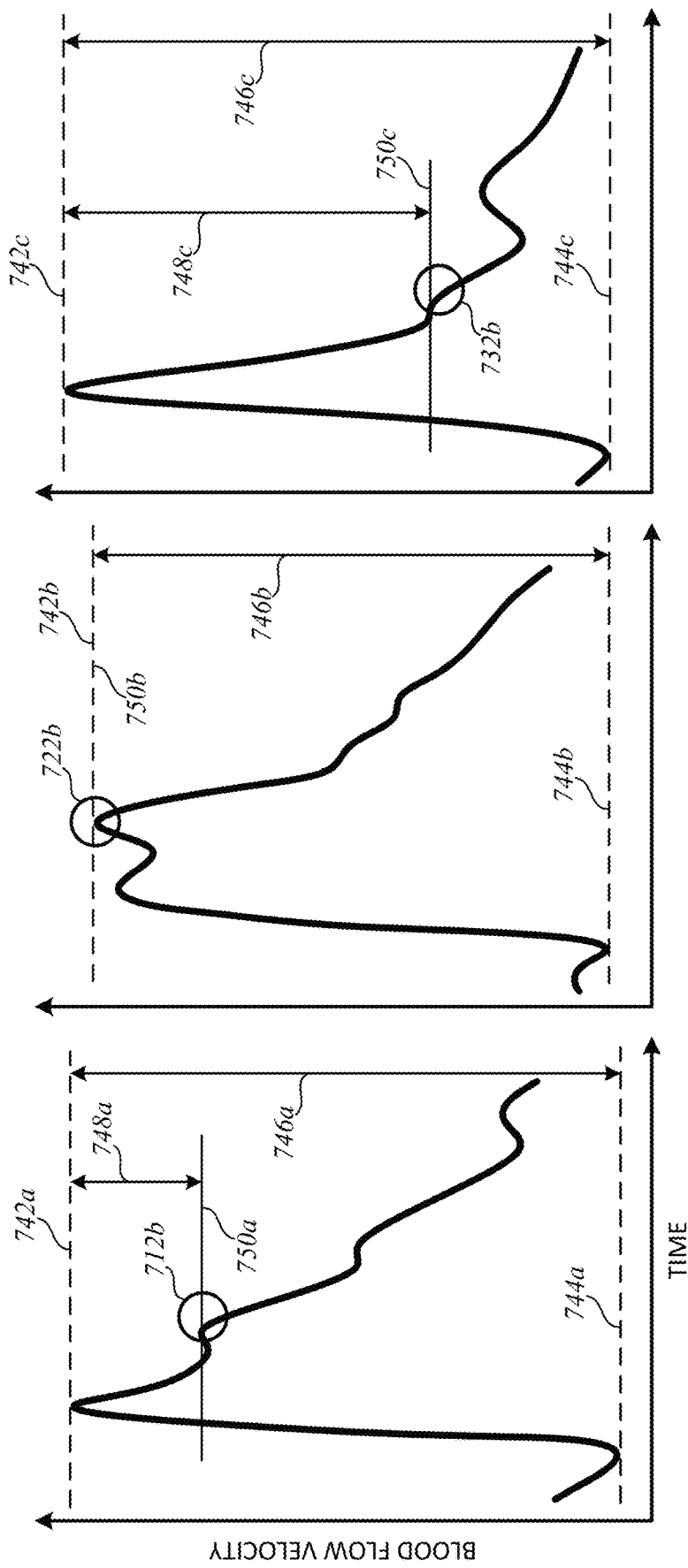
FIG. 7E illustrates a plurality of CBFV waveforms for signal analysis in a system for determining neurological conditions according to some embodiments.

FIG. 7E illustrates the plurality of CBFV waveforms 710, 720, 730 for signal analysis in a system for determining neurological conditions according to some embodiments. In some embodiments, the analysis of the CBFV waveforms 710, 720, 730 is based on elevated P2 ratio 704a. Illustrated are three examples of CBFV waveforms 710, 720, 730 with a wave amplitude (waveAmp) (defined as the maximum minus the minimum value of the individual beat) 746a, 746b, 746c along with a P2 Ratio 750a, 750b, 750c divided by waveAmp 746a, 746b, 746c. Regarding waveform 720, the P2 Ratio is 1 because the second peak 722b is the maximum value of the pulse.

In some embodiments, an application of the signal analysis platform (e.g., block 303) includes the P2 Ratio at block 704a. The P2 Ratio is a variable defined as the amplitude of the second peak (712b, 722b, 732b) divided by the wave amplitude (waveAmp=difference between peak CBFV and minimum CBFV (waveAmps 746a, 746b, 746c)) of the CBFV pulse shown. The P2 Ratio is related to the dilatation and constriction of the arterial bed which cannot be assessed with traditional TCD. According to various embodiments, this analysis provides a technical solution to the problem of assessing the distal vasculature.

Figure 7F:
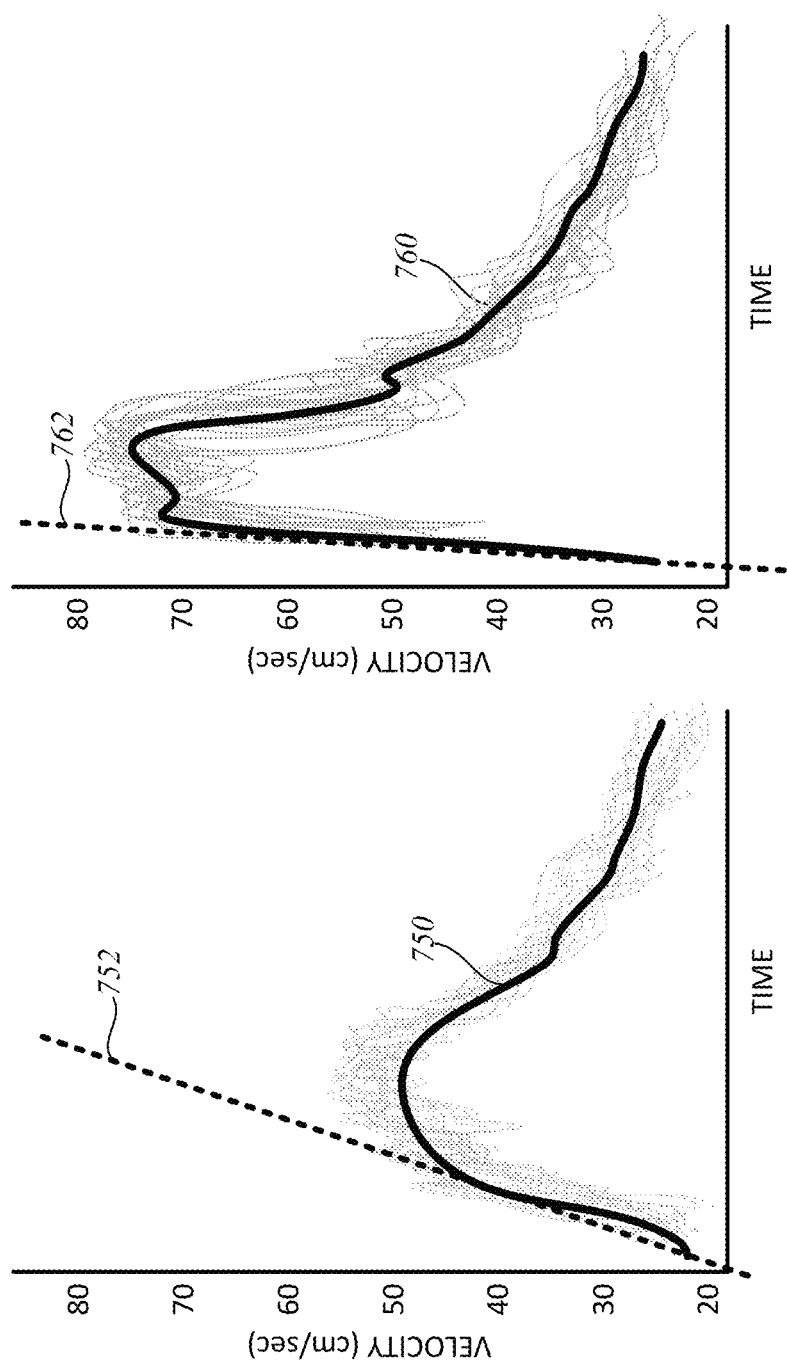
FIG. 7F illustrates a plurality of CBFV waveforms for signal analysis in a system for determining neurological conditions according to some embodiments.

FIG. 7F illustrates a plurality of CBFV waveforms 750, 760 for signal analysis in a system for determining neurological conditions according to some embodiments. In some embodiments, the analysis of the CBFV waveforms 750, 760 is based on the decreased k1 slope analysis 704b (e.g., slope between valley one and peak one). Referring to FIG. 7F, the waveform 750 includes a slope 752 and the waveform 760 includes a slope 762. The two CBFV waveforms 750 and 760 include different peak one slopes, where the decreased peak one slope is related to a specific pathology that is not capable of being quantified with traditional analysis. In some embodiments, slopes from other sections of the waveform are used such as between 722a and 722b, 722b and 722c or any other location along the waveform.

In some embodiments, an application of the signal analysis platform (e.g., block 303) includes the decreased peak one slope at block 704b. The slope can be calculated based on the locations of the peaks 712, 722, 732 and valleys 714, 724, 734 of the CBFV waveforms. The slope provides information about the compliance of the cranial vault that cannot be assessed using traditional analysis methods. As shown in FIG. 7F, there is provided an example of the waveforms 750 and 760 of a patient following stroke treatment. In the stroke patient, the slope 752 of the waveform 750 is reduced compared to the healthy peak one slope 762 of waveform 760. In some embodiments, outputs for this application are included in the slope, the change in slope based on contralateral measurements, the change in slope compared to baseline, the change in slope compared to a database of age-matched controls, and other comparisons.

In some embodiments, an application of the signal analysis platform (e.g., block 303) includes an asymmetric ratio at block 704c. The ratio between two matched vessels is taken to assess the velocity difference between the two sides and is used as the initial factor for an asymmetry index (AI), as shown in the following equation:

$$AI = \frac{IpsilaterialVelocity}{ContralaterialVelocity}$$

In some embodiments, when the AI reaches a specific threshold it can be used as a diagnostic. An example is in the case of a stroke as shown in FIG. 7F, where contralateral measurements result in an AI significantly different than 1. When AI is close to 1, it indicates that velocities are similar on each side. In some embodiments, this decision will be reported to the healthcare professional via a screen (e.g., using a number or score), a light (e.g., red, yellow, green), a sound, or physical feedback (e.g., vibration). The decision is made by comparing the calculated AI to prior measurements for the subject, for example, known measurements for different indications or data learned and stored in a database.

Additionally, AI may be calculated based on contralateral measurements of different vessel locations or different vessels when a scaling factor is used to account for an expected difference in flow, such as:

$$AI_{Diff} = \frac{IpsilaterialVelocityVessel1}{ContralaterialVelocityVessel2} \times \frac{1}{AI_{scale}}$$

Where AI_scale is calculated from a database or from prior measurements, such as:

$$AI_{scale} = \frac{IpsilaterialKnownVelocity}{ContralaterialKnownVelocity}$$

For example, if an average (e.g., previously known average) proximal MCA velocity of 55.7 cm/sec is used for the ipsilaterial velocity vessel one, and anterior cerebral artery (ACA) A1 at a depth of 65 mm, and velocity of 47.1 cm/sec is used for contralaterial velocity vessel two, then AI_scale=55.7/47.1=1.18. AI_scale then takes into account that it is expected that different vessels have different velocities so that during a diagnosis measurement, if similar velocities to known values are measured, AI_diff is still close to one which may indicate that flows are normal. If the same vessel and location is used, AI_scale effectively reduces to one which is the more intuitive case. In some embodiments, velocities of different vessels can be compared with each other, which is not intuitive.

In some embodiments, traditional measures of velocities are known to those having ordinary skill in the art, or can be measured and stored in a database for comparison. In some embodiments, a large database of exact velocities for different vessels based on demographics such as, but not limited to, age, race, and location is built and used for precise AI_scale values at any location in the cerebral vasculature.

Accordingly, in some embodiments, a technical problem is solved as traditional human operators cannot adjust the transducer with sufficient precision to repeatedly locate known vessels at specific locations. An accurate AI_scale is enabled by the kinematic mechanism, described herein, because exact locations of the vasculature can be identified based on precise, known locations from the robotic controls and then compared with each other, resulting in the use of AI_scale.

In some embodiments, an application of the signal analysis platform (e.g., block 303) includes a Pulsatility Index at block 704d. Pulsatility Index is defined as the maximum velocity (e.g., the first peak 712a, second peak 722b, first peak 732a) minus the diastolic velocity (e.g., the first valleys 714a, 724a, 734a) divided by a mean velocity, or PI=(P1−D)/V.

In some embodiments, an application of the signal analysis platform (e.g., block 303) includes a Resistance Index at block 704e. Resistance Index is a measure of distal resistance, or RI=(P1−D)/([P1+D]/2).

In some embodiments, an application of the signal analysis platform (e.g., block 303) includes cerebrovascular reactivity at block 704f. A method for computing cerebrovascular reactivity includes extracting the DC component of the velocity signal. This can be accomplished by first low-pass filtering the global signal and then picking the highest peak during a perturbation in carbon dioxide ($CO_2$) concentration. The mean velocity over the entire exam, $MV_{BL}$, is computed and the cardiovascular reactivity CVR can be found from:

$$CVR=(P_{CVR}-MV_{BL})/MV_{BL}$$

Other methods of computing CVR can also be used such as, but not limited to, incorporating end tidal $CO_2$ ($EtCO_2$).

In some embodiments, an application of the signal analysis platform (e.g., block 303) includes a peak correlation index at block 704g. The peak correlation index is defined as the Pearson's correlation coefficient between the three sub-peaks. Specifically, $Pc_{12}$ is the correlation coefficient between the first peak 712a, 722a, 732a and the second peak 712b, 722b, 732b. This allows for the tracking of a global cerebral hemodynamic environment with the sub-peaks pre-presenting different aspects of the cerebral vasculature.

In some embodiments, an application of the signal analysis platform (e.g., block 303) includes using waveAmp at block 704h. The waveAmp 746a, 746b, 746c is defined as the maximum peak of the CBFV waveforms 710, 720, 730 minus the minimum of the waveforms. In comparable system, this measure may not be fully captured in TCD and can provide additional information about the compliance of the cranial vault.

In some embodiments, an application of the signal analysis platform (e.g., block 303) includes amp-mean correlation at block 704i. The amp-mean correlation is defined as the Pearson's correlation coefficient between the waveAmp 746a, 746b, 746c and the mean of the CBFV waveform 710, 720, 730. In some embodiment, a feature tied to an automated mechanism to track the moment-to-moment cerebral dynamics will lead to better management of several neurological conditions.

In some embodiments, an application of the signal analysis platform (e.g., block 303) includes CBFV AUC, or the area under the CBFV envelope at block 704j. In some embodiments, AUC is computed by calculating the integral of the CBFV waveform.

In some embodiments, the above-described applications or variables are examples of utilization of the signal analysis platform (e.g., block 303), which can be output to a screen or used for additional data processing following the automation of the signal optimization and analysis. Additionally, these features are tied to the automated signal acquisition and optimization. Accordingly, the system described herein can be used for a number of different neurological conditions including, but not limited to, TBI, stroke, dementia, headache, tumor, Parkinson's Disease, or other psychological/medical conditions impacting cerebral blood flow. In some embodiments, systems are used for diagnosis, monitoring, and treatment.

In further embodiments, systems described herein can be used for various application including, but not limited to, use of functional TCD for non-verbal communication, vascular identification of an individual (e.g., mapping), cerebral therapy, intraoperative surgery, anesthesia monitoring, physical performance, anticoagulant monitoring, and drug testing. In some embodiments, cerebral therapy includes using ultrasound in physical therapy for the breakdown of scar tissue and stimulation of blood flow. With a precision robot and location technology this same ultrasound can be used for stimulation of blood flow to specific areas of the brain for helping, for example, depression, TBI, stroke, and the like. In further embodiments, cerebral therapy includes using systems as energy therapy (e.g., as a substitute for caffeine). In some embodiments, intraoperative surgery includes several types of surgery including, but not limited to, carotid endarterectomy, verapimil injection, shunt placement for normal pressure hydrocephalus (NPH), hydrocephalus monitoring, and any surgery where cerebral perfusion is monitored (e.g., anesthesia). In some embodiments, anesthesia monitoring includes determining a correct amount of anesthesia and tracking an individual's level of sedation. In some embodiments, physical performance includes tracking cerebral health. In some embodiments, anticoagulant monitoring includes monitoring emboli over time to help inform a doctor on how to titrate drugs. In some embodiments, drug testing includes monitoring cerebral vascular response to specific drugs (e.g., monitoring alertness via blood flow).

The embodiments described herein have been described with reference to drawings. The drawings illustrate certain details of specific embodiments that implement the systems, methods and programs described herein. However, describing the embodiments with drawings should not be construed as imposing on the disclosure any limitations that may be present in the drawings. The present embodiments contemplate methods, systems and program products on any machine-readable media for accomplishing its operations. The embodiments may be implemented using an existing computer processor, or by a special purpose computer processor incorporated for this or another purpose or by a hardwired system.

As noted above, embodiments within the scope of this disclosure include program products comprising non-transitory machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments have been described in the general context of method steps which may be implemented in some embodiments by a program product including machine-executable instructions, such as program code, for example in the form of program modules executed by machines in networked environments. Generally, program modules include routines, programs, objects, components, data structures, etc. that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

As previously indicated, embodiments may be practiced in a networked environment using logical connections to one or more remote computers having processors. Those skilled in the art will appreciate that such network computing environments may encompass many types of computers, including personal computers, hand-held devices, multiprocessor systems, microprocessor-based or programmable consumer electronics, network PCs, minicomputers, mainframe computers, and so on. Embodiments may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An example system for implementing the overall system or portions of the embodiments might include general purpose computing devices in the form of computers, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules and other data for the computer. It should also be noted that the word "terminal" as used herein is intended to encompass computer input and output devices. Input devices, as described herein, include a keyboard, a keypad, a mouse, joystick or other input devices performing a similar function. The output devices, as described herein, include a computer monitor, printer, facsimile machine, or other output devices performing a similar function.

It should be noted that although the diagrams herein may show a specific order and composition of method steps or blocks, it is understood that the order of these steps or blocks may differ from what is depicted. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative embodiments. Accordingly, all such modifications are intended to be included within the scope of the present disclosure as defined in the appended claims. Such variations will depend on the software and hardware systems chosen and on designer choice. It is understood that all such variations are within the scope of the disclosure. Likewise, software and web implementations of the present disclosure could be accomplished with standard programming techniques with rule based logic and other logic to accomplish the various database searching steps, correlation steps, comparison steps and decision steps.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principals of the disclosure and its practical application to enable one skilled in the art to utilize the various embodiments and with various modifications as are suited to the particular use contemplated. Other substitutions, modifications, changes and omissions may be made in the design, operating conditions and arrangement of the embodiments without departing from the scope of the present disclosure as expressed in the appended claims.

According to various embodiments, a five actuated degree of freedom (DOF) kinematic mechanism is used that fully automates evaluation of the temporal window quality and can rediscover the temporal window even after complete loss of signal. To those skilled in the art, a distinction exists between an active, or actuated degree of freedom, on the one hand, and a passive degree of freedom on the other hand. An active, or actuated degree of freedom includes an actuator, such as for example, a motor. A passive degree of freedom does not require such an actuator. In this specification, if the term "degree of freedom" is used without being qualified as passive, the degree of freedom discussed is meant to be an active or actuated degree of freedom. In some embodiments, a computer generates commands and directs the mechanism to translate and reorient the probe along the surface of the head until a candidate signal is located. Once located, the probe is reoriented to increase signal strength. In some embodiments, reducing the search time of the automated system to discover the temporal window is accomplished by aligning the mechanism and probe at a known anatomical feature, such as the zygomatic arch. In some embodiments, the alignment is performed with a visual window guide for the user to place the probe at an initial starting point along the zygomatic arch between ear and the eye.

In some embodiments, after the probe is properly aligned, the stiffness of the probe is held normal to the surface at a high enough level to keep the probe seated, but low enough so to be comfortable to the user as the probe moves in and out following the surface of the head. In some embodiments, the X and Y axes can retain a higher servo stiffness in order to maintain precision control of probe location. In some embodiments, because the normal force of the probe is determined by the Z-axis stiffness, the sliding force encounter by the X and Y axes will be limited to a comfortable level, and the probe can be directed to perform a search for the TCD window. In some embodiments, if the orientation of the probe needs to be changed, the orientation stiffnesses can be increased via software.

In some embodiments, the kinematic mechanism of the probe includes five motor, or actuated, degrees of freedom, $Q=J1, J2, J3, J4, J5$ (i.e., motor or joint space) to effect five degrees of freedom in position and orientation $X=\{x, y, z, pan, tilt\}$ (i.e., task space). As such, the forward kinematics may be written as the relationship between motor coordinates and probe coordinates: $X=fwd\_kin(Q)$, where $fwd\_kin$ is a function representing a series of equations based on the mechanism design and typically analyzed by Denavit-Hartenberg parameters.

In some embodiments, placement of the TCD probe is specified via the inverse kinematics with either an analytic inverse solution: $Q=inv\_kin(X)$, or by using a numerical differential such as the Jacobian inverse solution $dQ_{cmd}(n)=J^{-1}(X_{err}(n))$, where $J$ is the Jacobian, relating differential motion of the motors to the differential motion of the probe, $X_{err}(n)$ is the probe position and orientation error at time n, and $dQ_{cmd}(n)$ is the differential motor command at time n. For mechanisms with more motor or actuated degrees of freedom than probe position and orientation coordinates being controlled, the kinematics are called redundant, and such mechanisms have more than five motors. For redundant mechanisms, the inverse kinematics changes from the inverse Jacobian to the Moore-Penrose pseudo-inverse (or other generalized inverse) of the Jacobian, $dQ_{cmd}(n)=J^{\dagger}(X_{err}(n))$.

Figure 8:
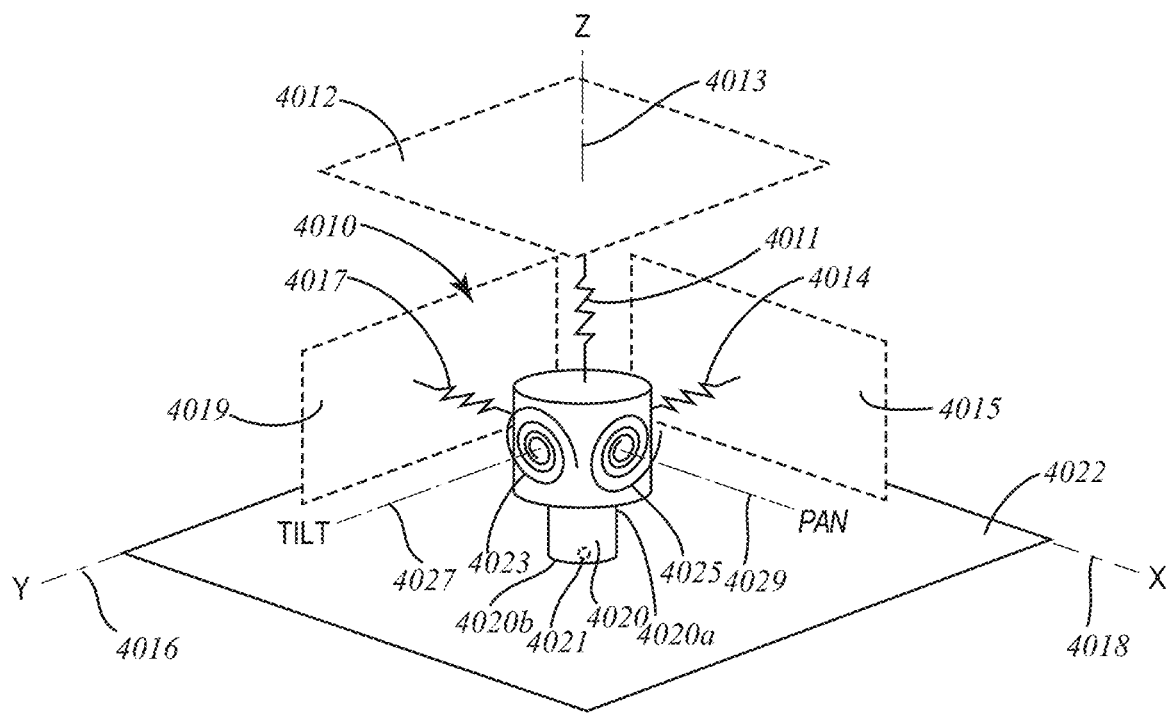
FIG. 8 is a diagram of a virtual support structure for manipulating a medical probe, according to an exemplary embodiment.

FIG. 8 is a diagram of a model of a virtual support structure 4010 for a probe 4020, according to an exemplary embodiment. The support structure 4010 is configured to position the probe 4020 relative to a target surface 4022. In some embodiments, the probe 4020 is a medical probe, such as a medical probe for use with a transcranial Doppler (TCD) apparatus to emit ultrasound wave emissions directed to the target surface 4022. In other embodiments, the probe 4020 is configured to emit other types of waves during operation, such as, but not limited to, infrared waves, x-rays, and so on. In various embodiments, the probe 4020 may be a transcranial color-coded sonography (TCCS) probe, or it may be an array such as a sequential array or phased array which emits waves.

In some embodiments, the probe 4020 has a first end 4020a and a second end 4020b. In some embodiments, the first end 4020a interfaces with the support structure 4010. In some embodiments, the second end 4020*b* contacts the target surface 4022 on which the probe 4020 operates at a contact point 4021. In some embodiments, the second end 4020*b* is a concave structure such that the contact point 4021 is a ring shape (i.e., the second end 4020*b* contacts the target surface 4022 along a circular outer edge of the concave second end 4020*b*). The support structure 4010 controls the relative position of the probe 4020 (e.g., z-axis force, y-axis force, x-axis force, normal alignment, etc.). The support structure 4010 is shown as a virtual structure including a first virtual spring 4011 coupled between the probe 4020 and a virtual surface 4012 and exerting a force along a z-axis 4013, a second virtual spring 4014 coupled between the probe 4020 and a virtual surface 4015 and exerting a force along a y-axis 4016, and a third virtual spring 4017 coupled between the probe 4020 and a virtual surface 4019 and exerting a force along the x-axis 4018. The virtual support structure 4010 further includes a torsional spring 4023 exerting a torque about a tilt axis 4027 and a second torsional spring 4025 exerting a torque about a pan axis 4029. In some embodiments, the virtual support structure 4010 includes other virtual elements, such as virtual dampers (not shown). Virtual dampers represent elements that improve the stability of the system and are useful for tuning the dynamic response of the system. The virtual, or apparent inertia of the probe, can also be set to have isotropic or anisotropic properties, by modeling and feed forwarding out the effects of mechanism inertia, motor rotational inertial, centripetal/centrifugal effects, and replacing them with arbitrary inertial properties, within the physical performance limits of the device.

The virtual support structure 4010 represents a variety of mechanical structures that may be utilized to position the probe 4020 relative to the target surface 4022, as described in more detail below. In some embodiments, the second end 4020*b* of the probe 4020 is caused to contact a relatively delicate surface, such as the skin of the patient or subject. The support structure is configured to adjust its stiffness (e.g., impedance, compliance, etc.) to provide variable linear forces and rotational forces on the probe 4020, and may be relatively stiff in some directions and may be relatively compliant in other directions. For example, the support structure 4010 may apply minimal force and may be relatively compliant along the z-axis 4013 to minimize forces applied to the patient or subject (e.g., if the patient or subject moves relative to the support structure) in a direction generally normal to the target surface 4022 and may be relatively stiff along the y-axis 4016 and the x-axis 4018 to improve the positional accuracy and precision of the probe 4020 along a plane generally parallel to the target surface 4022. Further, the desired stiffness of the support structure 4010 along various axes may vary over time, depending on the task at hand. For example, the support structure may be configured to be relatively compliant in scenarios in which the support structure 4010 is being moved relative to the patient or subject (e.g., during initial set-up of the probe structure, removal of the probe structure, etc.), or when it is advantageous to be relatively free-moving (e.g., during maintenance/cleaning, etc.), and may be configured to be relatively stiff, in some directions, in scenarios in which accuracy and precision of the positioning of the probe 4020 is advantageous (e.g., during the TCD procedure or other procedure being performed with the probe 4020).

As described in more detail below, a kinematic model of the support structure 4010 can be utilized to calculate the relationship between the forces applied to the target surface 4022 by the probe 4020 and the forces (e.g., torques) applied by actuators actuating the support structure 4010. The forces applied to the target surface 4022 by the probe 4020 in the idealized system can therefore be determined theoretically, without direct force sensing, thereby eliminating the need for a load cell disposed in-line with the probe 4020 and/or a force torque sensor coupled to the probe 4020 to maintain appropriate contact force that maximizes signal quality. In a physical system, static friction, along with other unmodeled physical effects, may introduce some uncertainty.

Figure 9:
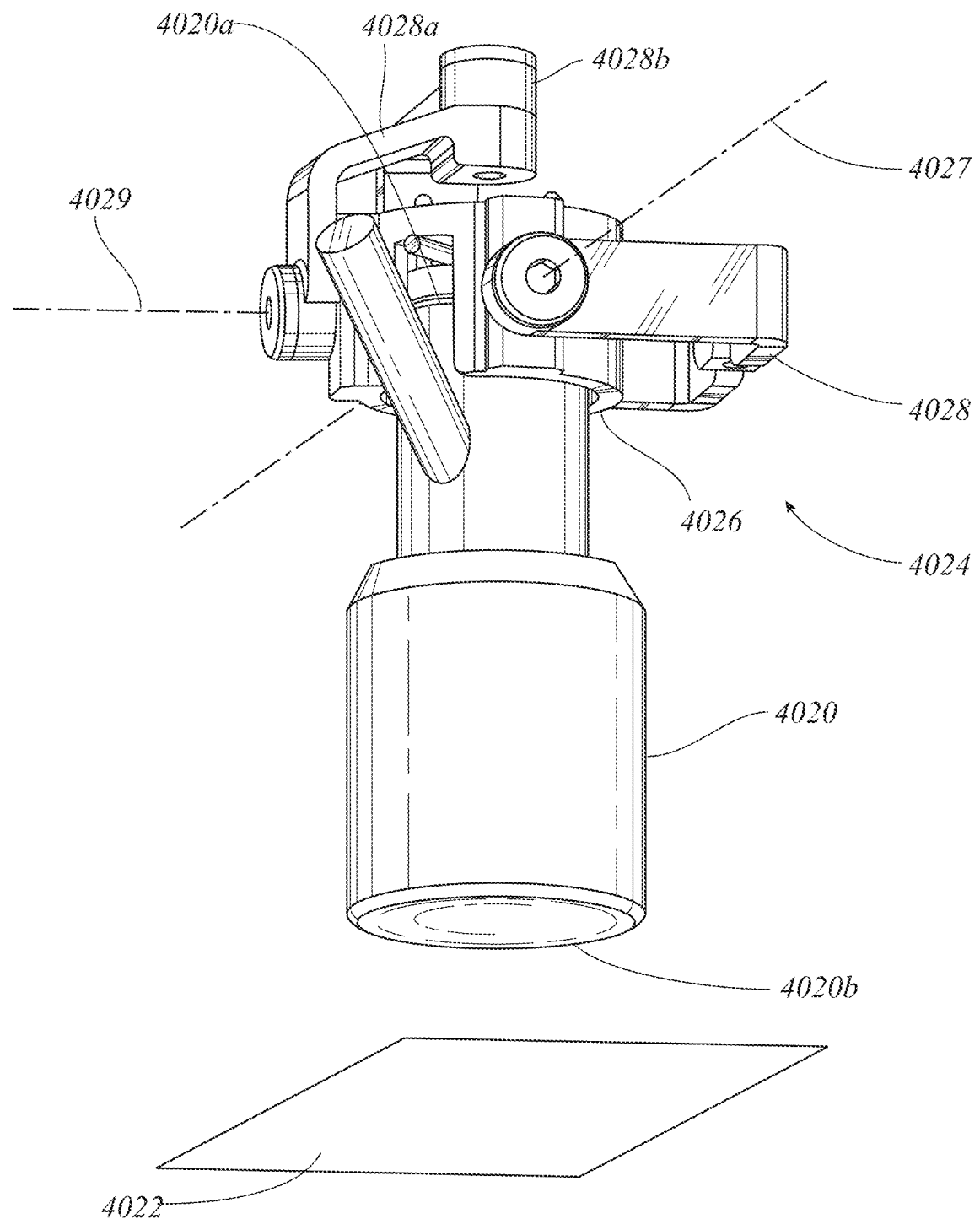
FIG. 9 is an perspective view of a medical probe and a gimbal structure, according to an exemplary embodiment.

Referring to FIG. 9, the probe 4020 is shown according to an exemplary embodiment mounted to a portion of a support structure, shown as a gimbal structure 4024, which can rotate about multiple axes, at the first end 4020*a*. The gimbal structure 4024 includes a first frame member 4026 that is able to rotate about the tilt axis 4027 and a second frame member 4028 that is able to rotate about the pan axis 4029. The target surface 4022 may be uneven (e.g., non-planar). The gimbal structure 4024 allows the probe 4020 to be oriented such that it is normal to the target surface 4022 at the contact point 4021.

Figure 10:
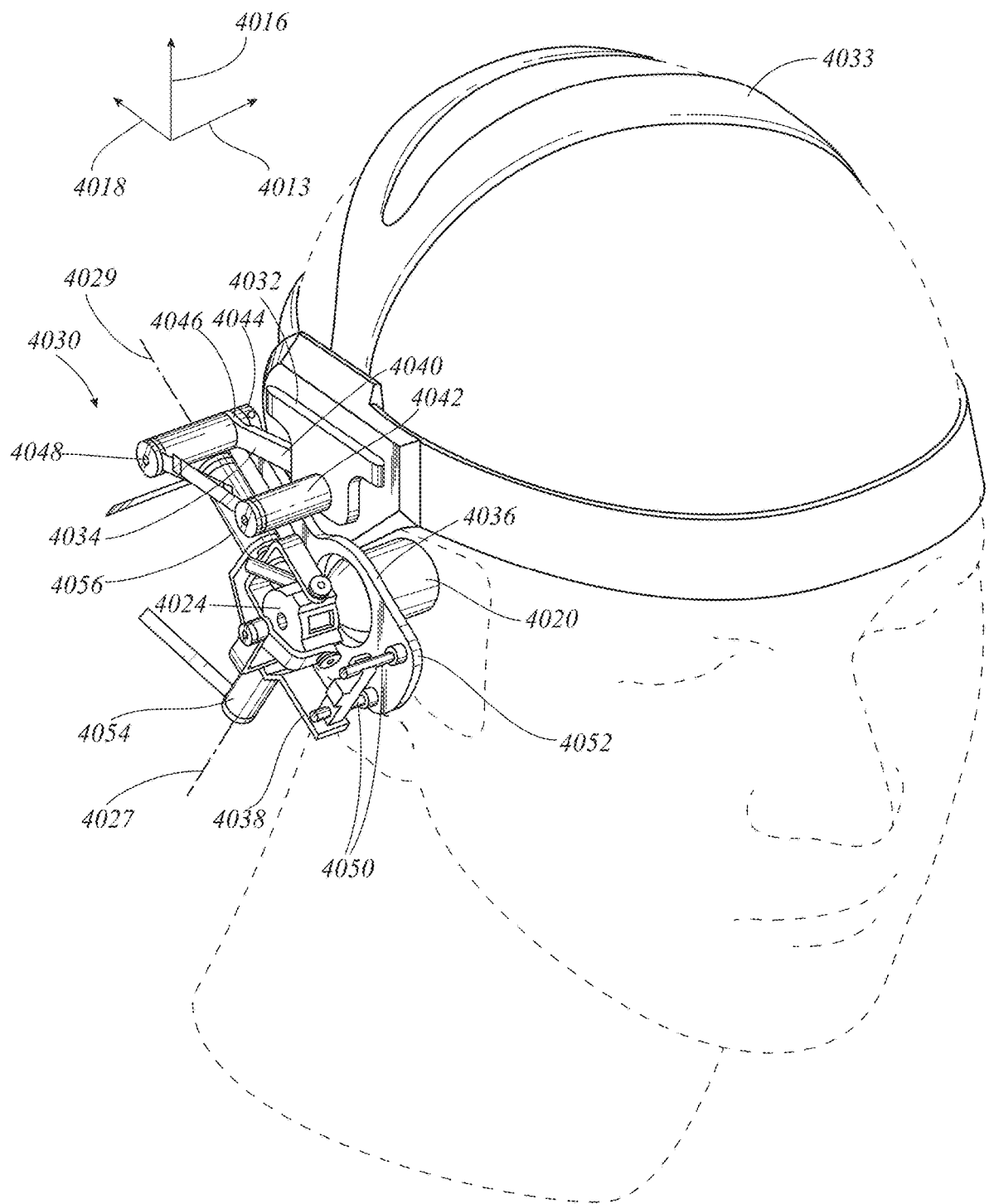
FIG. 10 is a perspective view of a two-link revolute support structure for the medical probe of FIG. 9, according to an exemplary embodiment.
Figure 11:
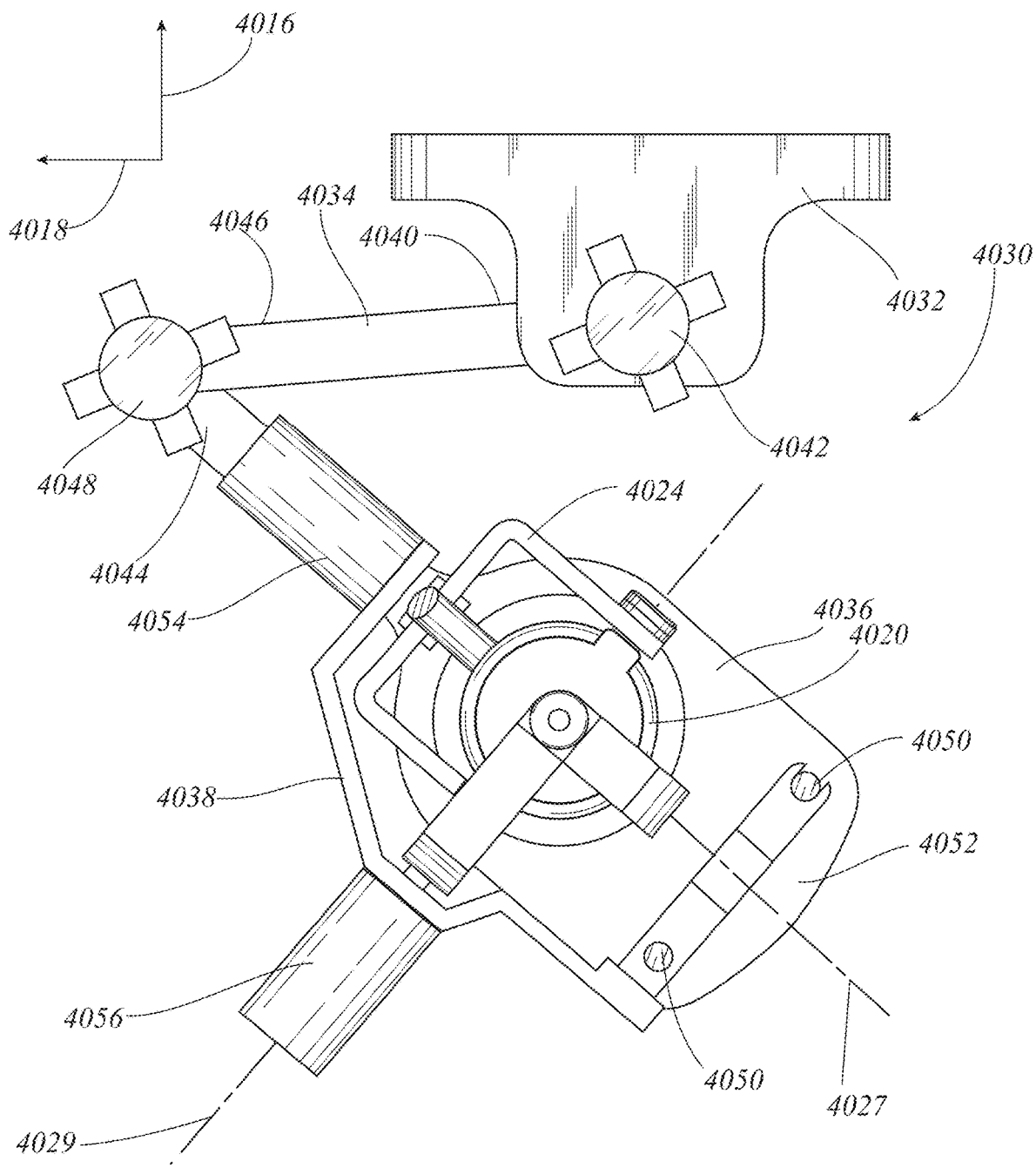
FIG. 11 is front elevation view of the support structure of FIG. 10.
Figure 12:
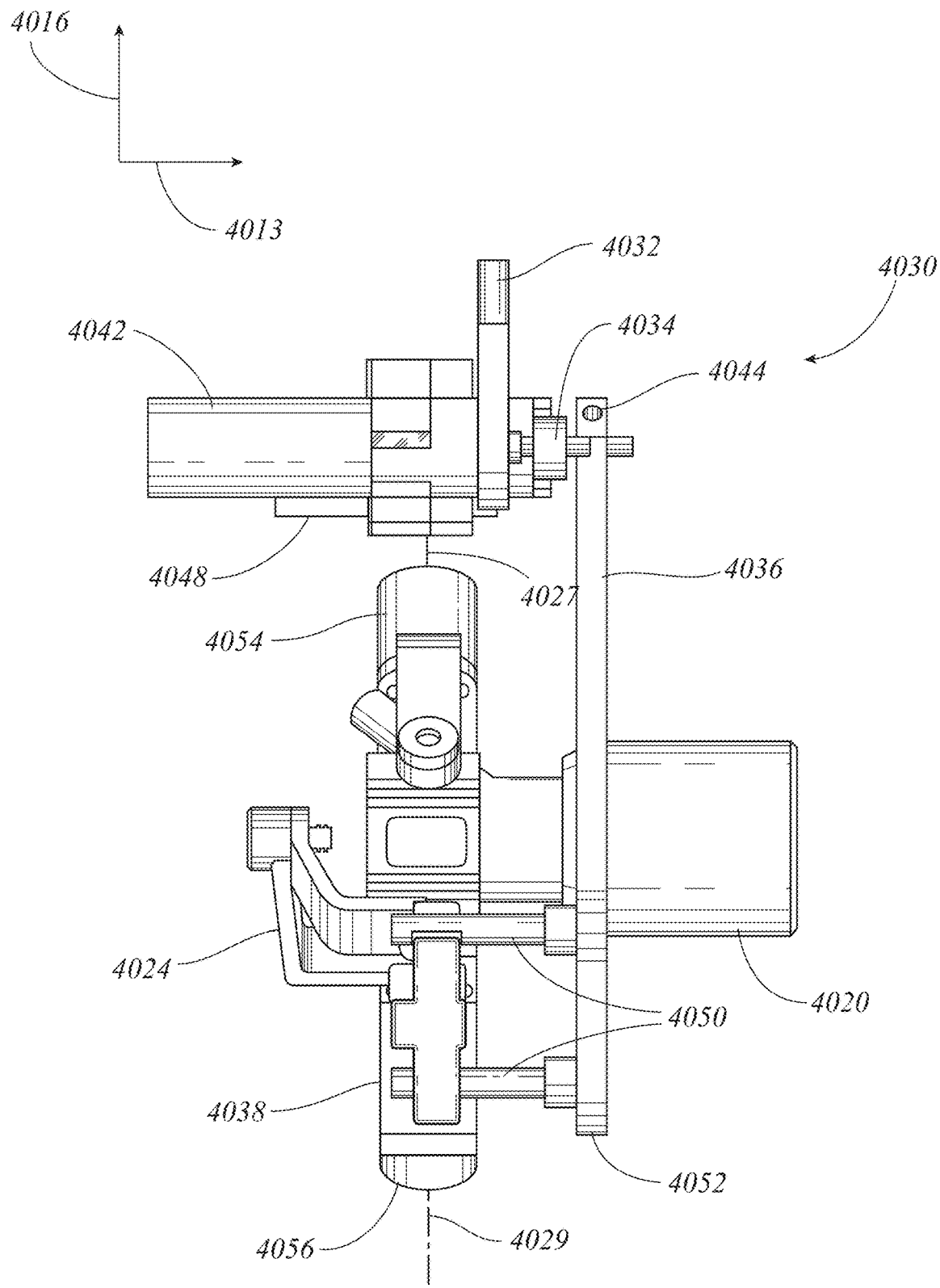
FIG. 12 is a right side elevation view of the support structure of FIG. 10.

Referring now to FIGS. 10-12, a support structure 4030 for the probe 4020 is shown according to an exemplary embodiment as a two-link revolute (e.g., revolute-revolute) robot. The support structure 4030 includes a first frame member 4032, a second frame member 4034, a third frame member 4036, a fourth frame member 4038, and the gimbal structure 4024. The first frame member 4032 is configured to be a static member. The first frame member 4032 may, for example, be mounted to a halo or headset 4033 worn on the patient's or subject's head or other structure that attaches the first frame member 4032 to the patient or subject or fixes the position of the first frame member 4032 relative to the patient or subject. The probe 4020 is configured to emit energy into the head of the patient or subject.

Referring to FIG. 10, the second frame member 4034 is a link configured to rotate about the z-axis 4013. The z-axis 4013 is generally perpendicular to the surface of the head. A first end 4040 of the second frame member 4034 is coupled to the first frame member 4032. According to an exemplary embodiment, the rotation of the second frame member 4034 relative to the first frame member 4032 is controlled by an actuator 4042, shown as an electric motor and gearbox that is attached through the first frame member 4032. Actuator 4042 acts as a perpendicular translation actuator for translating the probe along a perpendicular axis generally perpendicular to the surface of the head.

The third frame member 4036 is a link configured to rotate about the z-axis 4013. A first end 4044 of the third frame member 4036 is coupled to a second end 4046 of the second frame member 4034. According to an exemplary embodiment, the rotation of the third frame member 4036 relative to the second frame member 4034 is controlled by an actuator 4048, shown as an electric motor and gearbox that is attached through the second frame member 4034.

The fourth frame member 4038 is configured to translate along the z-axis 4013 (e.g., in and out, in and away from the head, etc.). According to an exemplary embodiment, the fourth frame member 4038 slides along rail members 4050 that are fixed to a second end 4052 of the third frame member 4036. The position of the fourth frame member 38 relative to the third frame member 4036 is controlled by an actuator, such as an electric motor and a lead screw (not shown for clarity).

The gimbal structure 4024 and the probe 4020 are mounted to the fourth frame member 4038. The gimbal structure 4024 controls the orientation of the probe 4020 about the tilt axis 4027 and the pan axis 4029 (e.g., pan and tilt). The position of the probe 4020 about the tilt axis 4027 is controlled by an actuator 4054, shown as an electric motor and gearbox. Actuator 4054 acts as a rotation actuator to rotate the probe. The position of the probe 4020 about the pan axis 4029 is controlled by an actuator 4056, shown as an electric motor and gearbox. Actuator 4056 acts as a rotation actuator to rotate the probe. In one embodiment, the rotation of the probe 4020 about the tilt axis 4027 and the pan axis 4029 is different than the z-axis 4013, regardless of the rotation of the frame members 4034 and 4036.

The probe 4020 is able to move on the x-y plane, i.e., the translation plane, which is defined by the x-axis 4018 and the y-axis 4016, through the rotation of the second frame member 4034 and the third frame member 4036. The probe 4020 is able to move along the z-axis 4013, i.e., the translation axis, through the translation of the fourth frame member 4038. Further, the probe 4020 is able to rotate about tilt axis 4027 and the pan axis 4029 through the gimbal structure 4024. Combining these five actuated degrees of freedom allows the position and orientation of the probe 4020 relative to the target surface 4022 to be completely described and controlled, discounting rotation about a third axis that is orthogonal to the pan axis 4029 and the tilt axis 4027.

According to an exemplary embodiment, the actuators utilized to position the support structure 4030 are servo motors. The use of servo motors to control the support structure allow for a more precise control, compared to a stepper motor, for the torque output, rotational position, and angular speed of the motor, as well as the corresponding position of the probe 4020 and the interaction between the probe 4020 and the target surface 4022. Of course, other suitable motors known to those of ordinary skill in the art could also be used.

Figure 13:
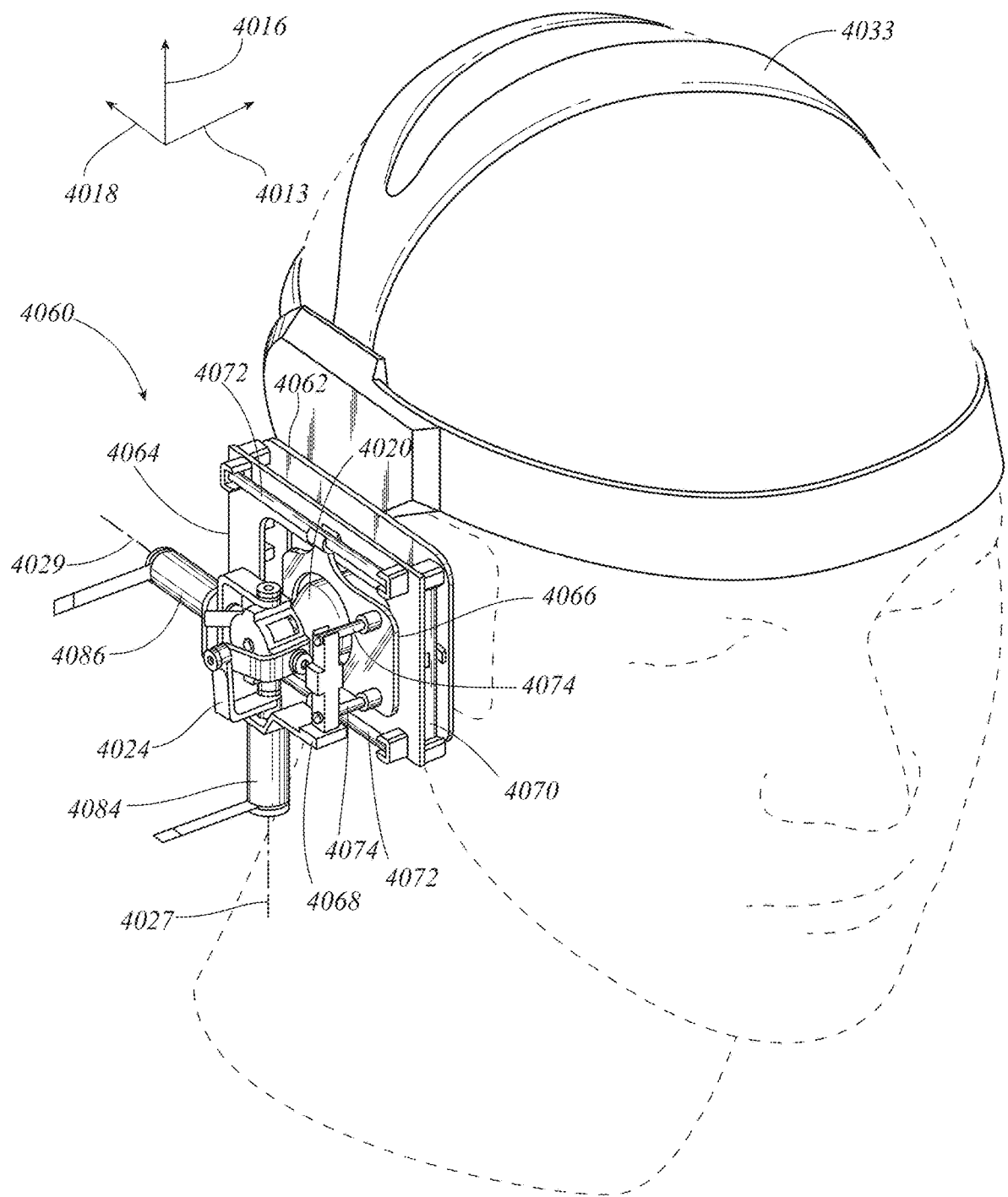
FIG. 13 is a perspective view of a prismatic support structure for the medical probe of FIG. 9, according to an exemplary embodiment.
Figure 14:
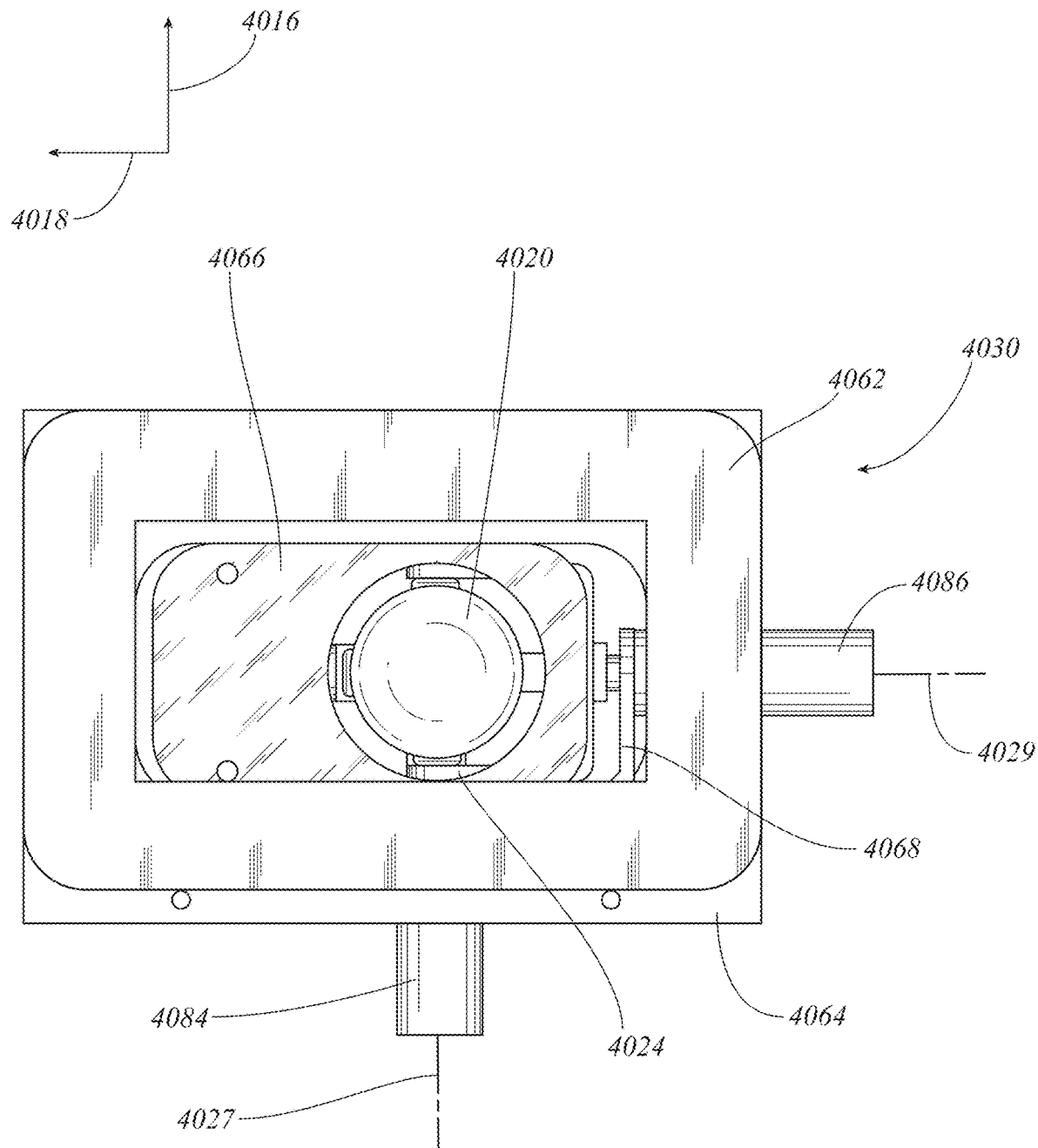
FIG. 14 is front elevation view of the support structure of FIG. 13.
Figure 15:
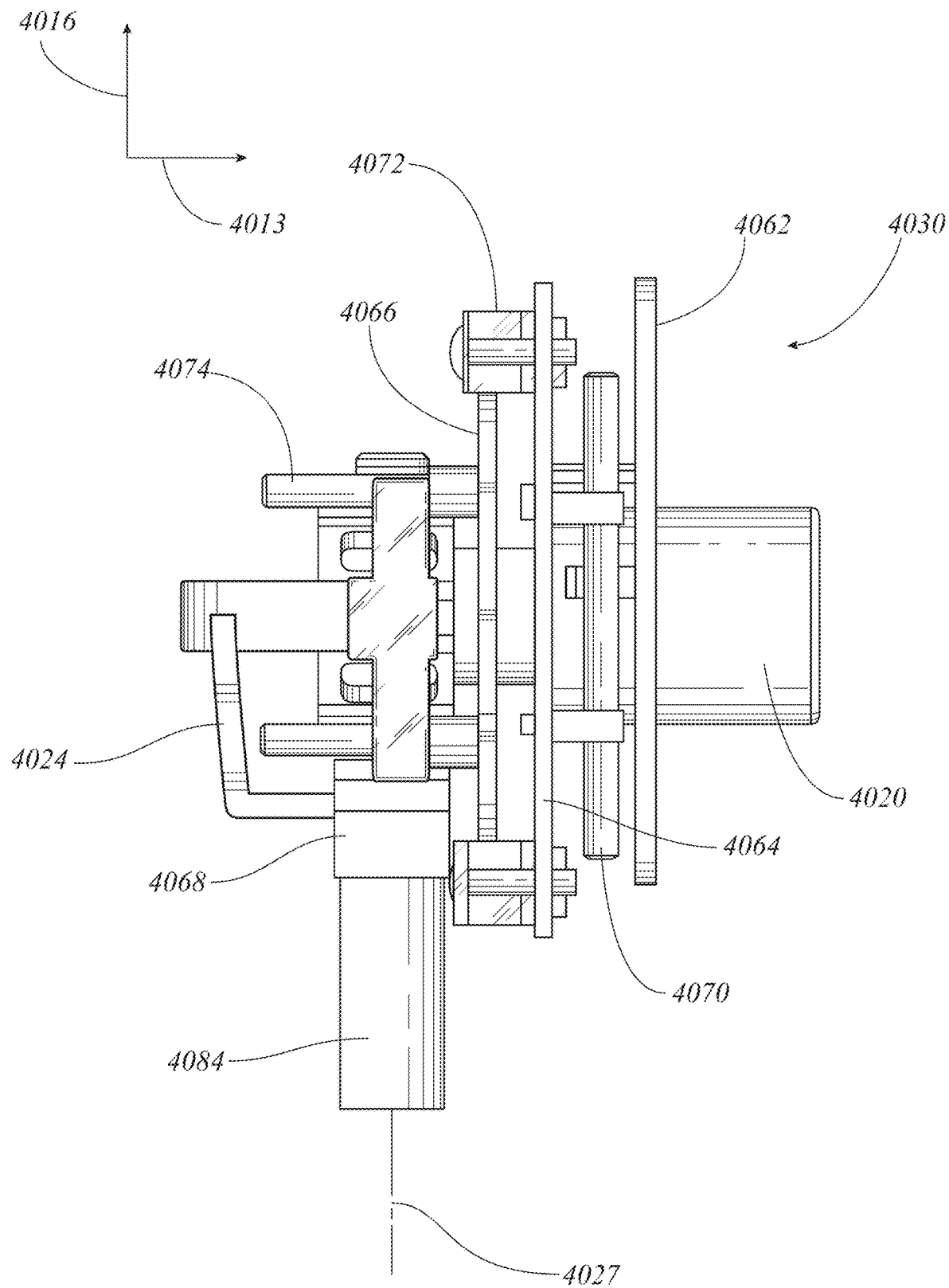
FIG. 15 is a right side elevation view of the support structure of FIG. 13.

Referring now to FIGS. 13-15, a support structure 4060 for the probe 4020 and the gimbal structure 4024 is shown according to another exemplary embodiment as a prismatic (e.g., Cartesian, rectilinear, etc.) robot. FIG. 13 illustrates an exemplary Prismatic-Prismatic-Prismatic robot. The support structure 4060 includes a first frame member 4062, a second frame member 4064, a third frame member 4066, a fourth frame member 4068, and the gimbal structure 4024. The first frame member 4062 is configured to be a static member. The first frame member 4062 may, for example, be mounted to a halo or headset 4033 worn on the patient's or subject's head or other structure that fixes the position of the first frame member 4062 relative to the patient or subject.

The second frame member 4064 is configured to translate along the y-axis 4016 (e.g., up and down, bottom of ear to top of ear, etc). According to an exemplary embodiment, the second frame member 4064 slides along rail members 4070 that are fixed to the first frame member 4062. The position of the second frame member 4064 relative to the first frame member 4062 is controlled by an actuator, such as an electric motor and a lead screw (not shown for clarity).

The third frame member 4066 is configured to translate along the x-axis 4018 (e.g., forward and backward, ear to eye, etc.). According to an exemplary embodiment, the third frame member 4066 slides along rail members 4072 that are fixed to the second frame member 4064. The rail members 4072 are orthogonal to the rail members 4070. The position of the third frame member 4066 relative to the second frame member 4064 is controlled by an actuator, such as an electric motor and a lead screw (not shown for clarity).

The fourth frame member 4068 is configured to translate along the z-axis 4013 (e.g., in and out, in and away from the head, etc.). According to an exemplary embodiment, the fourth frame member 4068 slides along rail members 4074 that are fixed to the third frame member 4066. The position of the fourth frame member 4068 relative to the third frame member 4066 is controlled by an actuator, such as an electric motor and a lead screw (not shown for clarity).

The gimbal structure 4024 and the probe 4020 are mounted to the fourth frame member 4068. The gimbal structure 4024 controls the orientation of the probe 4020 about the tilt axis 4027 and the pan axis 4029 (e.g., tilt and pan). The position of the probe 4020 about the tilt axis 4027 is controlled by an actuator 4084, shown as an electric motor and gearbox. The position of the probe 4020 about the pan axis 4029 is controlled by an actuator 4086, shown as an electric motor and gearbox.

The probe 4020 is able to move on the x-y plane through the translation of the second frame member 4064 and the third frame member 4066, move along the z-axis 4013 through the translation of the fourth frame member 4068, and rotate about tilt axis 4027 and the pan axis 4029 through the gimbal structure 4024. Combining these five actuated degrees of freedom allows the position and orientation of the probe 4020 relative to the target surface 4022 to be completely described and controlled, discounting rotation about a third axis that is orthogonal to the pan axis 4029 and the tilt axis 4027.

A kinematic model can be developed for any embodiment of a support structure for the probe 4020 to determine the relationship between the forces exerted at the probe 4020 and the forces applied by the actuators controlling the support structure.

A stiffness matrix for the support structure is first determined. The stiffness matrix is determined using a multitude of variables, including the physical properties of the support structure (e.g., the geometry of the frame members, the stiffness of the individual frame members etc.), the system stiffness along the chosen coordinate system axis, and a velocity-based term for system damping. According to an exemplary embodiment, the desired stiffness of the support structure is defined in the z direction ($K_z$), the y direction ($K_y$), and the x direction ($K_x$) (e.g., as represented by the virtual springs 4011, 4014, and 4017 in FIG. 8), and about the pan axis 4029 ($K\omega_x$) and about the tilt axis 4027 ($K\omega_y$) (e.g., as represented by the virtual torsional springs 4023 and 4025 in FIG. 8). As described above, in some embodiments, the virtual stiffnesses vary over time and are based on the task being accomplished with the probe 4020. For example, stiffness in the y direction and in the x direction may have a lower bound corresponding to a relatively low lateral stiffness during a set-up or removal procedure, in which the support structure is configured to be relatively compliant; and an upper bound corresponding to a relatively high stiffness during a scanning procedure, in which the support structure is configured to be relatively stiff, allowing for a more accurate positioning of the probe 4020. Likewise, stiffness in the z direction may have a lower bound corresponding to a relatively low stiffness during initial positioning of the probe 4020 in the z direction, in which the support structure is configured to be relatively compliant to allow the probe 4020 to self-align (e.g., to minimize discomfort for the patient or subject); and an upper bound corresponding to a relatively high stiffness during a scanning procedure, in which the support structure is configured to more stiff, to overcome friction forces between the probe 4020 and the target surface 4022 and to maintain the orientation of the probe 4020. Further, rotational stiffnesses about the y axis and the x axis may have a lower bound corresponding to a relatively low rotational stiffness during positioning of the probe 4020 to conform to the contour of the target surface 4022 (e.g., the head of the patient or subject), in which the support structure (e.g., the gimbal structure 4024) is configured to be relatively compliant (e.g., to minimize discomfort for the patient or subject); and an upper bound corresponding to a relatively high rotational stiffness when a more accurate positioning (e.g., panning, tilting, etc.) of the probe 4020 is desired.

A force vector is then derived using the following equation:

$$\vec{F} = K\Delta\vec{x} \quad \text{(Eq. 1)}$$

where K is the stiffness matrix and $\Delta\vec{x}$ is the vector of the difference of the desired and actual translational position in the x, y, and z directions and rotational position about the x-axis 404018 and y-axis 16 of the probe 4020.

The force applied by the actuators (e.g., the torque applied by rotational actuators) controlling the position of the support structure may then be determined using the following equation:

$$\tau = J^T \vec{F} \quad \text{(Eq. 2)}$$

where $J^T$ is the Jacobian transpose determined by the kinematics of the specific support structure. The Jacobian is the differential relationship between the joint positions and the end-effector position and orientation (e.g., the position of the probe 4020). The joint positions are either in units of radians (e.g., for rotational joints), or in units of length (e.g., for prismatic or linear joints). The Jacobian is not static and changes as the support structure position articulates.

Figure 16:
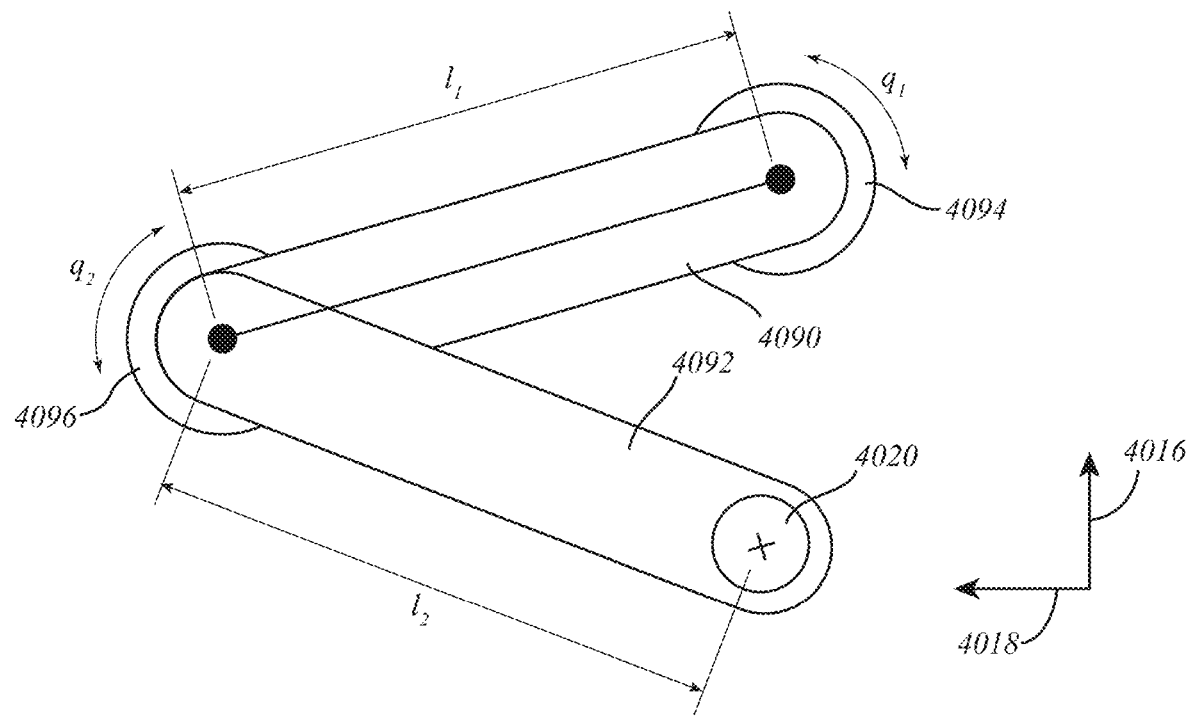
FIG. 16 is a schematic front view diagram of the support structure of FIG. 10.
Figure 17:
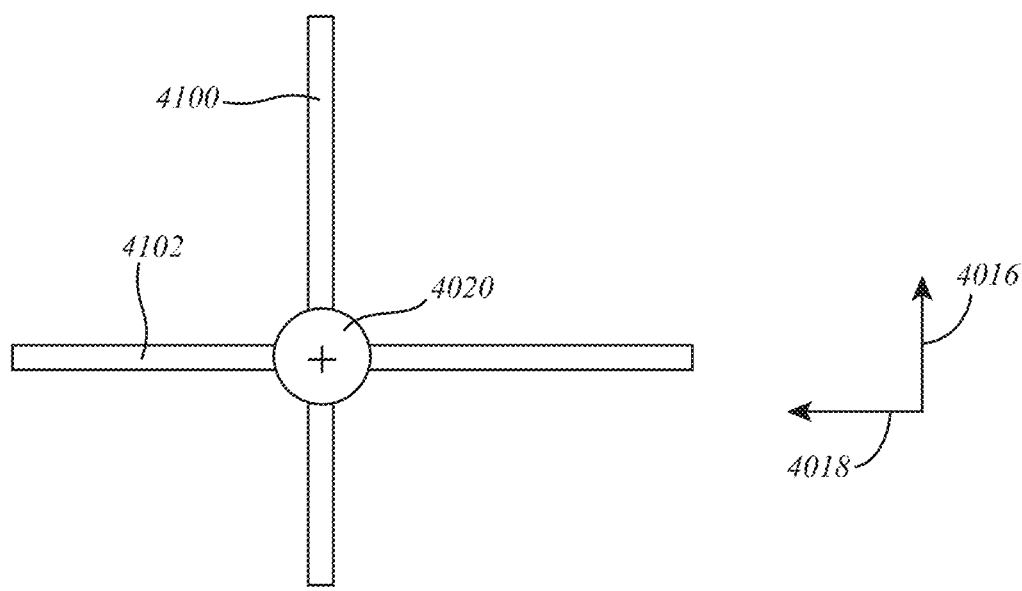
FIG. 17 is a schematic front view diagram of the support structure of FIG. 13.

Referring now to FIG. 16, a schematic front view diagram of the support structure 4030 is shown. The second frame member 4034 is represented by a first link 4090, having a length $l_1$. The first link 4090 is articulated by a rotary actuator 4094, the rotation of which is shown as $q_1$. The third frame member 4036 is represented by a second link 4092, having a length $l_2$. The second link 4092 is articulated by a rotary actuator 4096, the rotation of which is shown as $q_2$. The actuators 4094 and 4096 move the probe 4020 in the x-y plane.

The forward kinematics of this device are:

$$c_1 = \cos(q_1),\ s_1 = \sin(q_1)$$

$$c_{12} = \cos(q_1 + q_2),\ s_{12} = \sin(q_1 + q_2)$$

$$x = l_1 c_1 + l_2 c_{12} \quad \text{(Eq. 3)}$$

$$y = l_1 s_1 + l_2 s_{12} \quad \text{(Eq. 4)}$$

The Jacobian for such a revolute-revolute robot is derived by taking the partial derivative of the forward kinematics with respect to both $q_1$ and $q_2$.

$$J = \begin{bmatrix} -l_1 s_1 - l_2 s_{12} & -l_2 s_{12} \\ l_1 c_1 + l_2 c_{12} & l_2 c_{12} \end{bmatrix} \quad \text{(Eq. 5)}$$

The Jacobian shown in Equation 5 is the Jacobian for the Cartesian movement of the revolute-revolute robot on the x-y plane (e.g., translation along the y-axis 4016 and the x-axis 4018), describing the differential relationship between joint motion and probe motion. One of ordinary skill in the art would understand that in other embodiments, additional terms may be included in the Jacobian to describe the differential relationship between the motion of the probe 4020 and other motions of the robot (e.g., rotation of the probe 4020 about the tilt axis 4027 and the pan axis 4029 and translation along the z-axis 4013).

Figure 34:
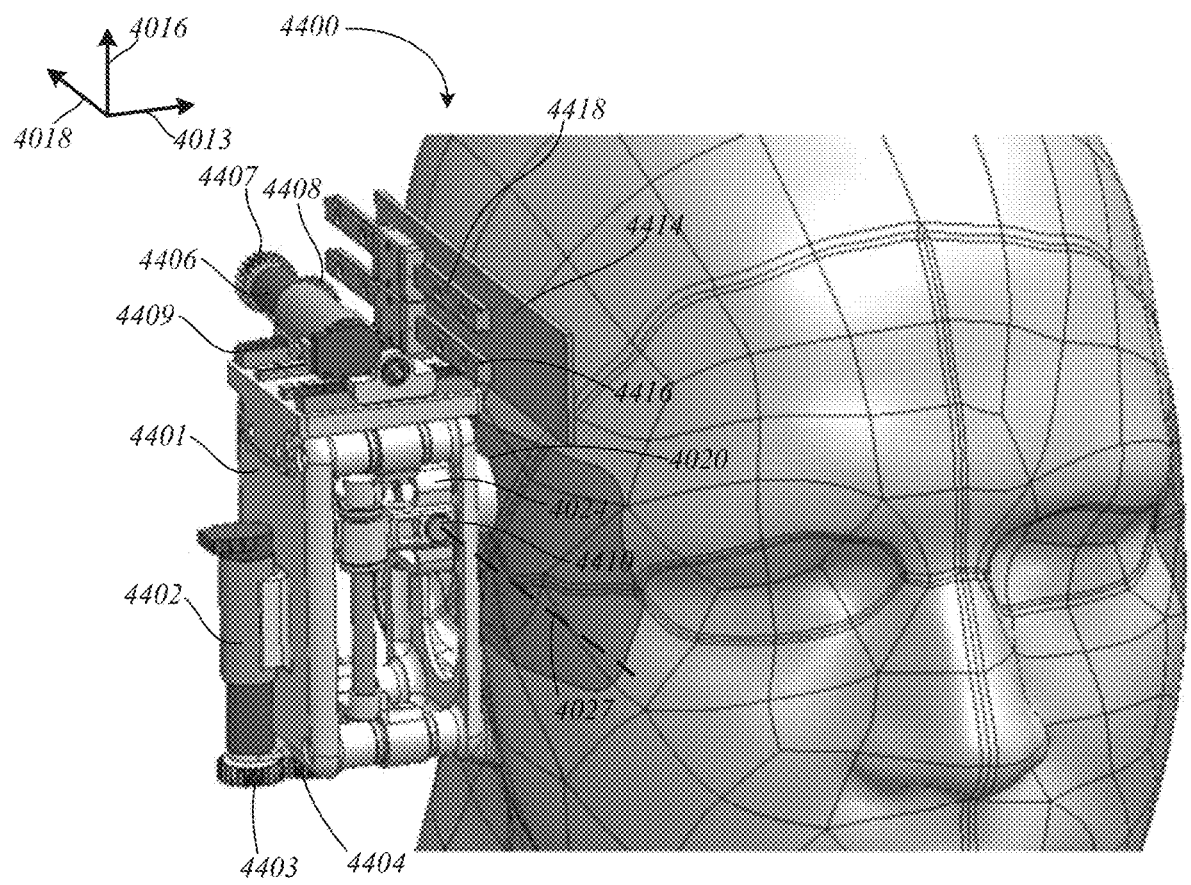
FIG. 34 illustrates a front perspective view of a five actuated degrees of freedom prismatic support structure for a medical probe, according to an exemplary embodiment.

Referring now to FIG. 34, a schematic front view diagram of the support structure 4060 is shown. The probe 4020 is moved in the y direction by a first linear actuator 4100 (e.g., an electric motor and lead screw) and is moved in the x direction by a second linear actuator 4102 (e.g., an electric motor and lead screw). The actuators 4100 and 4102 move the probe 4020 in the x-y plane. Because each joint is orthogonal to the other, and has a one to one mapping of joint motion to Cartesian motion, the Jacobian for such a prismatic robot becomes the identity matrix:

$$J = \begin{bmatrix} 1 & 0 \\ 0 & 1 \end{bmatrix} \quad \text{(Eq. 6)}$$

The Jacobian shown in Equation 6 is the Jacobian for the Cartesian movement of the prismatic robot on the x-y plane (e.g., translation along the y-axis 4016 and the x-axis 4018), describing the differential relationship between joint motion and probe motion. In other embodiments, additional terms may be included in the Jacobian to describe the differential relationship between the motion of the probe 4020 and other motions of the robot (e.g., rotation of the probe 4020 about the tilt axis 4027 and the pan axis 4029 and translation along the z-axis 4013).

Referring to FIG. 10, The support structure 4030 controls the position of the probe 4020 in the z direction with the translation of the fourth frame member 4038 with a single linear actuator (e.g., an electric motor and lead screw). Referring to FIG. 13, Similarly, the support structure 4060 controls the position of the probe 4020 in the z direction with the translation of the fourth frame member 4068 with a single linear actuator (e.g., an electric motor and lead screw). For either support structure, there is a direct correlation between the position of the actuator and the position of the probe 4020.

Figure 18:
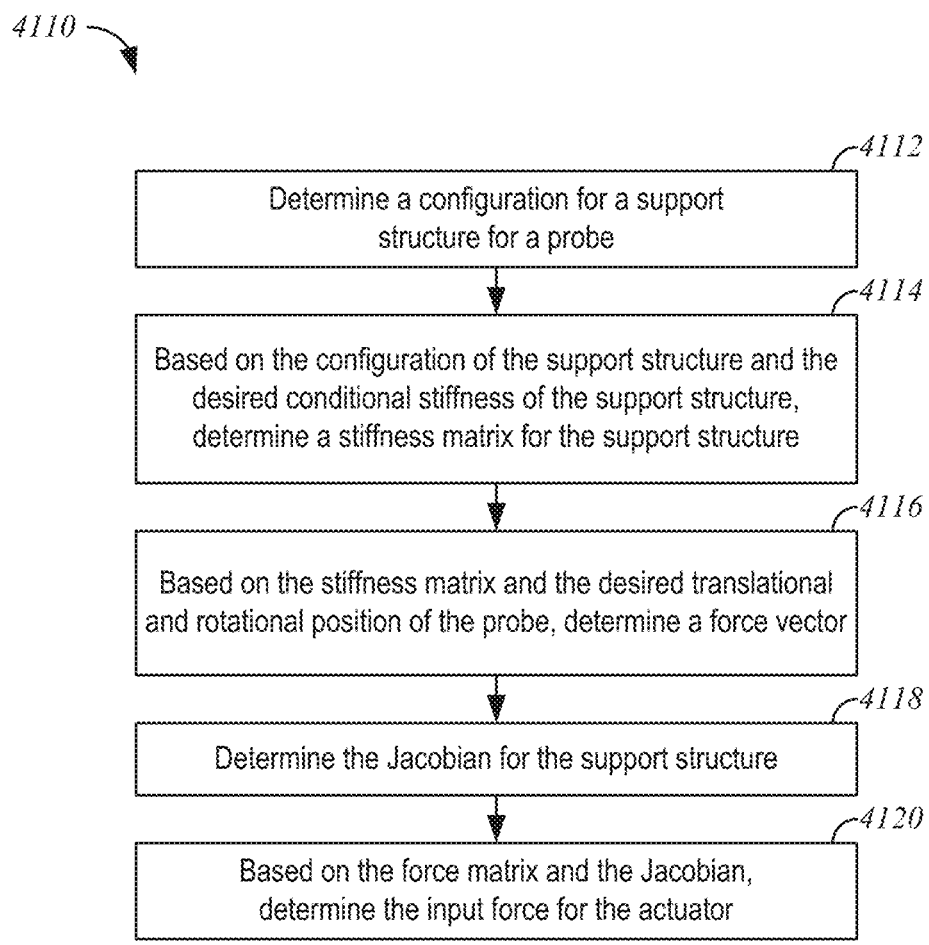
FIG. 18 is a flowchart of a method for determining the input force, or torque, for an actuator, according to an exemplary embodiment.

Referring now to FIG. 18, a method 4110 of determining the input force, or torque, for an actuator for a probe support structure is shown according to an exemplary embodiment. The configuration of the support structure for a probe is first determined (step 4112). The configuration may include any number of revolute joints and/or prismatic joints. In some embodiments, the support structure provides translation of the probe along one or more axis (e.g., the x, y, and z axis in a Cartesian coordinate system; the r, θ, and z axis in a polar coordinate system, etc.) and/or rotation about one or more axis.

Based on the configuration of the support structure and the desired variable stiffness of the support structure, a stiffness matrix for the support structure is determined (step 4114). The stiffness matrix includes terms based on the physical properties of the support structure, including the geometry of the frame members and the stiffness of the individual frame members, the desired stiffness of the support structure in the z direction (Kz), the y direction (Ky), and the x direction (Kx), the desired rotational stiffness of the support structure ($K\omega_x$, $K\omega_y$), and a velocity-based term for system damping.

Based on the stiffness matrix and the desired translational and rotational position of the probe, a force vector is determined (step 4116). The desired position of the probe may be determined using any coordinate system. According to an exemplary embodiment, the force vector is derived from the product of the stiffness matrix and a matrix of the desired translational and rotational position of the probe.

The Jacobian for the support structure is then calculated (step 4118). The Jacobian is determined by the kinematics of the specific support structure. The Jacobian is the differential relationship between the joint positions and the end-effector position. The joint positions are either in units of radians (e.g., for rotational joints), or in units of length (e.g., for prismatic or linear joints). The Jacobian is not static and changes as the support structure position articulates.

Based on the force vector and the Jacobian, the input force for the actuator is determined (step 4120). According to an exemplary embodiment, the input force for the actuator is derived from the product of the Jacobian and the force vector.

Figure 19:
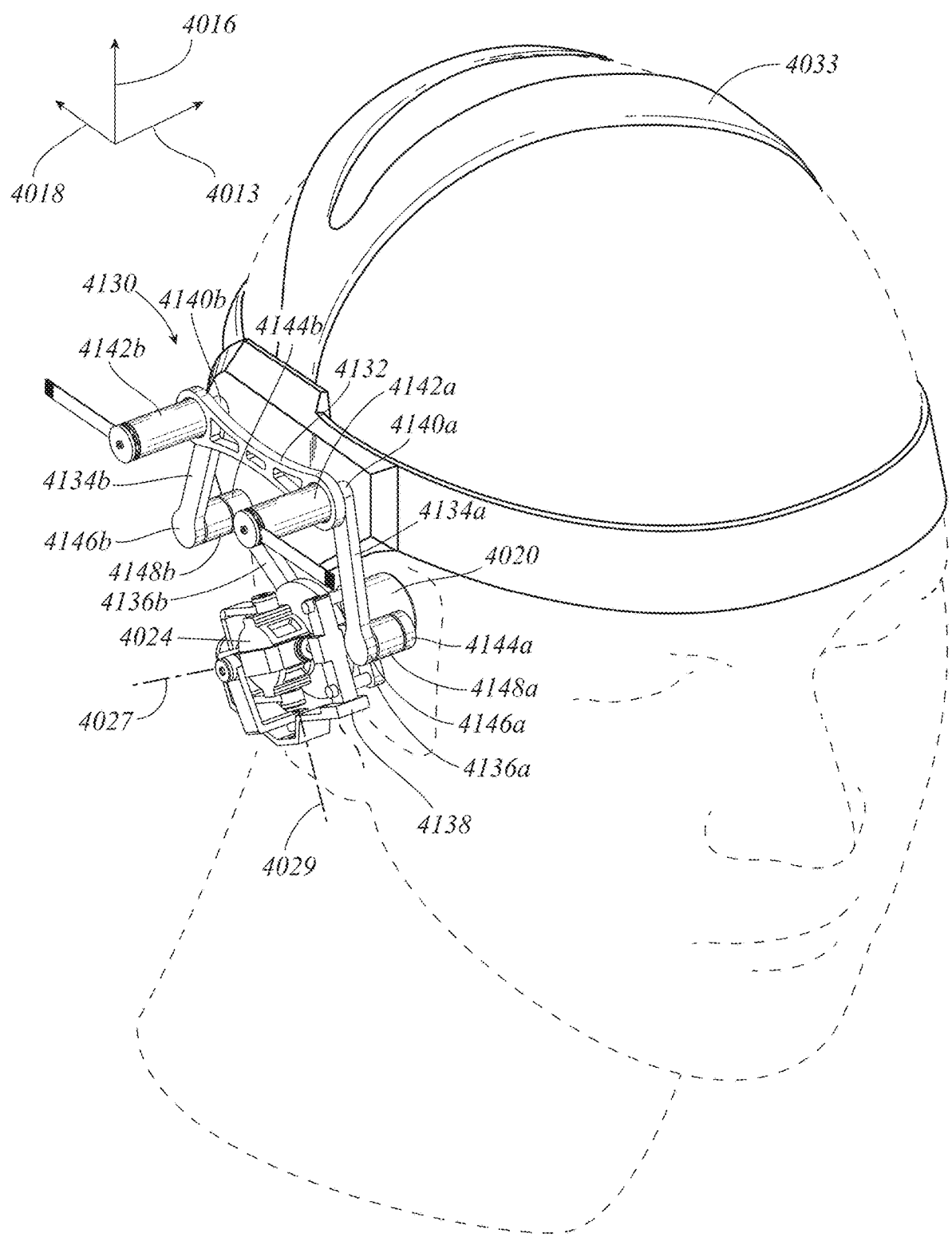
FIG. 19 is a perspective view of a 5-bar parallel mechanism (revolute-revolute) support structure for the medical probe of FIG. 9, according to an exemplary embodiment.
Figure 20:
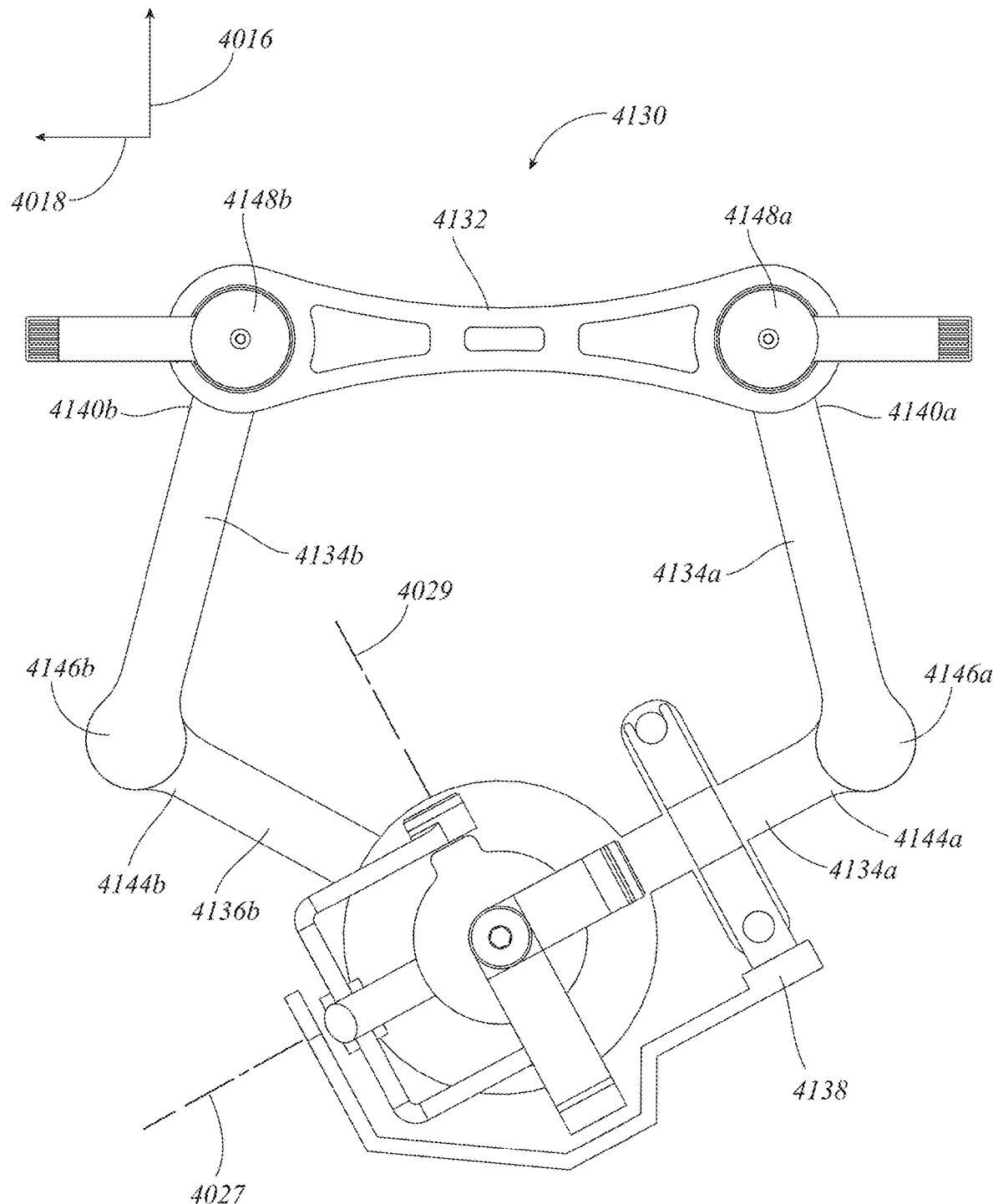
FIG. 20 is front elevation view of the support structure of FIG. 19.
Figure 21:
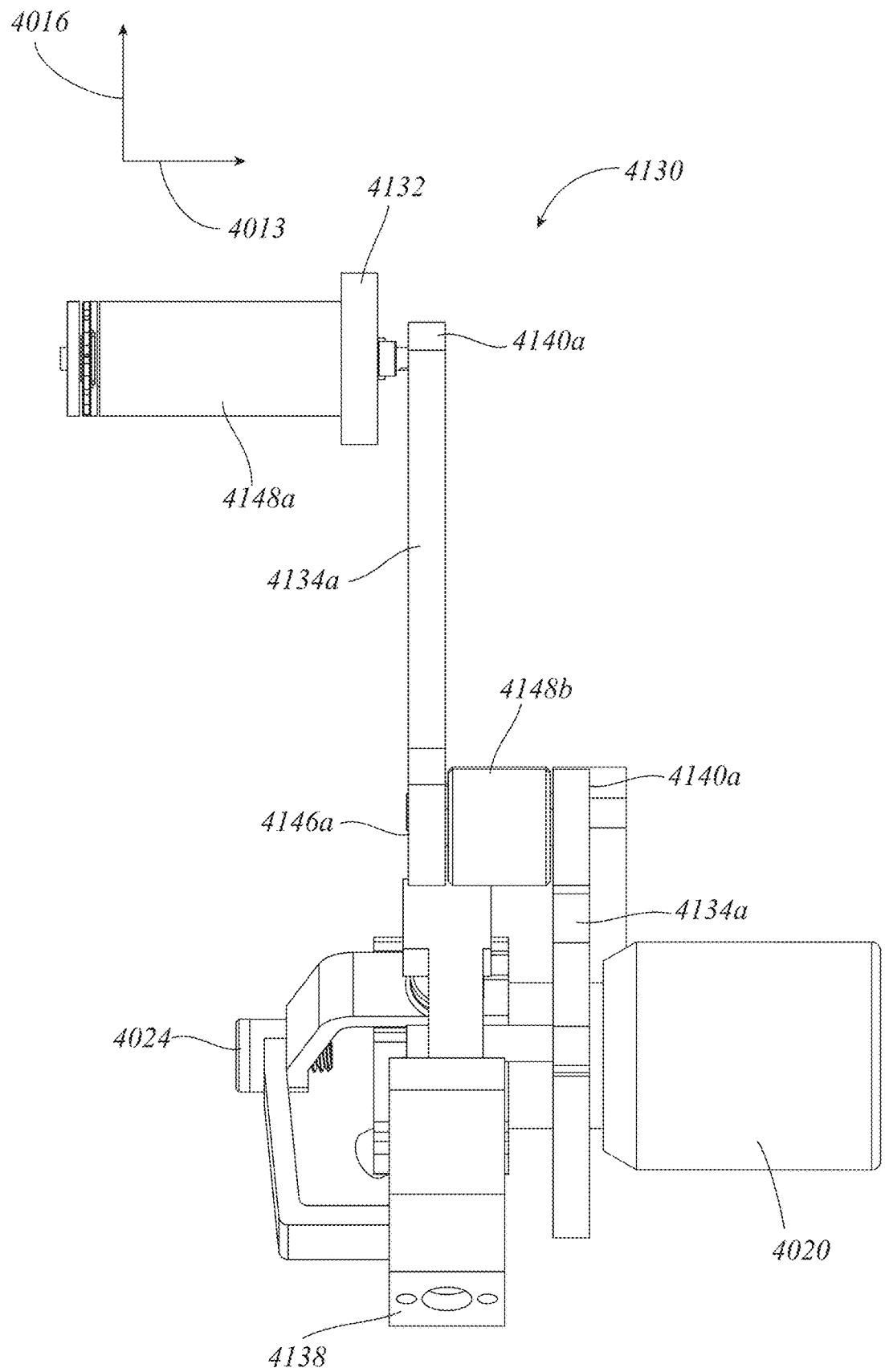
FIG. 21 is a right side elevation view of the support structure of FIG. 19.

Referring now to FIGS. 19-21, a support structure 4130 for the probe 4020 is shown according to another exemplary embodiment as a five-link revolute robot. The support structure 4130 includes a first frame member 4132; a pair of proximal members coupled to the first frame member 4132, shown as a second frame member 4134a and a third frame member 4134b; a pair of distal members coupled to the respective proximal frame members and to each other, shown as a fourth frame member 4136a and a fifth frame member 4136b; a sixth frame member 4138 coupled to the distal frame members; and the gimbal structure 4024. The first frame member 4132 is configured to be a static member. The first frame member 4132 may, for example, be mounted to a halo or headset 4033 worn on the patient's or subject's head or other structure that fixes the position of the first frame member 4132 relative to the patient or subject.

The second frame member 4134a and the third frame member 4134b are links configured to rotate about the z-axis 4013. A first end 4140a of the second frame member 4134a is coupled to the first frame member 4132. Similarly, a first end 4140b of the third frame member 4134b is coupled to a separate portion of the first frame member 4132. According to an exemplary embodiment, the rotation of the second frame member 4134a relative to the first frame member 4132 is controlled by an actuator 4142a, shown as an electric motor and gearbox that is attached through the first frame member 4132. According to an exemplary embodiment, the rotation of the third frame member 4134b relative to the first frame member 4132 is controlled by an actuator 4142b, shown as an electric motor and gearbox that is attached through the first frame member 4132.

The fourth frame member 4136a and the fifth frame member 4136b are links configured to rotate about the z-axis 4013. A first end 4144a of the fourth frame member 4136a and a second end 4146a of the second frame member 4134a are each coupled to a hub member 4148a via bearings (e.g., press fit bearings, etc.). Similarly, a first end 4144b of the fifth frame member 4136b and a second end 4146b of the third frame member 4134b are each coupled to a hub member 4148b via bearings (e.g., press fit bearings, etc.).

The fourth frame member 4136a and the fifth frame member 4136b are coupled together via a bearing (e.g., a press fit bearing, etc.) to form a five-bar linkage. The hub members 4148a and 4148b offset the proximal members from the distal members along the z-axis 4013, which allows the proximal frame members (e.g., second frame member 4134a and third frame member 4134b) to move freely past the distal frame members (e.g., fourth frame member 4136a and fifth frame member 4136b) as the links are rotated by the actuators 4142a and 4142b.

The gimbal structure 4024 and the probe 4020 are mounted to the sixth frame member 4138. The sixth frame member 4138 is coupled to one of the distal members (e.g., fourth frame member 136a or fifth frame member 4136b) and is configured to translate the gimbal structure 4024 and the probe 4020 along the z-axis 4013 (e.g., in and out, in and away from the head, etc.). The sixth frame member 4138 may translate, for example, on rails, as described above in regards to the fourth frame member 4038 of the support structure 4030 (see FIGS. 10-12). The gimbal structure 4024 controls the orientation of the probe 4020 about the tilt axis 4027 and the pan axis 4029 (e.g., pan and tilt). The position of the probe 4020 about the tilt axis 4027 is controlled by an actuator (not shown), such as an electric motor and gearbox. The position of the probe 4020 about the pan axis 4029 is controlled by an actuator (not shown), such as an electric motor and gearbox. In one embodiment, the rotation of the probe 4020 about the tilt axis 4027 and the pan axis 4029 is different than the z-axis 4013, regardless of the rotation of the frame members 4134 and 4136.

The probe 4020 is able to move on the x-y plane through the movement of the five-bar linkage formed by the first frame member 4132, the second frame member 4134a, the third frame member 4134b, the fourth frame member 4136a, and the fifth frame member 4136b. The probe 4020 is able to move along the z-axis 4013 through the translation of the sixth frame member 4138. Further, the probe 4020 is able to rotate about tilt axis 4027 and the pan axis 4029 through the gimbal structure 4024. Combining these five actuated degrees of freedom allows the position and orientation of the probe 4020 relative to the target surface 4022 (See FIGS. 8-9) to be completely described and controlled, discounting rotation about a third axis that is orthogonal to the pan axis 4029 and the tilt axis 4027.

According to an exemplary embodiment, the actuators utilized to position the support structure 4130 are servo motors. Of course, any suitable motors could be used instead of servo motors. The use of servo motors to control the support structure allow for a more precise control, compared to a stepper motor, over the rotational position and angular speed of the motor, as well as the corresponding position of the probe 4020 and the interaction between the probe 4020 and the target surface 4022.

The input forces for the actuators 4142a and 4142b can be calculated in a manner similar to that described above by determining the force vector, determining the forward kinematics of the support structure 4130, and calculating the Jacobian by taking the partial derivative of the forward kinematics with respect to the rotations of each of the actuators 4142a and 4142b.

In some embodiments, for probe 4020 contact and seating, instead of trying to predict and control the exact position and orientation of the probe 4020, the impedance of the probe 4020 is selectively controlled, whether by mechanical design or through software. As such, the orientation degrees of freedom of the probe 4020 can be compliant so that they rotate against contact and seat the probe 4020 flush with the head, while the translation degrees of freedom are stiff enough to move the probe 4020 and keep it placed against the head. In some embodiments, each of the directions has different impedances.

In some embodiments, software is implemented to limit motor torque and motor servo stiffness of the probe 4020. In some embodiments, there may be different limits for each direction, creating different stiffnesses in different directions. In some embodiments, the pan and tilt are very compliant, while the translational motions are moderately stiffer. In some embodiments, stiffness through the probe 4020 is more compliant than the X, Y translational degrees of freedom.

In some embodiments, software is implemented for task space impedance control. In other words, there can be considered the probe 4020 orientation to define a local coordinate system with the Z axis through the center of the probe 4020. Instead of manipulating the impedance of the probe 4020 by adjusting motor servo stiffness and torque limiting, in some embodiments, the kinematics of the entire robot can be considered to set the impedance of each of the five directions, X, Y, Z, pan, and tilt, local to the probe's 4020 coordinate frame. As such, the probe 4020 can be more compliant through the center line of the probe 4020, but still maintain contact with the surface of the skin, but have local X and Y stiffness sufficient to control the location of the probe 4020 with precision.

According to various embodiments, the probe 4020 includes a series elastic actuator. In some embodiments, the impedance of the device is altered by adding a compliant member into the mechanical design, either as a spring element into the motor or as a structural member of the robot. In some embodiments, measurement of the amount of deflection is implemented in order to measure the exact position and orientation of the probe 4020. A series elastic actuator has the benefit of being designed to an exact compliance, and even has a damping element added, while avoiding computational nonlinearities and instabilities associated with programming the impedance.

In some embodiments, the force is indirectly measured by monitoring the applied current of the motor. For the static case, taking into account the kinematics of the robot, the force/torque vector of the system is computed from the Jacobian: $F=(J^T)^{-1}\tau$, where $\tau$ is the vector of motor torques as predicted by the applied current to the motor.

In some embodiments, the interaction force and torque between the probe 4020 and the head is controlled by placing a force/torque sensing mechanism behind the probe 4020. The position and orientation of the probe is specified in relation to the measured forces and torques to achieve a desired force/torque vector. This type of closed loop controller is called admittance control and is programmed into the software. Admittance control relates the measured force to a desired probe position and orientation, as illustrated in the following equation.

$$\vec{X}_{desired}=G_{control}\vec{F}_{measured}$$

Figure 22:
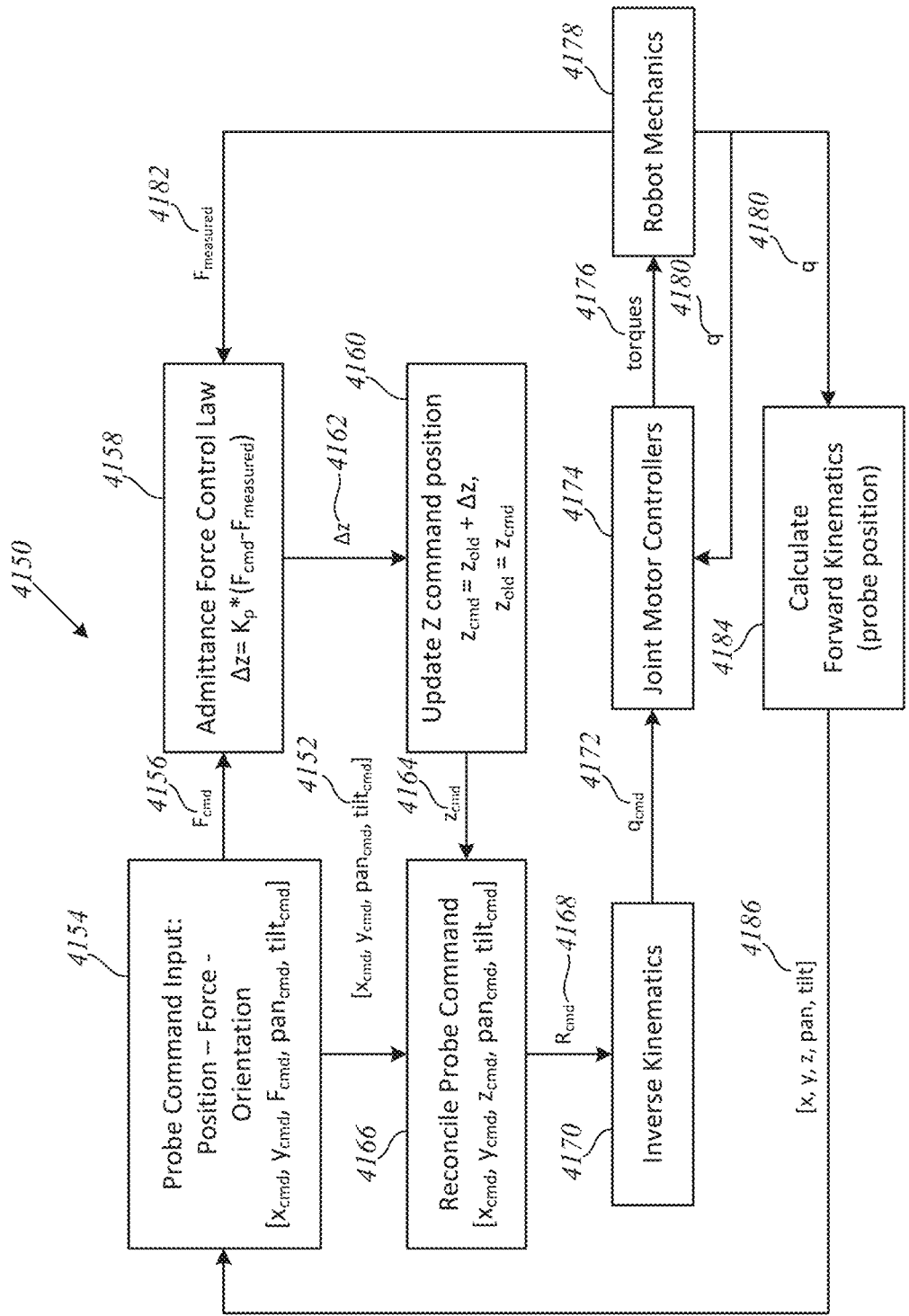
FIG. 22 illustrates a hybrid position-force admittance controller.

The desired position vector is used to compute desired joint positions from the inverse kinematics. Motor joint controllers are programmed with high servo stiffness to enhance disturbance rejection and have low servo tracking errors. A hybrid position-force admittance controller 4150 is illustrated in FIG. 22.

In this example of a hybrid position-force controller, force is controlled in the z direction of the probe, while position is controlled in the x and y directions, and the pan and tilt orientations. A hybrid command of positions and force in task space, $[x_{cmd},y_{cmd},F_{cmd},pan_{cmd},tilt_{cmd}]$ 4152, is sent by the probe command input block 4154, which determines task oriented moves of the probe, such as searching. In this case the position and orientation is specified in x, y, pan and tilt, and is given in units of length and angle (mm and radians). Force is specified in the z direction, and is given in units of Newtons. For an admittance controller, the force command must be transformed into a desired position. The force command, $F_{cmd}$ 4156, is extracted from the probe input command block 4154 as used as the command for the admittance force control block 154. Using the measured force, $F_{measured}$, a change in z position, $\Delta z$, is computed by the admittance force control law block 4158. A simple, single proportional gain controller is illustrated, but other controller forms can be used. In the update z command position block 4160, $\Delta z$ 4162 is added to the old z command position to create an updated z command, $Z_{cmd}$ 4164. This information is merged with the other probe position and orientation commands in the reconcile probe command block 4166. The reconciled command, $R_{cmd}$ 4168 specifies the probe position and orientation in units of length and angle, $[x_{cmd},y_{cmd},z_{cmd},pan_{cmd},tilt_{cmd}]$. The inverse kinematics block 4170 uses the reconciled command, $R_{cmd}$ 4168 to solve for the new robot joint command position, $q_{cmd}$ 4172, based on the mechanics of the specific robot. It is understood from the discussion above that the robot could have a direct analytic inverse solution, or a numerical solution based on the inverse or pseudo inverse Jacobians depending on the number of degrees of freedom.

The joint command position, $q_{cmd}$ 4172, is used as the input for the inner position control loop comprised of the joint motor controllers block 4174, the output torques 4176, robot mechanics block 4178, which is the physical robot, and the measured joint positions, q 4180. The robot mechanics block 4178 also includes a force sensor which outputs the measured force, $F_{measured}$ 4182. The measured force, $F_{measured}$ 4182 is the second input to the admittance force control law block 4158, which closes the force control loop.

The measured joint positions, q 4180, are used as the to the calculate forward kinematics block 4184, which computes the current probe position and orientation [x,y,z,pan, tilt] 4186, and sends it back to the probe command input block 4154, for use in its probe command generation algorithm.

When combined with an impedance law, different directional and orientational stiffnesses at the probe 4020 can be programmed. Admittance control is appropriate for non-backdriveable motors, which are more difficult to use with pure impedance controllers because, without a force-torque sensor, the static friction resisting the user is unobservable while at rest.

Other configurations of the support structure include over and under actuated mechanisms. An over-actuated mechanism, or redundant manipulator, includes more actuated degrees of freedom than task space coordinates that are attempted to be controlled; e.g., the number of motors, Q={J1, J2, J3, J4, J5, . . . ) is greater than the five degrees of freedom in position and orientation X={x, y, z, pan, tilt} of the probe that is being controlled. For such mechanisms there will be many, and possibly an infinite number, of inverse kinematic solutions.

Figure 23:
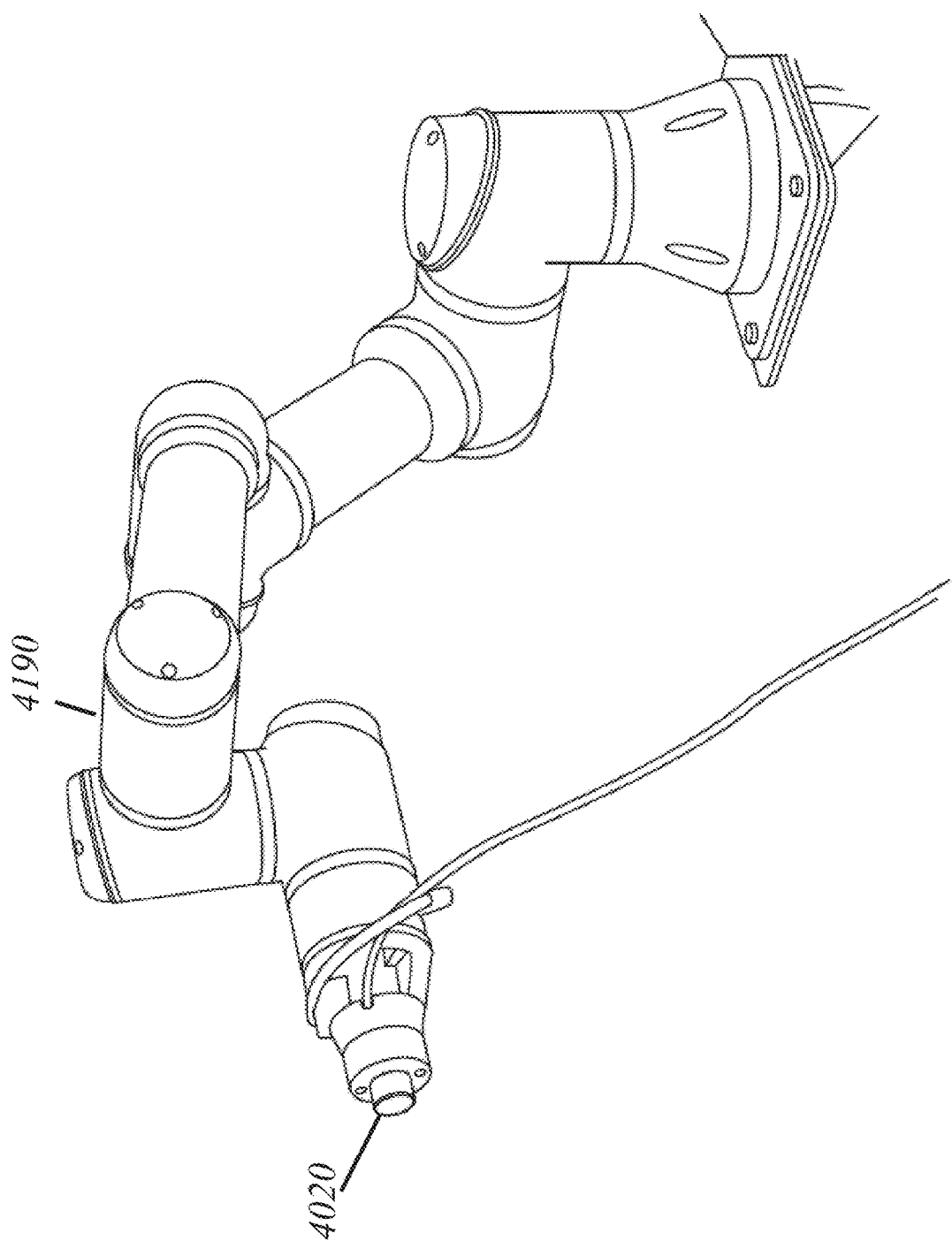
FIG. 23 illustrates a probe on a redundant manipulator.
Figure 24:
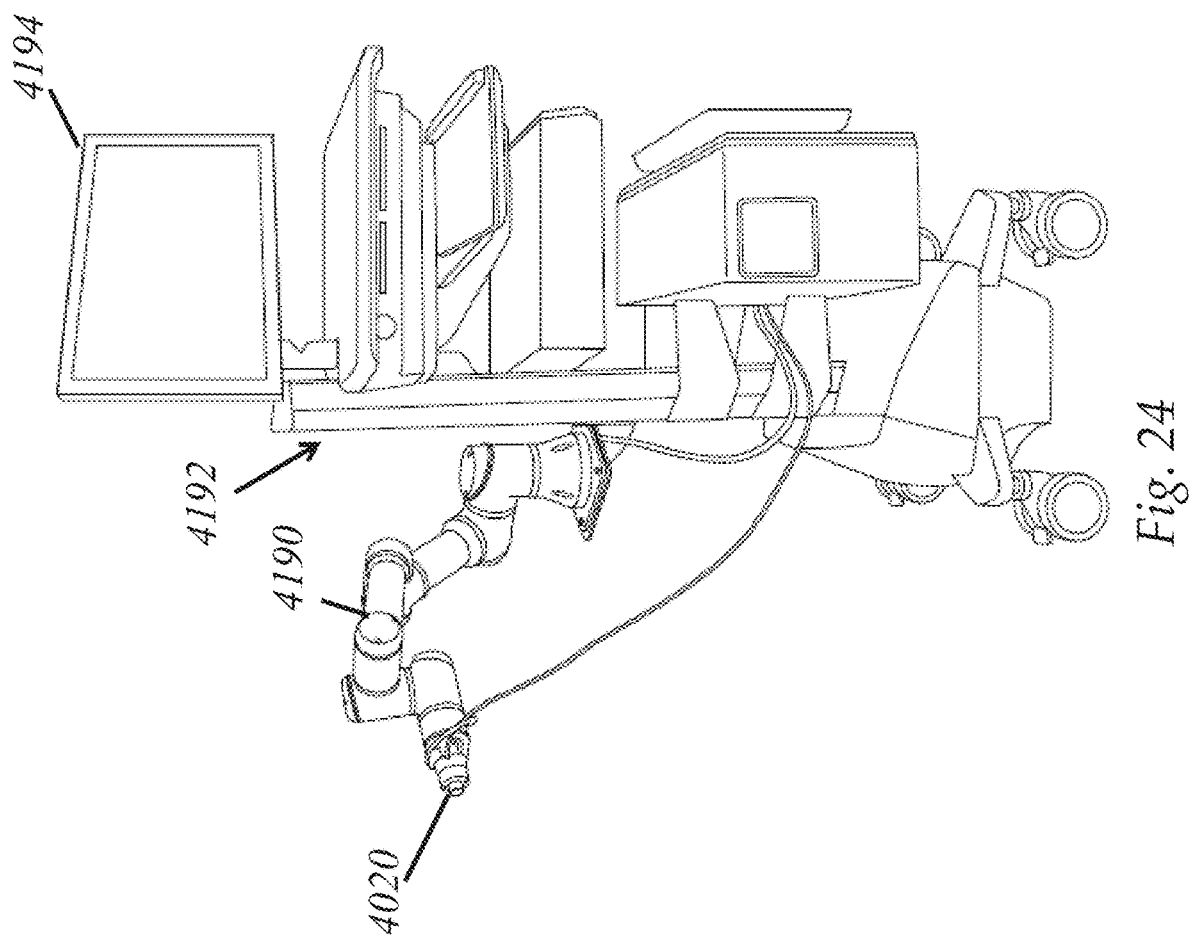
FIG. 24 illustrates a probe on a redundant manipulator mounted on a monitoring station.
Figure 25:
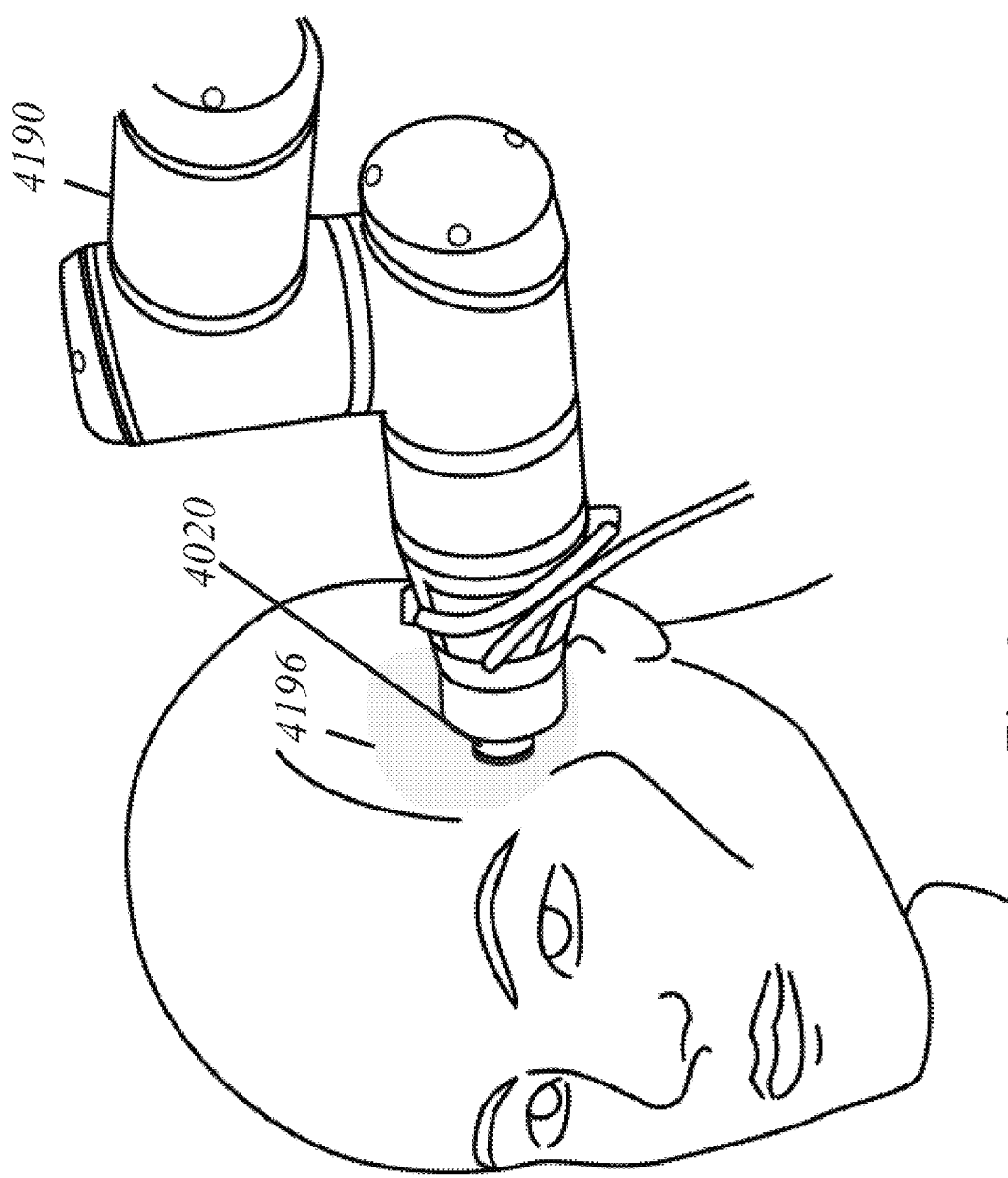
FIG. 25 illustrates a probe on a redundant manipulator scanning through the zygomatic arch.
Figure 26:
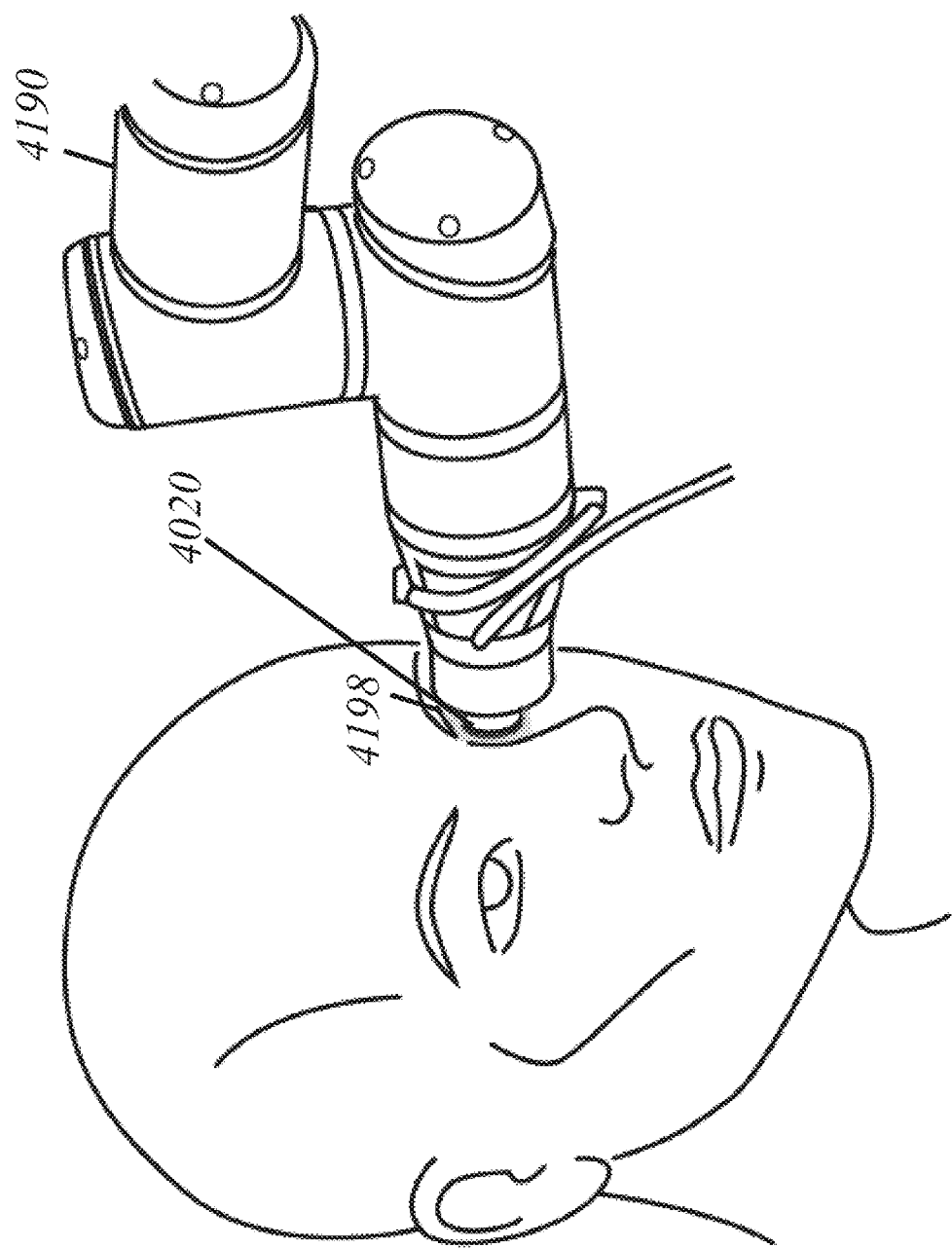
FIG. 26 illustrates a probe on a redundant manipulator performing a transorbital scan through an eye socket or orbit.
Figure 27:
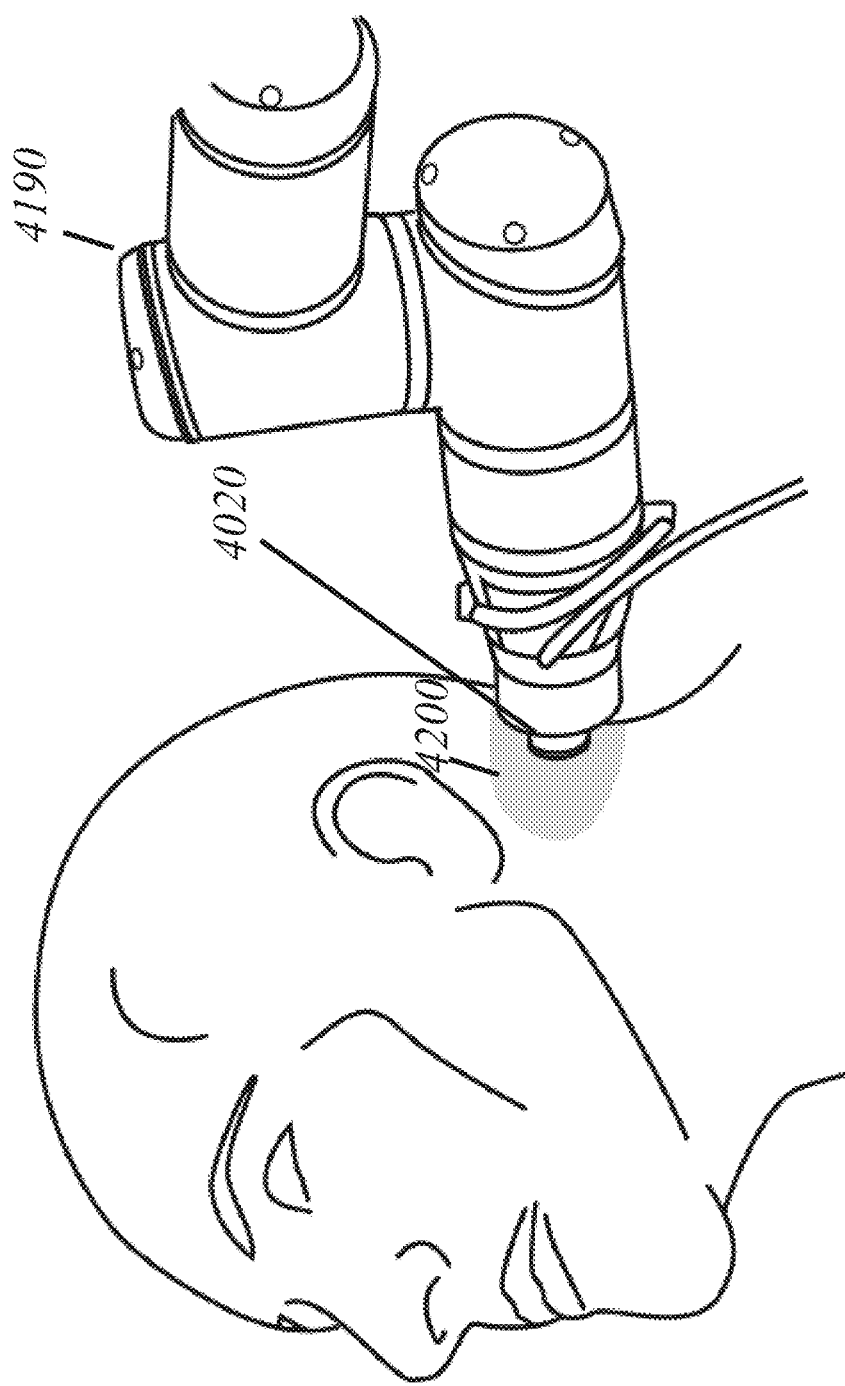
FIG. 27 illustrates a probe on a redundant manipulator scanning through the occipital bone.
Figure 28:
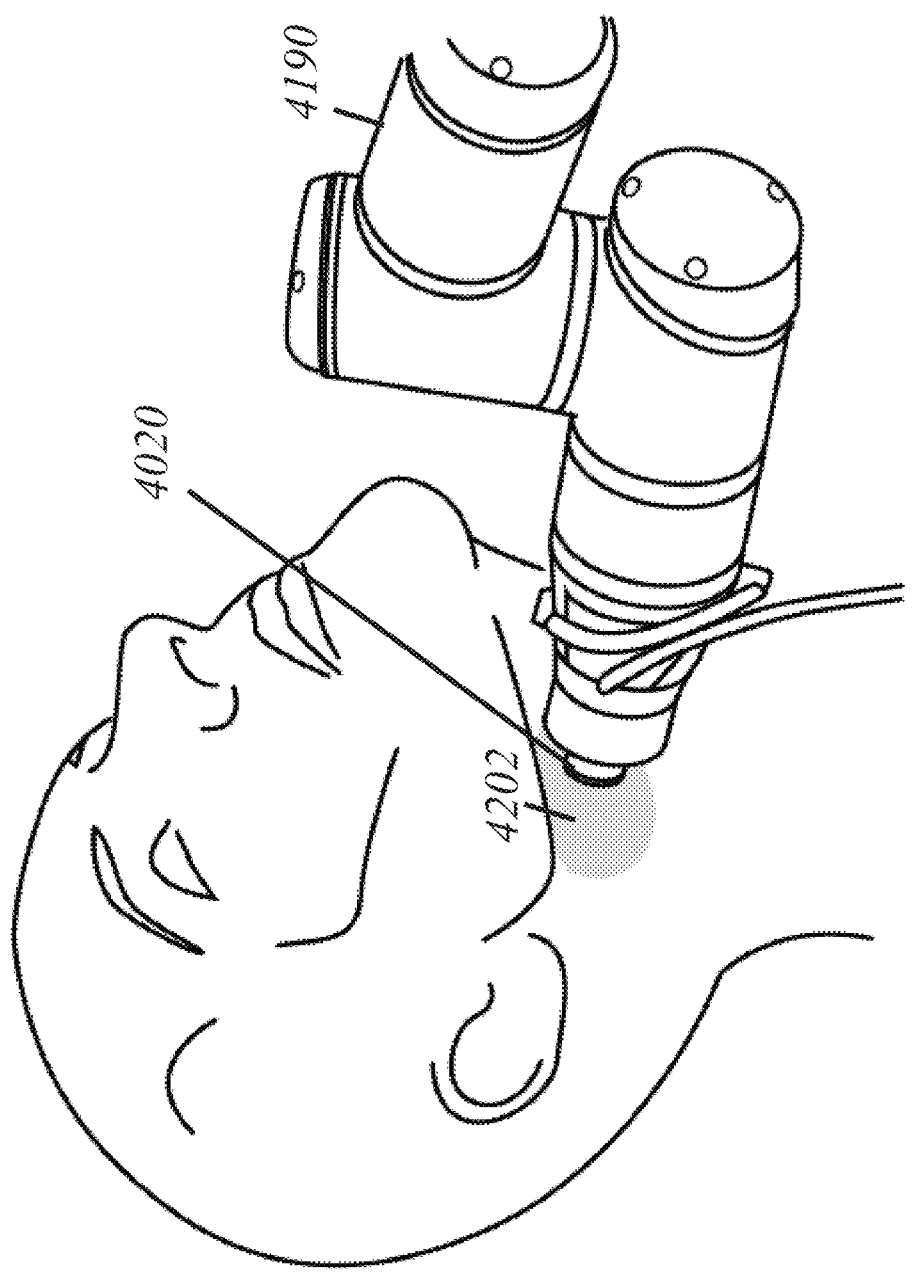
FIG. 28 illustrates a probe on a redundant manipulator scanning through the mandibular.

An example of an over-actuated mechanism, or redundant manipulator, is the UR3 Robot, made by Universal Robots, which has six rotating joints, each controlled by its own actuator or motor, to allow for six actuated degree of freedom movement. Referring to FIG. 23, in some embodiments, a probe 4020 can be placed on a redundant manipulator 4190. Referring to FIG. 14, in some embodiments, the redundant manipulator 4190 may conveniently be mounted on a monitoring station 4192 that may include a display screen 4194. Referring to FIG. 15, the redundant manipulator can be controlled to scan through the zygomatic arch 4196. Referring to FIG. 16, a redundant manipulator can be controlled to perform a transorbital scan through the eye socket or orbit 198. Referring to FIG. 27, the redundant manipulator can be controlled to scan through the occipital bone 4200. Referring to FIG. 28, the redundant manipulator can be controlled to scan through the submandibular 4202.

Figure 29:
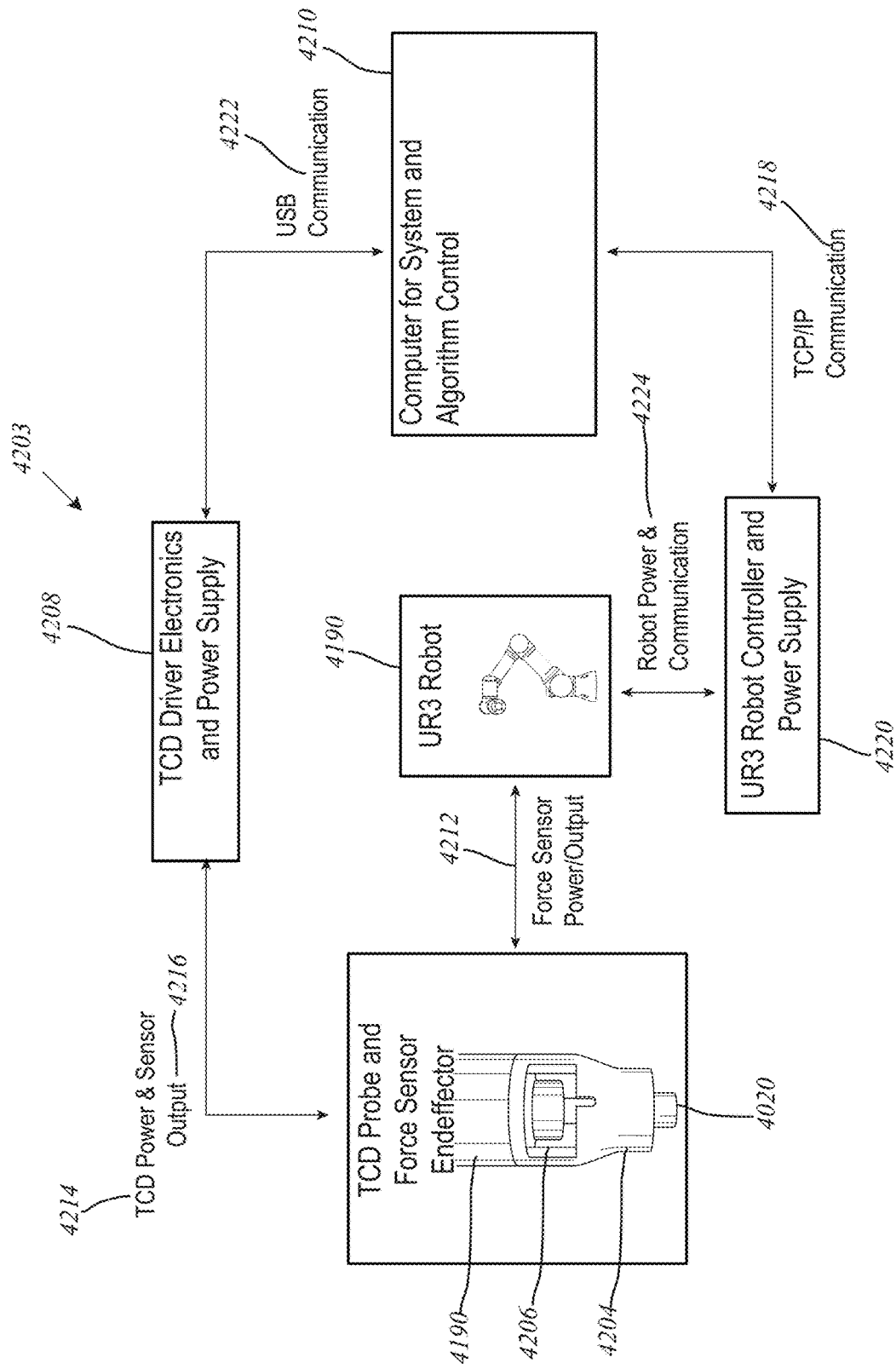
FIG. 29 illustrates a schematic diagram of a TCD system.

As shown in FIG. 29, in some embodiments, an automated TCD system 4203 comprises a redundant manipulator 4190 that provides robotic positioning, probe holder 4204 with force sensor 4206, probe driver board 4208, and control computer 4210. Some embodiments of the redundant manipulator 4190 provide sufficient kinematic precision, have been certified for use around human beings in its workspace, and have settable safety levels to limit velocity and impact forces. These characteristics address safety concerns to allow use with human beings. A probe 4020, that may be a Spencer TCD probe, for insonating vessels in a patient or subject, is mounted onto a probe holder 4204, called an "endeffector." The probe holder 4204 mounts to the end of the redundant manipulator 4190 and has an axial force sensor 4206 to monitor directly force applied by the redundant manipulator 4190 to the surface being scanned. The force sensor 4206 sends force sensor information 4212 to the redundant manipulator 4190. This force sensor 4206 serves both to ensure that enough contact force is made between the probe 4020 and the surface being scanned, but is also a second measure of safety to prevent overloading of contact forces. In some embodiments, the probe driver board 4208 connects to the probe 4020 and provides electronics to send power 4214 to the probe to emit ultrasound energy and process the returned sensor output signal 4216.

In some embodiments, the control computer 4210 connects to the redundant manipulator 4190 controller 4220 via TCP/IP communication 4218 and to the probe driver board 4208 by USB 4222. The redundant manipulator 4190 provides information 4224 about such things as its current position, velocity, estimated forces applied to the endeffector, custom sensor readings, and other status information to controller 4220, which information 4224 is then communicated via TCP/IP 4218 to the control computer 4210. The probe driver board 4208 USB 4222 interface provides a method of setting up probe 4020 parameters and operation, such as depth, and returns processed data, such as the velocity envelope. The control computer 4210 takes all of this information to execute a probe search algorithm and to issue new redundant manipulator 4190 commands to move the redundant manipulator. Embodiments may also employ the use of a machine-learning algorithm to emulate the expertise of a trained technician in locating an insonated vessel. In some embodiments, a control computer 4210 autonomously controls the probe 4020 scanning process, but in other embodiments, a human being may teleoperate the probe 4020 scanning process using technology known to those of skill in the art, such as that used in the NeuroArm and DaVinci surgical robots.

Figure 30:
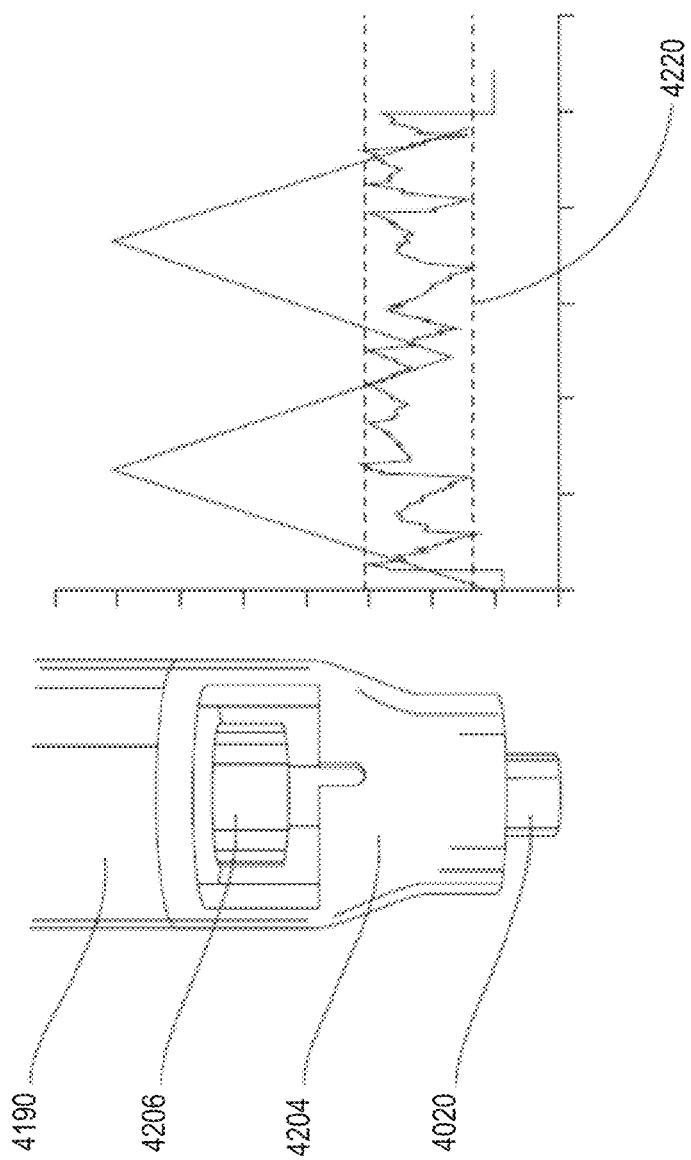
FIG. 30a illustrates a probe on a redundant manipulator.
FIG. 30b illustrates test results of force output for a probe on a redundant manipulator.

Referring now to FIG. 30a and FIG. 30b, FIG. 30a shows the redundant manipulator 4190, force sensor 4206, probe holder 4204, and probe 4020, of FIG. 29. FIG. 30b illustrates the results of tests using this configuration, showing force output controlled to a deadband range 220 of 2 to 10 N.

Integration testing has shown that it is possible to maintain a 125 Hz control loop over the entire system, which is fast enough to read all data from the probe driver board 4208, read all status data from the redundant manipulator 4190, update a signal processing and planning algorithm, and issue a new motion command to the redundant manipulator 4190 at its servo rate.

In some embodiments, a modular snake robot or other robot kinematic configuration with more than six actuated degrees of freedom is used instead of the UR3 as the redundant manipulator.

Figure 31:
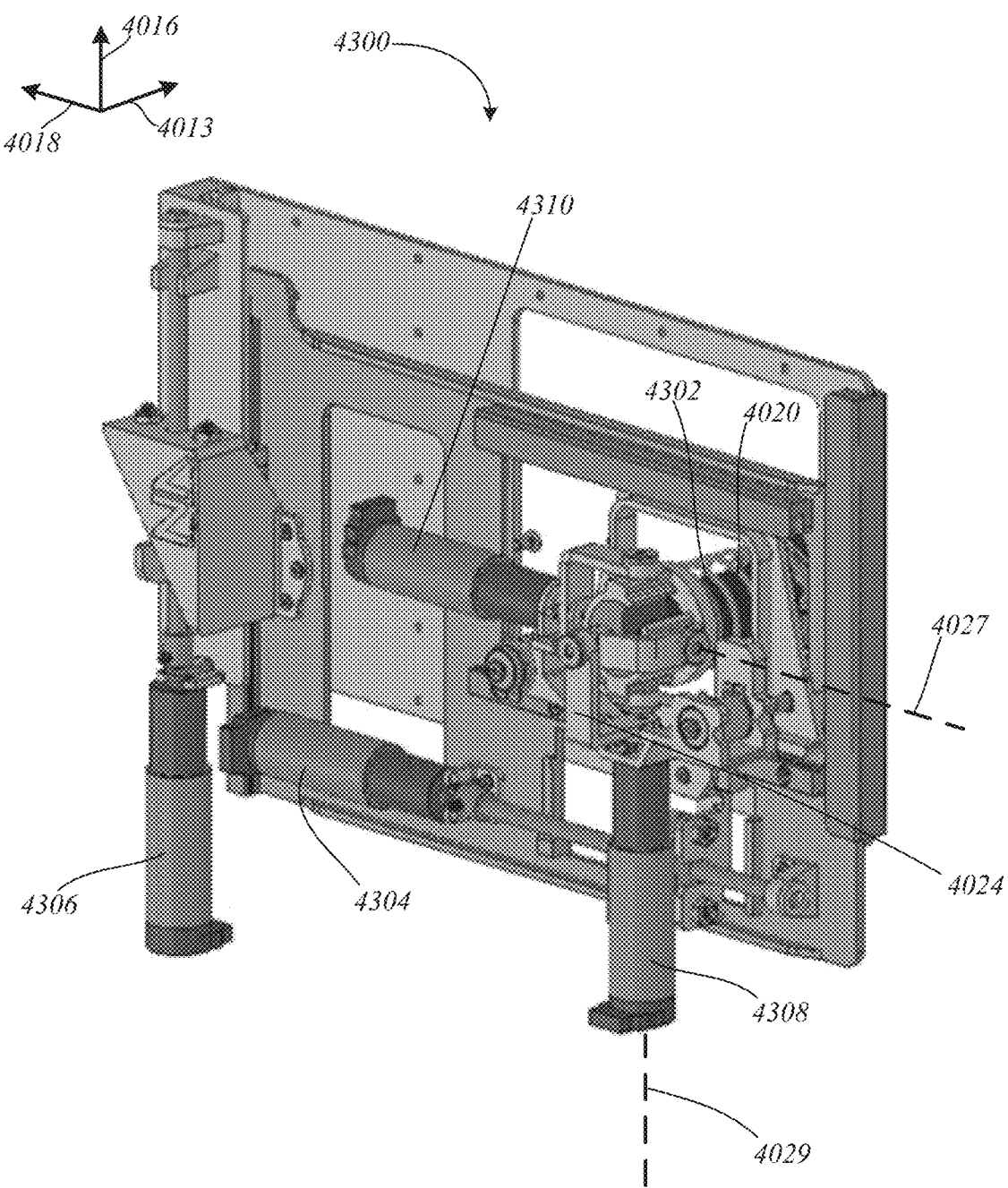
FIG. 31 illustrates a top perspective view of a spring loaded probe in a support structure with four actuated degrees of freedom as well as one passive degree of freedom.
Figure 32:
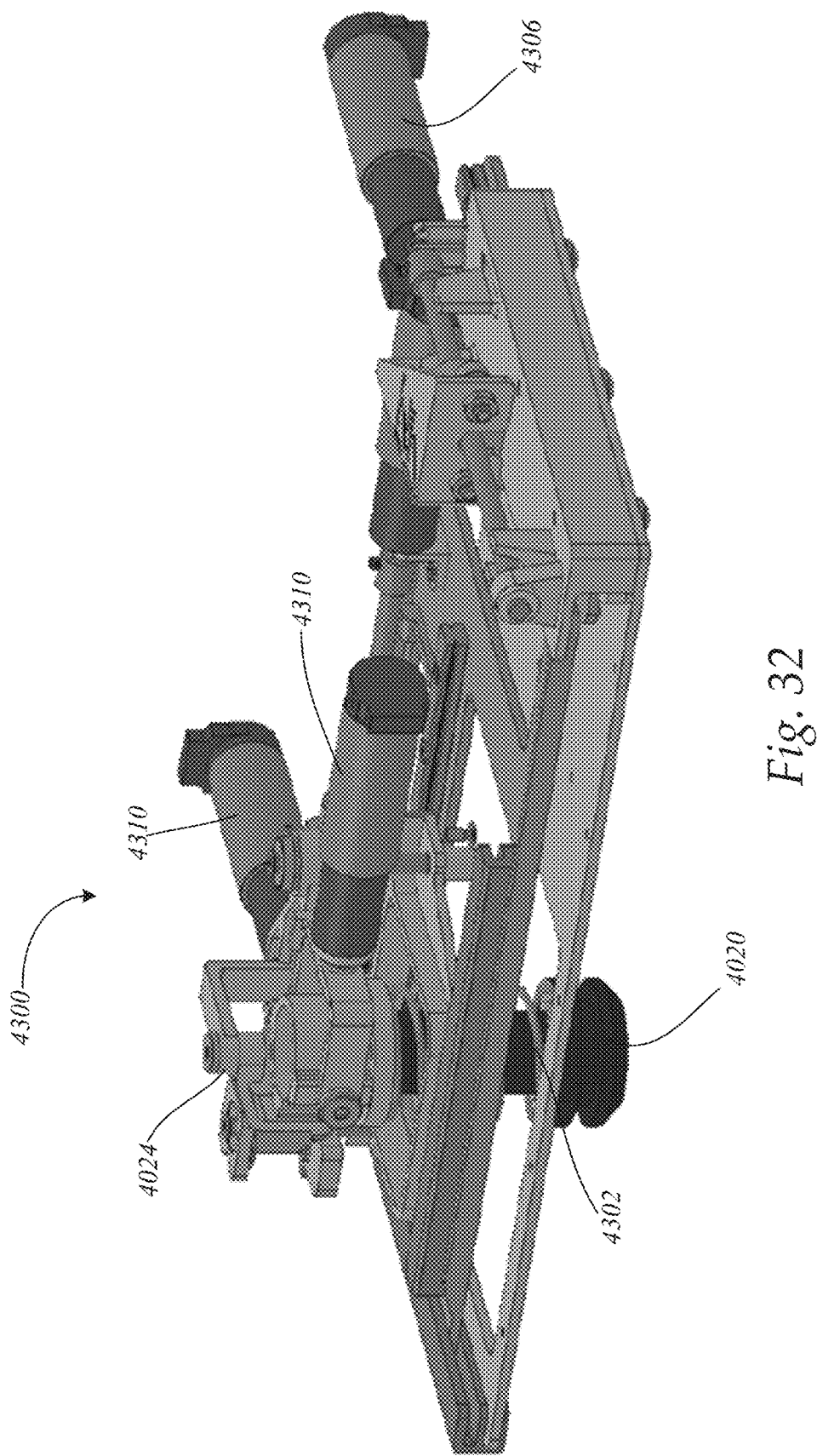
FIG. 32 illustrates a front perspective view of a spring loaded probe in a support structure with four actuated degrees of freedom as well as one passive degree of freedom.
Figure 33:
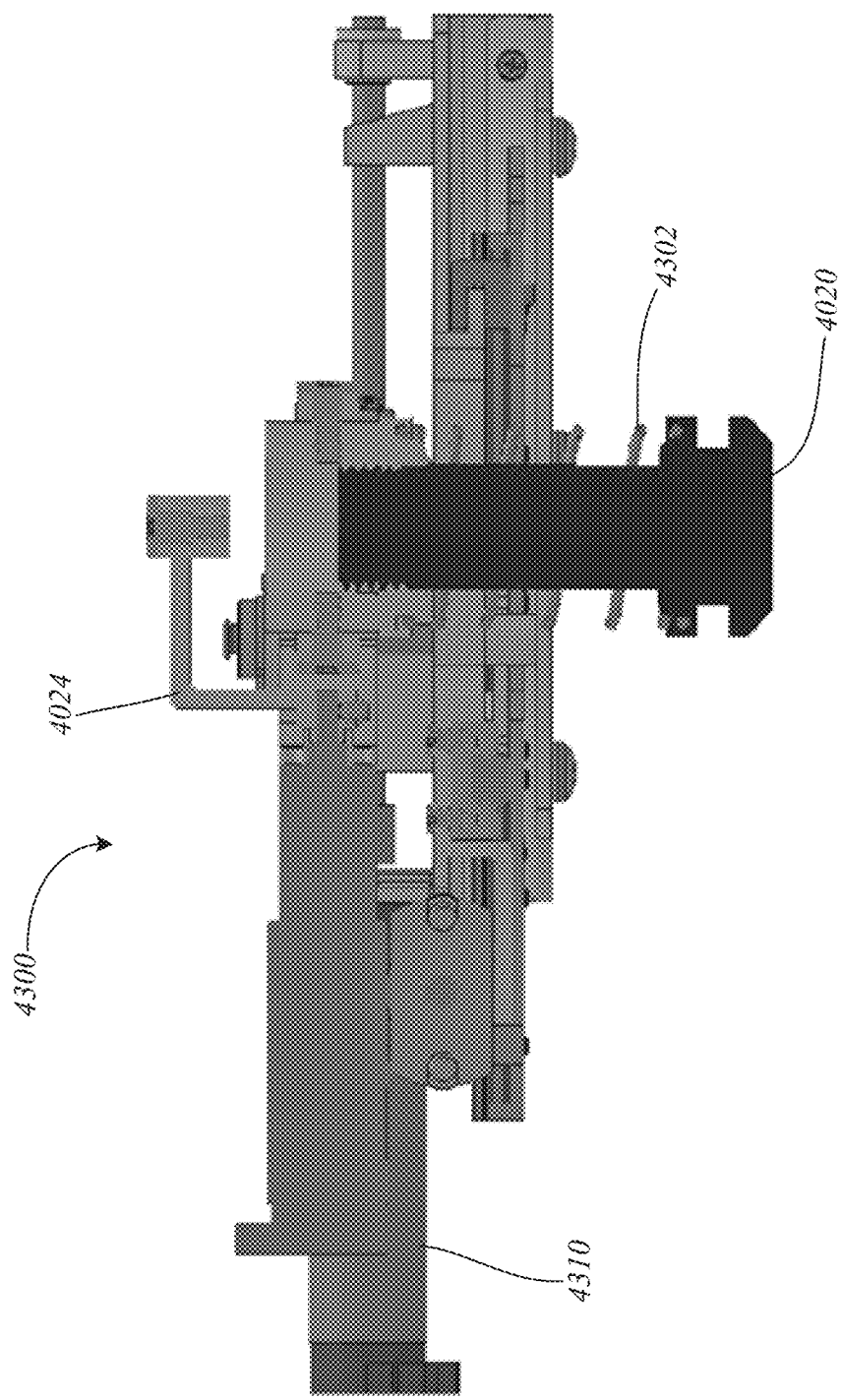
FIG. 33 illustrates a cross-sectional view of a spring loaded probe in a support structure with four actuated degrees of freedom as well as one passive degree of freedom.

Referring now to FIGS. 31-33, an under actuated system 4300 is shown. Such a system has four actuated degrees of freedom in the x,y,pan,tilt axes and a spring providing force along the z axis. In the under actuated system 4300 shown, the system has fewer than five actuated degrees of freedom, but is still capable of performing the TCD positioning task. The under actuated system 4300 shown is a four actuated degree of freedom mechanism that can position and orient the probe 4020 in X={x, y, pan, tilt}. In the under actuated system 4300, a spring 4302 exerts force on the probe 4020 along a z-axis 4013. In five actuated degree of freedom systems the force exerted by the spring in under actuated system 4300 would be actuated by a motor driven mechanism. The gimbal structure 4024 allows the probe 4020 to be oriented. The force in the z-axis 4013 is in effect, monitored by the characterization of the spring constant associated with the spring 4302. The actuation in the x-axis 4018 is controlled by actuator 3404 shown as an electric motor and lead screw. The actuation in the y-axis 4016 is controlled by actuator 4306 shown as an electric motor and lead screw. The actuation in the pan axis 4029 is controlled by motor 4308. The actuation in the tilt axis 4027 is controlled by motor 4310.

Figure 35:
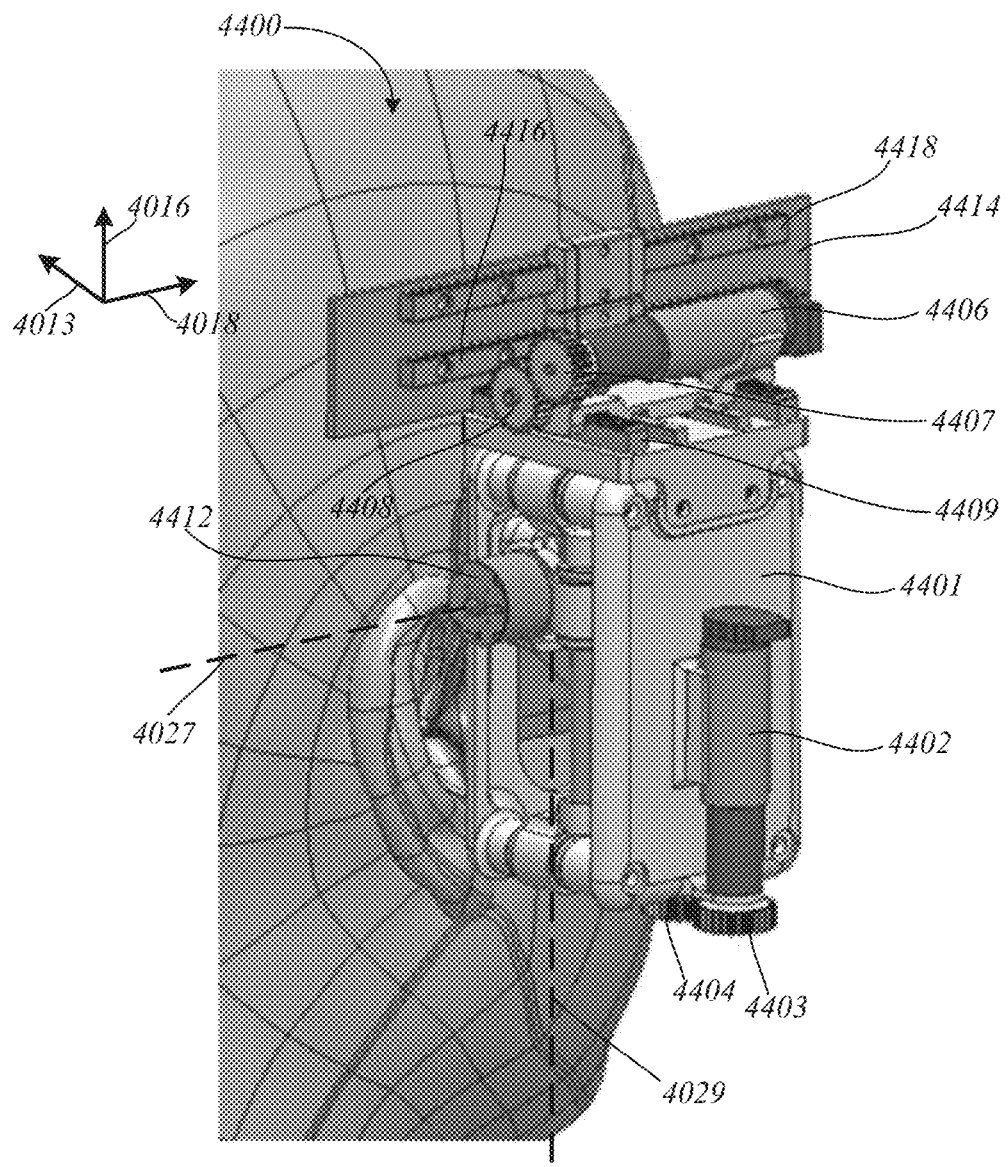
FIG. 35 illustrates a rear perspective view of a five actuated degrees of freedom prismatic support structure for the a medical probe, according to an exemplary embodiment.
Figure 36:
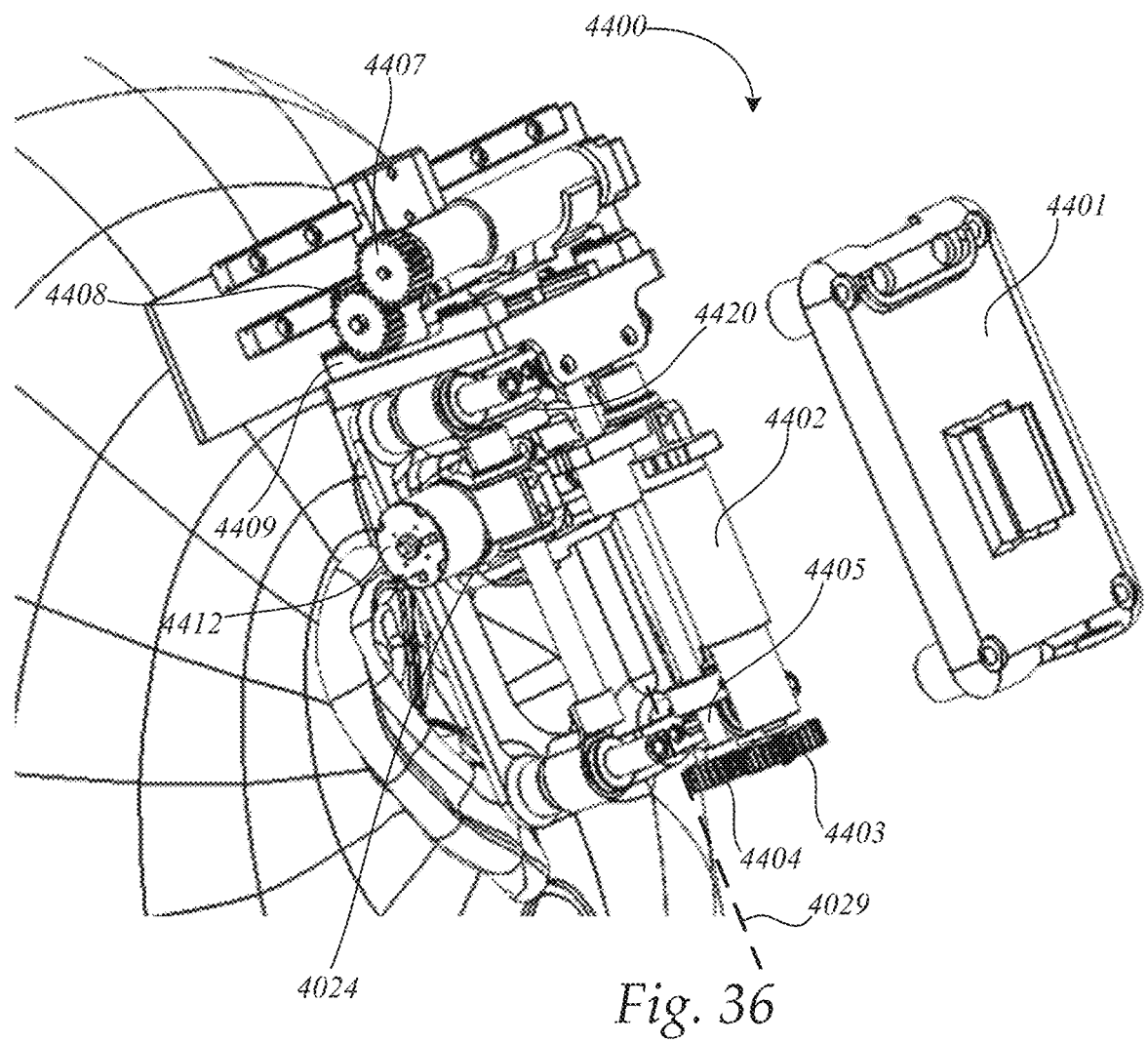
FIG. 36 illustrates an exploded perspective view of a five actuated degrees of freedom prismatic support structure for the a medical probe, according to an exemplary embodiment.

Referring now to FIG. 34, FIG. 35, and FIG. 36 a support structure 4400 is shown for the probe 4020 and the gimbal structure 4024 is shown according to another exemplary embodiment as a prismatic (e.g., Cartesian, rectilinear, etc.) robot. The support structure 4400 may, for example, be mounted to a halo or headset 4033 worn on the patient's or subject's head or other structure. The support structure 4400 includes a cover 4401 that covers some of the mechanisms of the support structure 4400. In FIG. 36, an exploded view of support structure 4400, shows the cover 4401 taken off the support structure 4400.

A first motor 4402 is configured to use a first spur gear 4404 to actuate a lead screw 4405 mechanism. The first spur gear 4403 is coupled to a second spur gear 4404 which converts rotational motion of the first motor 4402 into linear motion along lead screw 4405 to translate the probe 4020 along a y-axis 4016 (e.g., up and down, bottom of ear to top of ear, etc). A second motor 4406 is configured to use a third spur gear 4407 coupled to a fourth spur gear 4408, which in turn is coupled to a rack and pinion mechanism 4409 to translate the probe 4020 along a z-axis 4013 towards and away from the head of a subject. As shown, in FIG. 35, a third motor 4412 and bearing 4410 allow for rotation of the gimbal 4024 about a tilt axis 4027, which in this embodiment, is parallel to x-axis 4018. A plate 4414 houses two linear rails 4416, 4418 and allows for mounting of a fourth motor (not shown for clarity) to translate along the x-axis 4018 (e.g., forward and backward, ear to eye, etc.). As shown in FIG. 36, a fifth motor 4420 allows for controlling rotation of the gimbal 4024 about pan axis 4029, which, in this embodiment is parallel to y-axis 4016, thus completing the necessary degrees of freedom to define five degree of freedom actuated robotic system.

The invention claimed is:

1. A method for determining a neurological condition of a subject using a robotic system comprising a transducer, the method comprising:
    determining, by a computing system, a first location of the transducer with respect to a blood vessel of the subject, the robotic system configured to position the transducer to the first location;

receiving, by the computing system, a first signal from the transducer at the first location in response to the transducer transmitting acoustic energy towards the blood vessel;

analyzing, by the computing system, the received first signal to determine a first parameter of blood flow in the blood vessel;

determining, by the computing system based on the first parameter and a step size, a second location of the transducer with respect to the blood vessel;

moving, by the robotic system, the transducer to the second location with respect to the blood vessel; and determining, by the computing system, the neurological condition of the subject based at least in part on the first parameter of the blood flow in the blood vessel.

2. The method of claim 1, wherein
the second location is different from the first location;
the method further comprising:
receiving, by the computing system, a second signal from the blood vessel in response to the transducer transmitting acoustic energy towards the blood vessel;
analyzing, by the computing system, the received second signal to determine a second parameter of blood flow in the blood vessel; and
the neurological condition is determined based at least in part on the first parameter and the second parameter.

3. The method of claim 2, further comprising, creating, by the computing system, a mapped image of the blood vessel based on the first parameter and the second parameter.

4. The method of claim 3, wherein the mapped image includes positional information of the blood vessel and blood flow information of the blood vessel.

5. The method of claim 3, wherein the mapped image includes an ultrasound image of the blood vessel.

6. The method of claim 3, further comprising, accessing, by the computing system, a database including known blood vessel location information of the subject, wherein the known blood vessel location information is used in creating the mapped image of the blood vessel.

7. The method of claim 3, further comprising, accessing, by the computing system, a database including known blood vessel location information of the subject, wherein the known blood vessel location information is used to determine the first location with respect to the blood vessel.

8. The method of claim 2, further comprising:
calculating, by the computing system, an asymmetric ratio based on the first parameter and the second parameter; and
determining, by the computing system, the neurological condition of the subject based on the asymmetric ratio.

9. The method of claim 8, further comprising:
retrieving, by the computing system, from a database, a scaling factor corresponding to the second location; and
normalizing, by the computing system, the second parameter using the retrieved scaling factor, wherein the asymmetric ratio is determined based on the normalized second parameter.

10. The method of claim 8, further comprising:
determining, by the computing system, that the asymmetric ratio is greater than or less than a predetermined threshold; and
detecting, by the computing system, in response to determining that the asymmetric ratio is greater than or less than the predetermined threshold, the neurological condition.

11. The method of claim 1, wherein the first parameter is a cerebral blood flow velocity (CBFV) of the blood vessel.

12. The method of claim 11, further comprising extracting, by the computing device, a CBFV waveform reflecting a pulse of the CBFV of the blood vessel.

13. The method of claim 12, further comprising:
detecting, by the computing device, a plurality of peaks of the CBFV waveform and a plurality of valleys of the waveform; and
determining, by the computing system, the neurological condition of the subject based on the plurality of peaks and the plurality of valleys of the CBFV waveform.

14. The method of claim 12, further comprising:
determining, by the computing device, a P2 ratio of the CBFV waveform by calculating an amplitude of a second peak of the CBFV waveform divided by an amplitude of the CBFV waveform; and
determining, by the computing device, the neurological condition of the subject based on the P2 ratio.

15. The method of claim 12, further comprising determining, by the computing device, one or more of a cerebral vascular reactivity, mean velocity, or variability based on the CBFV waveform.

16. The method of claim 1, wherein analyzing the received first signal comprises:
estimating, by the computing system, a heart rate of the subject;
determining, by the computing system, a plurality of starting points corresponding to a plurality of beats of the received first signal;
detecting, by the computing system, a plurality of peaks corresponding to the plurality of beats; and
rejecting, by the computing system, a subset of the plurality of beats.

17. The method of claim 16, wherein rejecting the subset is based on rejection criteria including one or more of correlation distance to a mean beat, Euclidean distance to the mean beat, distances of peaks, Mahalanobis distance, jerk and amplitudes of peaks.

18. The method of claim 1, further comprising, accessing, by the computing system, a database including known blood vessel location information of subjects having similar characteristics as those of the subject, wherein the known blood vessel location information is used in creating a mapped image of the blood vessel of the subject.

19. The method of claim 18, wherein the similar characteristics include similar demographic characteristics.

20. The method of claim 1, further comprising:
calculating, by the computing system, a derivative of the first parameter; and
estimating, by the computing system, a maxima or a minima of the first parameter based on the derivative of the first parameter.

21. The method of claim 20, further comprising:
introducing, by the computing system, an error tolerance of the derivative of the first parameter; and
calculating, by the computing system, an almost-maxima or an almost-minima of the first parameter based on the derivative and the error tolerance.

22. The method of claim 1, wherein the first signal includes information with respect to a plurality of depths of the blood vessel received simultaneously in the first signal.

23. The method of claim 1, wherein the first location is at a transtemporal location with respect to the subject.

24. The method of claim 1, wherein the acoustic energy is transcranial Doppler (TCD) energy.

25. The method of claim 1, further comprising:
determining, by the computing system, a curvature of the first parameter; and estimating, by the computing system, based on the curvature, an almost-maxima or an almost-minima of the first parameter.

26. The method of claim 1, further comprising optimizing signals acquired by the transducer by determining, based on the first location, the second location with respect to the blood vessel.

27. The method of claim 1, wherein
the second location of the transducer is determined based on the first parameter, the step size, and a direction; and
the second location is the step size in the direction from the first location.

28. The method of claim 1, wherein
determining the second location comprises determining an error estimate using the first parameter; and
determining the step size using the error estimate, wherein the step size varies based on the error estimate.

29. A robotic system for determining a neurological condition of a subject, the robotic system comprising:
a transducer;
control and signal processing logic configured to control positioning of the transducer and process signals received by the transducer, the control and signal processing logic configured to:
determine a first location of the transducer with respect to a blood vessel of the subject, the robotic system configured to position the transducer to the first location;
receive a first signal from the transducer at the first location in response to the transducer transmitting acoustic energy towards the blood vessel;
analyze the received first signal to determine a first parameter of blood flow in the blood vessel;
determine, based on the first parameter and a step size, a second location of the transducer with respect to the blood vessel;
moving, by the robotic system, the transducer to the second location with respect to the blood vessel; and
determine the neurological condition of the subject based at least in part on the first parameter of the blood flow in the blood vessel.

* * * * *